US005756283A

United States Patent [19]

Wilson et al.

[11] Patent Number: 5,756,283

[45] Date of Patent: May 26, 1998

[54] METHOD FOR IMPROVED PRODUCTION OF RECOMBINANT ADENO-ASSOCIATED VIRUSES FOR GENE THERAPY

[75] Inventors: James M. Wilson, Gladwyne; Krishna J. Fisher, Philadelphia; Guang-Ping Gao, Havertown, all of Pa.

[73] Assignee: The Trustees of the University of Pennsylvania, Philadelphia, Pa.

[21] Appl. No.: 462,014

[22] Filed: Jun. 5, 1995

[51] Int. Cl.$^6$ .............................. C12Q 1/70; C12N 13/00; C12N 7/04; C12N 15/00

[52] U.S. Cl. .................... 435/5; 435/173.3; 435/320.1; 435/236; 435/366; 536/23.1; 536/24.1

[58] Field of Search .................... 536/23.1, 24.1, 536/24.2, 24.5; 514/44; 435/236, 239, 69.2, 173.3, 5, 320.1, 366

[56] References Cited

U.S. PATENT DOCUMENTS

| | | |
|---|---|---|
| 4,797,368 | 1/1989 | Carter et al. . |
| 4,920,209 | 4/1990 | Davis et al. . |
| 5,139,941 | 8/1992 | Muzyczka et al. . |
| 5,173,414 | 12/1992 | Lebkowski et al. . |
| 5,252,479 | 10/1993 | Srivastava . |
| 5,354,678 | 10/1994 | Lebkowski et al. . |
| 5,622,856 | 4/1997 | Natsoulis ............................. 435/325 |

FOREIGN PATENT DOCUMENTS

| | | |
|---|---|---|
| WO91/18088 | 11/1991 | WIPO . |
| WO93/19191 | 9/1993 | WIPO . |
| WO93/24641 | 12/1993 | WIPO . |
| WO94/12649 | 6/1994 | WIPO . |
| WO94/13788 | 6/1994 | WIPO . |
| WO94/17832 | 8/1994 | WIPO . |
| WO94/20517 | 9/1994 | WIPO . |
| WO94/24299 | 10/1994 | WIPO . |
| WO94/26914 | 11/1994 | WIPO . |
| WO94/28152 | 12/1994 | WIPO . |
| WO94/28157 | 12/1994 | WIPO . |
| WO94/28938 | 12/1994 | WIPO . |
| WO95/00655 | 1/1995 | WIPO . |
| WO95/02697 | 1/1995 | WIPO . |
| WO95/06743 | 3/1995 | WIPO . |
| WO95/13392 | 5/1995 | WIPO . |
| WO95/20671 | 8/1995 | WIPO . |
| Wo95/27071 | 10/1995 | WIPO . |
| WO95/33824 | 12/1995 | WIPO . |
| WO95/34671 | 12/1995 | WIPO . |
| WO96/13597 | 5/1996 | WIPO . |
| WO96/13598 | 5/1996 | WIPO . |
| WO96/14061 | 5/1996 | WIPO . |
| WO96/18418 | 6/1996 | WIPO . |
| Wo96/22378 | 7/1996 | WIPO . |

OTHER PUBLICATIONS

P. Hermonat et al, "Use of Adeno–Associated Virus as a Mammalian DNA Cloning Vector: Transduction of Neomycin Resistance into Mammalian Tissue Culture Cells", *Proc. Natl. Acad. Sci USA*, 81:6466–6470 (Oct., 1984).

K. Fisher et al, "Transduction with Recombinant Adeno–Associated Virus for Gene Therapy is Limited by Leading–Strand Synthesis", *J. Virol.*, 70(1):520–532 (Jan., 1996).

M. Weitzman et al, "Recruitment of Wild–Type and Recombinant Adeno–Associated Virus into Adenovirus Replication Centers", *J. Virol.*, 70(3):1845–1854 (Mar., 1996).

P. Nahreini et al, "Cloning and Integration of DNA Fragments in Human Cells via the Inverted Terminal Repeats of the Adeno–Associated Virus 2 Genome", *Gene*, 119:265–272 (1992).

B. Carter, "The Growth Cycle of Adeno–Associated Virus ", in *CRC Handbook of Parvoviruses*, ed. P. Tijssen, vol. I, pp. 155–168 (1990).

U.S. Pat. application No. 08/331,384, filed Oct. 28, 1994.

U.S. Pat. application No. 08/331,381, filed Oct. 28, 1994.

Gunzberg et al., Virus vector design in gene therapy, Molecular Medicine Today, v. 1(9), pp. 410–417, Dec. 1995.

Schlehofer et al., Vacinia virus, herpes simplex, and carcinogens induce DNA amplification in a human cell line and support replication of a helpervirus dependent parvovirus, Virology, v. 152, pp. 110–117, May 1986.

Yacobson et al., Replication of adeno–associated virus in synchronized cells without the addition of a helper virus, J. Virology, v. 64(4), pp. 972–981, Apr. 1987.

McLaughlin et al., Adeno–associated virus general transduction vectors: analysis of proviral structures, J. Virology, v. 62(6), pp. 1963–1973, Jun. 1988.

D. Russell et al, "DNA Synthesis and Topoisomerase Inhibitors Increase Transduction by Adeno–Associated Virus Vectors", *Proc. Natl. Acad. Sci. USA*, 92:5719–5723 (Jun., 1995) [Russell II].

I. Alexander et al, "DNA–Damaging Agents Greatly Increase the Transduction of Nondividing Cells by Adeno–Associated Virus Vectors", *J. Virol.*, 68(12):8282–8287 (Dec., 1994).

F. Collins, "Cystic Fibrosis: Molecular Biology and Therapeutic Implications", *Science*, 256:774–779 (May 8, 1992).

(List continued on next page.)

*Primary Examiner*—David Guzo
*Assistant Examiner*—Andrew Wang
*Attorney, Agent, or Firm*—Howson and Howson

[57] ABSTRACT

A method for enhancing the efficiency of transduction of a recombinant AAV into a target cell is provided. The target cell is infected with a recombinant adeno-associated virus comprising a selected transgene under the control of regulatory sequences. The infected cell is contacted with an agent which facilitates the conversion of single stranded recombinant virus to its double stranded form. When this conversion occurs in the target cell, enhanced transduction of the recombinant virus into said target cell results. The agent can be a helper virus providing a gene which facilitates the conversion, or an agent to which the infected cell is exposed, which facilitates the conversion. In a similar manner, a novel recombinant AAV is provided which contains the facilitating gene and the transgene. The methods may be performed ex vivo or in vivo.

23 Claims, 22 Drawing Sheets

OTHER PUBLICATIONS

B. Davidson et al, "A Model System for in vivo Gene Transfer into the Central Nervous System Using an Adenoviral Vector", Nature Genetics, 3:219–223 (Mar., 1993).

M. Eloit et al, "Construction of a Defective Adenovirus Vector Expressing the Pseudorabies Virus Glycoprotein gp50 and its Use as a Live Vaccine", J. Gen. Virol., 71(10):2425–2431 (Oct., 1990).

J. Engelhardt et al, "Ablation of E2A in Recombinant Adenoviruses Improves Transgene Persistence and Decreases Inflammatory Response in Mouse Liver", Proc. Natl. Acad. Sci. USA, 91:6196–6200 (Jun., 1994) [Engelhardt I].

J. Engelhardt et al, "Adenovirus–Mediated Transfer of the CFTR Gene to Lung of Nonhuman Primates: Biological Efficacy of Study", Human Genet. Ther., 4:759–769 (Dec., 1993) [Engelhardt II].

J. Engelhardt et al, "Prolonged Transgene Expression in Cotton Rat Lung with Recombinant Adenoviruses Defective in E2a", Human Gene Ther., 5:1217–1229 (Oct., 1994) [Engelhardt III].

K. Fisher et al, "Biochemical and Functional Analysis of an Adenovirus–Based Ligand Complex for Gene Transfer", Biochem. J., 299:49–58 (Apr. 1, 1994).

M. Grable et al, "Adenovirus Type 5 Packaging Domain is Composed of a Repeated Element that is Functionally Redundant", J. Virol., 64(5):2047–2056 (May, 1990).

P. Hearing et al, "Identification of a Repeated Sequence Element Required for Efficient Encapsidation of the Adenovirus Type 5 Chromosome", J. Virol., 61(8):2555–2558 (Aug., 1987).

M. Horwitz, "Adenoviridae and Their Replication", Virology, 2d edition, ed. B. N. Fields, Raven Press, Ltd., New York, Chapter 60, pp. 1679–1721 (1990).

S. Ishibashi et al, "Hypercholesterolemia in Low Density Lipoprotein Receptor Knockout Mice and its Reversal by Adenovirus–mediated Gene Delivery", J. Clin. Invest., 92:883–893 (Aug., 1993).

M. Kaplitt et al, "Long–term Gene Expression and Phenotypic Correction Using Adeno–associated Virus Vectors in the Mammalian Brain", Nature Genetics, 8:148–154 (Oct., 1994).

K. Kozarsky et al, "In Vivo Correction of Low Density Lipoprotein Receptor Deficiency in the Watanabe Heritable Hyperlipidemic Rabbit with Recombinant Adenoviruses", J. Biol. Chem., 269(18):13695–13702 (May 6, 1994) [Kozarsky I].

K. Kozarsky et al, "Adenovirus–Mediated Correction of the Genetic Defect in Hepatocytes from Patients with Familial Hypercholesterolemia", Somatic Cell and Molecular Genetics, 19(5):449–458 (Sep., 1993) [Kozarsky II].

K. Kozarsky et al, "Gene Therapy: Adenovirus Vectors", Curr. Opin. Genet. Devel., 3:499–503 (Mar., 1993) [Kozarsky III].

C. Laughlin et al, "Cloning of infectious adeno–associated virus genomes in bacterial plasmids", Gene, 23:65–73 (1983).

J. Logan et al, "Adenovirus Tripartite Leader Sequence Enhances Translation of mRNAs Late After Infection", Proc. Natl. Acad. Sci USA, 81:3655–3659 (Jun., 1984).

B. Roessler et al, "Adenoviral–mediated Gene Transfer to Rabbit Synovium In Vivo", J. Clin. Invest., 92:1085–1092 (Aug., 1993).

D. Russell et al, "Adeno–associated virus vectors preferentially transduce cells in S phase", Proc. Natl. Acad. Sci. USA, 91:8915–8919 (Sep., 1994).

M. Rosenfeld et al, "In Vivo Transfer of the Human Cystic Fibrosis Transmembrane Conductance Regulator Gene to the Airway Epithelium", Cell, 68:143–155 (Jan. 10, 1992).

R. Samulski et al, "Helper–Free Stocks of Recombinant Adeno–Associated Viruses: Normal Integration Does Not Require Viral Gene Expression", J. Virol., 63(9):3822–3828 (Sep., 1989).

T. Shenk et al, "Genetic Analysis of Adenoviruses", Current Topics in Microbiol. and Immunol., 111:1–39 (1984).

W. Smythe et al, "Successful Adenovirus–Mediated Gene Transfer in an In Vivo Model of Human Malignant Mesothelioma", Ann. Thorac. Surg., 57(6):1395–1401 (Jun., 1994).

R. Spessot et al, "Cloning of the Herpes Simplex Virus ICP4 Gene in an Adenovirus Vector: Effects on Adenovirus Gene Expression and Replication", Virol., 168:378–387 (1989).

P. Van Der Vliet et al, "Thermolabile DNA Binding Proteins from Cells Infected with a Temperature–Sensitive Mutant of Adenovirus Defective in Viral DNA Synthesis", J. Virol., 15(2):348–354 (Feb., 1975).

J. Wilson et al, "Vehicles for gene therapy", Nature, 365:691–692 (Oct. 21, 1993).

Y. Yang et al, "MHC Class I–Restricted Cytotoxic T Lymphocytes to Viral Antigens Destroy Hepatocytes in Mice Infected with E1–Deleted Recombinant Adenoviruses", Immunity, 1:433–442 (Aug., 1994) [Yang I].

Y. Yang et al, "Cellular Immunity to Viral Antigens Limits E1–Deleted Adenoviruses for Gene Therapy", Proc. Natl. Acad. Sci. USA, 91:4407–4411 (May, 1994) [Yang II].

Y. Yang et al, "Inactivation of E2a in Recombinant Adenoviruses Improves the Prospect for Gene Therapy in Cystic Fibrosis", Nature Genetics, 7:362–369 (Jul., 1994) [Yang III].

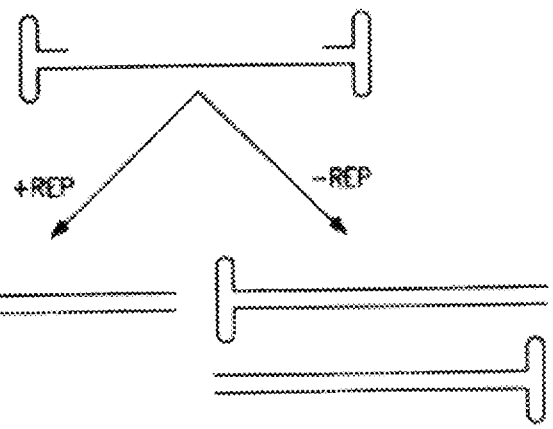
FIG. 4A
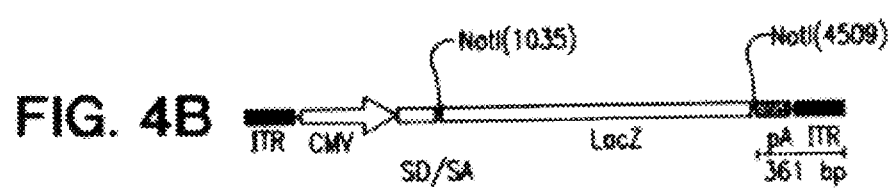
FIG. 4B
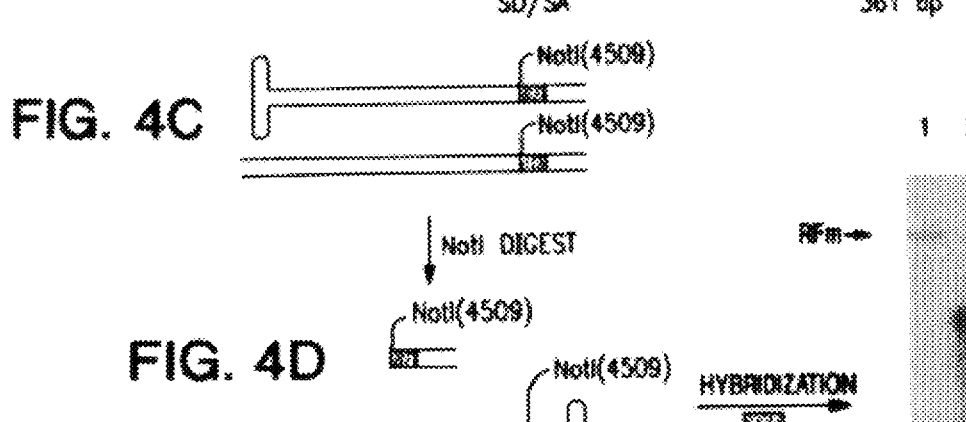
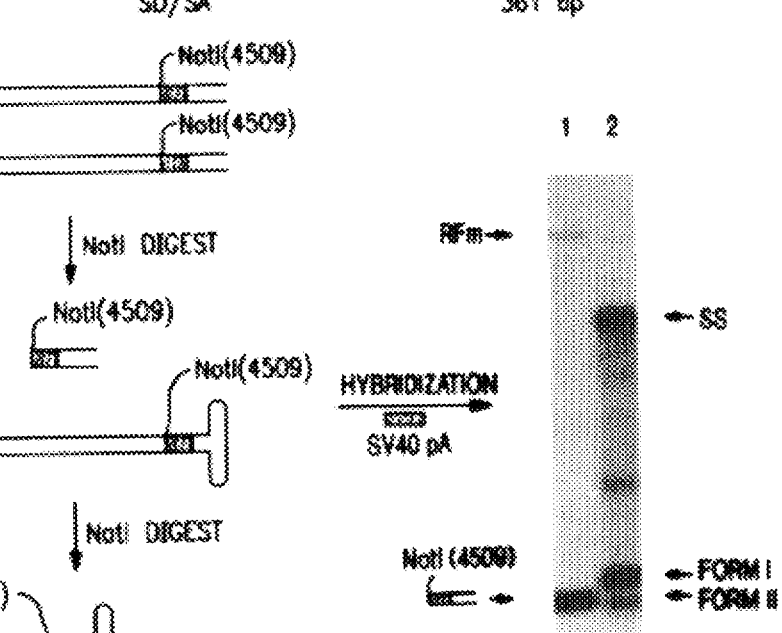
FIG. 4C
FIG. 4D
FIG. 4E
FIG. 4F
FIG. 4G

FIGURE 10A

| | |
|---|---|
| GCCCAATACG CAAACCGCCT CTCCCCGCGC GTTGGCCGAT TCATTAATGC AGCTGCGCGC | 60 |
| TCGCTCGCTC ACTGAGGCCG CCCGGGCAAA GCCCGGGCGT CGGGCGACCT TTGGTCGCCC | 120 |
| GGCCTCAGTG AGCGAGCGAG CGCGCAGAGA GGGAGTGGCC AACTCCATCA CTAGGGGTTC | 180 |
| CTTGTAGTTA ATGATTAACC CGCCATGCTA CTTATCTACG TAGCCATTCT CTAGCCCCTG | 240 |
| CAGGTCGTTA CATAACTTAC GGTAAATGGC CCGCCTGGCT GACCGCCCAA CGACCCCGC | 300 |
| CCATTGACGT CAATAATGAC GTATGTTCCC ATAGTAACGC CAATAGGGAC TTTCCATTGA | 360 |
| CGTCAATGGG TGGAGTATTT ACGGTAAACT GCCCACTTGG CAGTACATCA AGTGTATCAT | 420 |
| ATGCCAAGTA CGCCCCCTAT TGACGTCAAT GACGGTAAAT GGCCCGCCTG GCATTATGCC | 480 |
| CAGTACATGA CCTTATGGGA CTTTCCTACT TGGCAGTACA TCTACGTATT AGTCATCGCT | 540 |
| ATTACCATGG TGATGCGGTT TTGGCAGTAC ATCAATGGGC GTGGATAGCG GTTTGACTCA | 600 |
| CGGGGATTTC CAAGTCTCCA CCCCATTGAC GTCAATGGGA GTTTGTTTTG GCACCAAAAT | 660 |
| CAACGGGACT TTCCAAAATG TCGTAACAAC TCCGCCCCAT TGACGCAAAT GGGCGGTAGG | 720 |
| CGTGTACGGT GGGAGGTCTA TATAAGCAGA GCTCGTTTAG TGAACCGTCA GATCGCCTGG | 780 |
| AGACGCCATC CACGCTGTTT TGACCTCCAT AGAAGACACC GGGACCGATC CAGCCTCCGG | 840 |
| ACTCTAGAGG ATCCGGTACT CGAGGAACTG AAAAACCAGA AAGTTAACTG GTAAGTTTAG | 900 |
| TCTTTTTGTC TTTTATTTCA GGTCCCGGAT CCGGTGGTGG TGCAAATCAA AGAACTGCTC | 960 |
| CTCAGTGGAT GTTGCCTTTA CTTCTAGGCC TGTACGGAAG TGTTACTTCT GCTCTAAAAG | 1020 |
| CTGCGGAATT GTACCCGCGG CCGCAATTCC CGGGGATCGA AGAGCCTGC TAAAGCAAAA | 1080 |
| AAGAAGTCAC CATGTCGTTT ACTTTGACCA ACAAGAACGT GATTTCGTT GCCGGTCTGG | 1140 |
| GAGGCATTGG TCTGGACACC AGCAAGGAGC TGCTCAAGCG CGATCCCGTC GTTTTACAAC | 1200 |
| GTCGTGACTG GAAAACCCT GGCGTTACCC AACTTAATCG CCTTGCAGCA CATCCCCCTT | 1260 |
| TCGCCAGCTG GCGTAATAGC GAAGAGGCCC GCACCGATCG CCCTTCCCAA CAGTTGCGCA | 1320 |
| GCCTGAATGG CGAATGGCGC TTTGCCTGGT TTCCGGCACC AGAAGCGGTG CCGGAAAGCT | 1380 |
| GGCTGGAGTG CGATCTTCCT GAGGCCGATA CTGTCGTCGT CCCCTCAAAC TGGCAGATGC | 1440 |
| ACGGTTACGA TGCGCCCATC TACACCAACG TAACCTATCC CATTACGGTC AATCCGCCGT | 1500 |
| TTGTTCCCAC GGAGAATCCG ACGGGTTGTT ACTCGCTCAC ATTTAATGTT GATGAAAGCT | 1560 |
| GGCTACAGGA AGGCCAGACG CGAATTATTT TTGATGGCGT TAACTCGGCG TTTCATCTGT | 1620 |
| GGTGCAACGG GCGCTGGGTC GGTTACGGCC AGGACAGTCG TTTGCCGTCT GAATTTGACC | 1680 |
| TGAGCGCATT TTTACGCGCC GGAGAAAACC GCCTCGCGGT GATGGTGCTG CGTTGGAGTG | 1740 |

FIGURE 10B

```
ACGGCAGTTA TCTGGAAGAT CAGGATATGT GGCGGATGAG CGGCATTTTC CGTGACGTCT    1800
CGTTGCTGCA TAAACCGACT ACACAAATCA GCGATTTCCA TGTTGCCACT CGCTTTAATG    1860
ATGATTTCAG CCGCGCTGTA CTGGAGGCTG AAGTTCAGAT GTGCGGCGAG TTGCGTGACT    1920
ACCTACGGGT AACAGTTTCT TTATGGCAGG GTGAAACGCA GGTCGCCAGC GGCACCGCGC    1980
CTTTCGGCGG TGAAATTATC GATGAGCGTG GTGGTTATGC CGATCGCGTC ACACTACGTC    2040
TGAACGTCGA AAACCCGAAA CTGTGGAGCG CCGAAATCCC GAATCTCTAT CGTGCGGTGG    2100
TTGAACTGCA CACCGCCGAC GGCACGCTGA TTGAAGCAGA AGCCTGCGAT GTCGGTTTCC    2160
GCGAGGTGCG GATTGAAAAT GGTCTGCTGC TGCTGAACGG CAAGCCGTTG CTGATTCGAG    2220
GCGTTAACCG TCACGAGCAT CATCCTCTGC ATGGTCAGGT CATGGATGAG CAGACGATGG    2280
TGCAGGATAT CCTGCTGATG AAGCAGAACA ACTTTAACGC CGTGCGCTGT TCGCATTATC    2340
CGAACCATCC GCTGTGGTAC ACGCTGTGCG ACCGCTACGG CCTGTATGTG GTGGATGAAG    2400
CCAATATTGA AACCCACGGC ATGGTGCCAA TGAATCGTCT GACCGATGAT CCGCGCTGGC    2460
TACCGGCGAT GAGCGAACGC GTAACGCGAA TGGTGCAGCG CGATCGTAAT CACCCGAGTG    2520
TGATCATCTG GTCGCTGGGG AATGAATCAG GCCACGGCGC TAATCACGAC GCGCTGTATC    2580
GCTGGATCAA ATCTGTCGAT CCTTCCCGCC GGTGCAGTA TGAAGGCGGC GGAGCCGACA    2640
CCACGGCCAC CGATATTATT TGCCCGATGT ACGCGCGCGT GGATGAAGAC CAGCCCTTCC    2700
CGGCTGTGCC GAAATGGTCC ATCAAAAAAT GGCTTTCGCT ACCTGGAGAG ACGCGCCCGC    2760
TGATCCTTTG CGAATACGCC CACGCGATGG GTAACAGTCT TGGCGGTTTC GCTAAATACT    2820
GGCAGGCGTT TCGTCAGTAT CCCCGTTTAC AGGGCGGCTT CGTCTGGGAC TGGGTGGATC    2880
AGTCGCTGAT TAAATATGAT GAAAACGGCA ACCCGTGGTC GGCTTACGGC GGTGATTTTG    2940
GCGATACGCC GAACGATCGC CAGTTCTGTA TGAACGGTCT GGTCTTTGCC GACCGCACGC    3000
CGCATCCAGC GCTGACGGAA GCAAAACACC AGCAGCAGTT TTTCCAGTTC CGTTTATCCG    3060
GGCAAACCAT CGAAGTGACC AGCGAATACC TGTTCCGTCA TAGCGATAAC GAGCTCCTGC    3120
ACTGGATGGT GGCGCTGGAT GGTAAGCCGC TGGCAAGCGG TGAAGTGCCT CTGGATGTCG    3180
CTCCACAAGG TAAACAGTTG ATTGAACTGC CTGAACTACC GCAGCCGGAG AGCGCCGGGC    3240
AACTCTGGCT CACAGTACGC GTAGTGCAAC CGAACGCGAC CGCATGGTCA GAAGCCGGGC    3300
ACATCAGCGC CTGGCAGCAG TGGCGTCTGG CGGAAAACCT CAGTGTGACG CTCCCCGCCG    3360
CGTCCCACGC CATCCCGCAT CTGACCACCA GCGAAATGGA TTTTTGCATC GAGCTGGGTA    3420
ATAAGCGTTG GCAATTTAAC CGCCAGTCAG GCTTTCTTTC ACAGATGTGG ATTGGCGATA    3480
```

FIGURE 10C

```
AAAAACAACT GCTGACGCCG CTGCGCGATC AGTTCACCCG TGCACCGCTG GATAACGACA    3540
TTGGCGTAAG TGAAGCGACC CGCATTGACC CTAACGCCTG GGTCGAACGC TGGAAGGCGG    3600
CGGGCCATTA CCAGGCCGAA GCAGCGTTGT TGCAGTGCAC GGCAGATACA CTTGCTGATG    3660
CGGTGCTGAT TACGACCGCT CACGCGTGGC AGCATCAGGG GAAAACCTTA TTTATCAGCC    3720
GGAAAACCTA CCGGATTGAT GGTAGTGGTC AAATGGCGAT TACCGTTGAT GTTGAAGTGG    3780
CGAGCGATAC ACCGCATCCG GCGCGGATTG GCCTGAACTG CCAGCTGGCG CAGGTAGCAG    3840
AGCGGGTAAA CTGGCTCGGA TTAGGGCCGC AAGAAAACTA TCCCGACCGC CTTACTGCCG    3900
CCTGTTTTGA CCGCTGGGAT CTGCCATTGT CAGACATGTA TACCCCGTAC GTCTTCCCGA    3960
GCGAAAACGG TCTGCGCTGC GGACGCGCG AATTGAATTA TGGCCCACAC CAGTGGCGCG     4020
GCGACTTCCA GTTCAACATC AGCCGCTACA GTCAACAGCA ACTGATGGAA ACCAGCCATC    4080
GCCATCTGCT GCACGCGGAA GAAGGCACAT GGCTGAATAT CGACGGTTTC CATATGGGGA    4140
TTGGTGGCGA CGACTCCTGG AGCCCGTCAG TATCGGCGGA ATTACAGCTG AGCGCCGGTC    4200
GCTACCATTA CCAGTTGGTC TGGTGTCAAA AATAATAATA ACCGGGCAGG CCATGTCTGC    4260
CCGTATTTCG CGTAAGGAAA TCCATTATGT ACTATTTAAA AAACACAAAC TTTTGGATGT    4320
TCGGTTTATT CTTTTTCTTT TACTTTTTTA TCATGGGAGC CTACTTCCCG TTTTTCCCGA    4380
TTTGGCTACA TGACATCAAC CATATCAGCA AAAGTGATAC GGGTATTATT TTTGCCGCTA    4440
TTTCTCTGTT CTCGCTATTA TTCCAACCGC TGTTTGGTCT GCTTTCTGAC AAACTCGGCC    4500
TCGACTCTAG GCGGCCGCGG GGATCCAGAC ATGATAAGAT ACATTGATGA GTTTGGACAA    4560
ACCACAACTA GAATGCAGTG AAAAAAATGC TTTATTTGTG AAATTTGTGA TGCTATTGCT    4620
TTATTTGTAA CCATTATAAG CTGCAATAAA CAAGTTAACA ACAACAATTG CATTCATTTT    4680
ATGTTTCAGG TTCAGGGGGA GGTGTGGGAG GTTTTTTCGG ATCCTCTAGA GTCGACCTGC    4740
AGGGGCTAGA ATGGCTACGT AGATAAGTAG CATGGCGGGT TAATCATTAA CTACAAGGAA    4800
CCCCTAGTGA TGGAGTTGGC CACTCCCTCT CTGCGCGCTC GCTCGCTCAC TGAGGCCGGG    4860
CGACCAAAGG TCGCCCGACG CCCGGGCTTT GCCCGGGCGG CCTCAGTGAG CGAGCGAGCG    4920
CGCAGCTGGC GTAATAGCGA AGAGGCCCGC ACCGATCGCC CTTCCCAACA GTTGCGCAGC    4980
CTGAATGGCG AATGGAATTC CAGACGATTG AGCGTCAAAA TGTAGGTATT TCCATGAGCG    5040
TTTTTCCTGT TGCAATGGCT GGCGGTAATA TTGTTCTGGA TATTACCAGC AAGGCCGATA    5100
GTTTGAGTTC TTCTACTCAG GCAAGTGATG TTATTACTAA TCAAAGAAGT ATTGCGACAA    5160
```

FIGURE 10D

```
CGGTTAATTT GCGTGATGGA CAGACTCTTT TACTCGGTGG CCTCACTGAT TATAAAAACA    5220
CTTCTCAGGA TTCTGGCGTA CCGTTCCTGT CTAAAATCCC TTTAATCGGC CTCCTGTTTA    5280
GCTCCCGCTC TGATTCTAAC GAGGAAAGCA CGTTATACGT GCTCGTCAAA GCAACCATAG    5340
TACGCGCCCT GTAGCGGCGC ATTAAGCGCG GCGGGTGTGG TGGTTACGCG CAGCGTGACC    5400
GCTACACTTG CCAGCGCCCT AGCGCCCGCT CCTTTCGCTT TCTTCCCTTC CTTTCTCGCC    5460
ACGTTCGCCG GCTTTCCCCG TCAAGCTCTA AATCGGGGC  TCCCTTTAGG GTTCCGATTT    5520
AGTGCTTTAC GGCACCTCGA CCCCAAAAAA CTTGATTAGG GTGATGGTTC ACGTAGTGGG    5580
CCATCGCCCT GATAGACGGT TTTTCGCCCT TGACGTTGG  AGTCCACGTT CTTTAATAGT    5640
GGACTCTTGT TCCAAACTGG AACAACACTC AACCCTATCT CGGTCTATTC TTTTGATTTA    5700
TAAGGGATTT TGCCGATTTC GGCCTATTGG TTAAAAAATG AGCTGATTTA ACAAAAATTT    5760
AACGCGAATT TTAACAAAAT ATTAACGTTT ACAATTTAAA TATTTGCTTA TACAATCTTC    5820
CTGTTTTTGG GGCTTTTCTG ATTATCAACC GGGGTACATA TGATTGACAT GCTAGTTTTA    5880
CGATTACCGT TCATCGATTC TCTTGTTTGC TCCAGACTCT CAGGCAATGA CCTGATAGCC    5940
TTTGTAGAGA CCTCTCAAAA ATAGCTACCC TCTCCGGCAT GAATTTATCA GCTAGAACGG    6000
TTGAATATCA TATTGATGGT GATTTGACTG TCTCCGGCCT TTCTCACCCG TTTGAATCTT    6060
TACCTACACA TTACTCAGGC ATTGCATTTA AAATATATGA GGGTTCTAAA AATTTTTATC    6120
CTTGCGTTGA AATAAAGGCT TCTCCCGCAA AAGTATTACA GGGTCATAAT GTTTTTGGTA    6180
CAACCGATTT AGCTTTATGC TCTGAGGCTT TATTGCTTAA TTTTGCTAAT TCTTTGCCTT    6240
GCCTGTATGA TTTATTGGAT GTTGGAATTC CTGATGCGGT ATTTTCTCCT TACGCATCTG    6300
TGCGGTATTT CACACCGCAT ATGGTGCACT CTCAGTACAA TCTGCTCTGA TGCCGCATAG    6360
TTAAGCCAGC CCCGACACCC GCCAACACCC GCTGACGCGC CCTGACGGGC TTGTCTGCTC    6420
CCGGCATCCG CTTACAGACA AGCTGTGACC GTCTCCGGGA GCTGCATGTG TCAGAGGTTT    6480
TCACCGTCAT CACCGAAACG CGCGAGACGA AAGGGCCTCG TGATACGCCT ATTTTTATAG    6540
GTTAATGTCA TGATAATAAT GGTTTCTTAG ACGTCAGGTG GCACTTTTCG GGGAAATGTG    6600
CGCGGAACCC CTATTTGTTT ATTTTTCTAA ATACATTCAA ATATGTATCC GCTCATGAGA    6660
CAATAACCCT GATAAATGCT TCAATAATAT TGAAAAAGGA AGAGTATGAG TATTCAACAT    6720
TTCCGTGTCG CCCTTATTCC CTTTTTTGCG GCATTTTGCC TTCCTGTTTT TGCTCACCCA    6780
GAAACGCTGG TGAAAGTAAA AGATGCTGAA GATCAGTTGG GTGCACGAGT GGGTTACATC    6840
GAACTGGATC TCAACAGCGG TAAGATCCTT GAGAGTTTTC GCCCCGAAGA ACGTTTTCCA    6900
```

FIGURE 10E

```
ATGATGAGCA CTTTTAAAGT TCTGCTATGT GGCGCGGTAT TATCCCGTAT TGACGCCGGG    6960
CAAGAGCAAC TCGGTCGCCG CATACACTAT TCTCAGAATG ACTTGGTTGA GTACTCACCA    7020
GTCACAGAAA AGCATCTTAC GGATGGCATG ACAGTAAGAG AATTATGCAG TGCTGCCATA    7080
ACCATGAGTG ATAACACTGC GGCCAACTTA CTTCTGACAA CGATCGGAGG ACCGAAGGAG    7140
CTAACCGCTT TTTTGCACAA CATGGGGGAT CATGTAACTC GCCTTGATCG TTGGGAACCG    7200
GAGCTGAATG AAGCCATACC AAACGACGAG CGTGACACCA CGATGCCTGT AGCAATGGCA    7260
ACAACGTTGC GCAAACTATT AACTGGCGAA CTACTTACTC TAGCTTCCCG GCAACAATTA    7320
ATAGACTGGA TGGAGGCGGA TAAAGTTGCA GGACCACTTC TGCGCTCGGC CCTTCCGGCT    7380
GGCTGGTTTA TTGCTGATAA ATCTGGAGCC GGTGAGCGTG GGTCTCGCGG TATCATTGCA    7440
GCACTGGGGC CAGATGGTAA GCCCTCCCGT ATCGTAGTTA TCTACACGAC GGGGAGTCAG    7500
GCAACTATGG ATGAACGAAA TAGACAGATC GCTGAGATAG GTGCCTCACT GATTAAGCAT    7560
TGGTAACTGT CAGACCAAGT TTACTCATAT ATACTTTAGA TTGATTTAAA ACTTCATTTT    7620
TAATTTAAAA GGATCTAGGT GAAGATCCTT TTTGATAATC TCATGACCAA AATCCCTTAA    7680
CGTGAGTTTT CGTTCCACTG AGCGTCAGAC CCCGTAGAAA AGATCAAAGG ATCTTCTTGA    7740
GATCCTTTTT TTCTGCGCGT AATCTGCTGC TTGCAAACAA AAAAACCACC GCTACCAGCG    7800
GTGGTTTGTT TGCCGGATCA AGAGCTACCA ACTCTTTTTC CGAAGGTAAC TGGCTTCAGC    7860
AGAGCGCAGA TACCAAATAC TGTCCTTCTA GTGTAGCCGT AGTTAGGCCA CCACTTCAAG    7920
AACTCTGTAG CACCGCCTAC ATACCTCGCT CTGCTAATCC TGTTACCAGT GGCTGCTGCC    7980
AGTGGCGATA AGTCGTGTCT TACCGGGTTG GACTCAAGAC GATAGTTACC GGATAAGGCG    8040
CAGCGGTCGG GCTGAACGGG GGGTTCGTGC ACACAGCCCA GCTTGGAGCG AACGACCTAC    8100
ACCGAACTGA GATACCTACA GCGTGAGCTA TGAGAAAGCG CCACGCTTCC CGAAGGGAGA    8160
AAGGCGGACA GGTATCCGGT AAGCGGCAGG GTCGGAACAG GAGAGCGCAC GAGGGAGCTT    8220
CCAGGGGGAA ACGCCTGGTA TCTTTATAGT CCTGTCGGGT TTCGCCACCT CTGACTTGAG    8280
CGTCGATTTT TGTGATGCTC GTCAGGGGGG CGGAGCCTAT GGAAAAACGC CAGCAACGCG    8340
GCCTTTTTAC GGTTCCTGGC CTTTTGCTGG CCTTTTGCTC ACATGTTCTT TCCTGCGTTA    8400
TCCCCTGATT CTGTGGATAA CCGTATTACC GCCTTTGAGT GAGCTGATAC CGCTCGCCGC    8460
AGCCGAACGA CCGAGCGCAG CGAGTCAGTG AGCGAGGAAG CGGAAGAGC               8509
```

FIGURE 12A

| | | | | | |
|---|---|---|---|---|---|
| GCCCAATACG | CAAACCGCCT | CTCCCCGCGC | GTTGGCCGAT | TCATTAATGC | AGCTGCGCGC | 60
| TCGCTCGCTC | ACTGAGGCCG | CCCGGGCAAA | GCCCGGGCGT | CGGGCGACCT | TTGGTCGCCC | 120
| GGCCTCAGTG | AGCGAGCGAG | CGCGCAGAGA | GGGAGTGGCC | AACTCCATCA | CTAGGGGTTC | 180
| CTTGTAGTTA | ATGATTAACC | CGCCATGCTA | CTTATCTACA | TCATCGATGA | ATTCGAGCTT | 240
| GCATGCCTGC | AGGTCGTTAC | ATAACTTACG | GTAAATGGCC | CGCCTGGCTG | ACCGCCCAAC | 300
| GACCCCCGCC | CATTGACGTC | AATAATGACG | TATGTTCCCA | TAGTAACGCC | AATAGGGACT | 360
| TTCCATTGAC | GTCAATGGGT | GGAGTATTTA | CGGTAAACTG | CCCACTTGGC | AGTACATCAA | 420
| GTGTATCATA | TGCCAAGTAC | GCCCCCTATT | GACGTCAATG | ACGGTAAATG | GCCCGCCTGG | 480
| CATTATGCCC | AGTACATGAC | CTTATGGGAC | TTTCCTACTT | GGCAGTACAT | CTACGTATTA | 540
| GTCATCGCTA | TTACCATGGT | GATGCGGTTT | TGGCAGTACA | TCAATGGGCG | TGGATAGCGG | 600
| TTTGACTCAC | GGGGATTTCC | AAGTCTCCAC | CCCATTGACG | TCAATGGGAG | TTTGTTTTGG | 660
| CACCAAAATC | AACGGGACTT | TCCAAAATGT | CGTAACAACT | CCGCCCCATT | GACGCAAATG | 720
| GGCGGTAGGC | GTGTACGGTG | GGAGGTCTAT | ATAAGCAGAG | CTCGTTTAGT | GAACCGTCAG | 780
| ATCGCCTGGA | GACGCCATCC | ACGCTGTTTT | GACCTCCATA | GAAGACACCG | GGACCGATCC | 840
| AGCCTCCGGA | CTCTAGAGGA | TCCGGTACTC | GACCCGAGCT | CGGATCCACT | AGTAACGGCC | 900
| GCCAGTGTGC | TGGAATTCTG | CACTCCAGGC | TGCCCGGGTT | TGCATGCTGC | TGCTGCTGCT | 960
| GCTGCTGGGC | CTGAGGCTAC | AGCTCTCCCT | GGGCATCATC | CTAGTTGAGG | AGGAGAACCC | 1020
| GGACTTCTGG | AACCGCGAGG | CAGCCGAGGC | CCTGGGTGCC | GCCAAGAAGC | TGCAGCCTGC | 1080
| ACAGACAGCC | GCCAAGAACC | TCATCATCTT | CCTGGGCGAT | GGGATGGGGG | TGTCTACGGT | 1140
| GACAGCTGCC | AGGATCCTAA | AAGGGCAGAA | GAAGGACAAA | CTGGGGCCTG | AGATACCCCT | 1200
| GGCCATGGAC | CGCTTCCCAT | ATGTGGCTCT | GTCCAAGACA | TACAATGTAG | ACAAACATGT | 1260
| GCCAGACAGT | GGAGCCACAG | CCACGGCCTA | CCTGTGCGGG | GTCAAGGGCA | ACTTCCAGAC | 1320
| CATTGGCTTG | AGTGCAGCCG | CCCGCTTTAA | CCAGTGCAAC | ACGACACGCG | GCAACGAGGT | 1380
| CATCTCCGTG | ATGAATCGGG | CCAAGAAAGC | AGGGAAGTCA | GTGGGAGTGG | TAACCACCAC | 1440
| ACGAGTGCAG | CACGCCTCGC | CAGCCGGCAC | CTACGCCCAC | ACGGTGAACC | GCAACTGGTA | 1500
| CTCGGACGCC | GACGTGCCTG | CCTCGGCCCG | CCAGGAGGGG | TGCCAGGACA | TCGCTACGCA | 1560
| GCTCATCTCC | AACATGGACA | TTGATGTGAT | CCTAGGTGGA | GGCCGAAAGT | ACATGTTTCG | 1620
| CATGGGAACC | CCAGACCCTG | AGTACCCAGA | TGACTACAGC | CAAGGTGGGA | CCAGGCTGGA | 1680
| CGGGAAGAAT | CTGGTGCAGG | AATGGCTCGG | CGAACGCCAG | GGTGCCCGGT | ACGTGTGGAA | 1740

FIGURE 12B

```
CCGCACTGAG CTCATGCAGG CTTCCCTGGA CCCGTCTGTG ACCCATCTCA TGGGTCTCTT    1800
TGAGCCTGGA GACATGAAAT ACGAGATCCA CCGAGACTCC ACACTGGACC CCTCCCTGAT    1860
GGAGATGACA GAGGCTGCCC TGCGCCTGCT GAGCAGACAC CCCCGCGGCT TCTTCCTCTT    1920
CGTGGAGGGT GGTCGCATCG ACCATGGTCA TCATGAAAGC AGGGCTTACC GGGCACTGAC    1980
TGAGACGATC ATGTTCGACG ACGCCATTGA GAGGGCGGGC CAGCTCACCA GCGAGGAGGA    2040
CACGCTGAGC CTCGTCACTG CCGACCACTC CCACGTCTTC TCCTTCGGAG GCTACCCCCT    2100
GCGAGGGAGC TCCTTCATCG GGCTGGCCGC TGGCAAGGCC CGGGACAGGA AGGCCTACAC    2160
GGTCCTCCTA TACGGAAACG GTCCAGGCTA TGTGCTCAAG GACGGCGCCC GGCCGGATGT    2220
TACCGAGAGC GAGAGCGGGA GCCCCGAGTA TCGGCAGCAG TCAGCAGTGC CCCTGGACGA    2280
AGAGACCCAC GCAGGCGAGG ACGTGGCGGT GTTCGCGCGC GGCCCGCAGG CGCACCTGGT    2340
TCACGGCGTG CAGGAGCAGA CCTTCATAGC GCACGTCATG GCCTTCGCCG CCTGCCTGGA    2400
GCCCTACACC GCCTGCGACC TGGCGCCCCC CGCCGGCACC ACCGACGCCG CGCACCCGGG    2460
GCGGTCCGTG GTCCCCGCGT TGCTTCCTCT GCTGGCCGGG ACCCTGCTGC TGCTGGAGAC    2520
GGCCACTGCT CCCTGAGTGT CCCGTCCCTG GGGCTCCTGC TTCCCCATCC CGGAGTTCTC    2580
CTGCTCCCCA CCTCCTGTCG TCCTGCCTGG CCTCCAGCCC GAGTCGTCAT CCCCGGAGTC    2640
CCTATACAGA GGTCCTGCCA TGGAACCTTC CCCTCCCCGT GCGCTCTGGG GACTGAGCCC    2700
ATGACACCAA ACCTGCCCCT TGGCTGCTCT CGGACTCCCT ACCCCAACCC CAGGGACTGC    2760
AGGTTGTGCC CTGTGGCTGC CTGCACCCCA GGAAAGGAGG GGGCTCAGGC CATCCAGCCA    2820
CCACCTACAG CCCAGTGGGG TCGAGACAGA TGGTCAGTCT GGAGGATGAC GTGGCGTGAA    2880
GCTGGCCGCG GGGATCCAGA CATGATAAGA TACATTGATG AGTTTGGACA AACCACAACT    2940
AGAATGCAGT GAAAAAAATG CTTTATTTGT GAAATTTGTG ATGCTATTGC TTTATTTGTA    3000
ACCATTATAA GCTGCAATAA ACAAGTTAAC AACAACAATT GCATTCATTT TATGTTTCAG    3060
GTTCAGGGGG AGGTGTGGGA GGTTTTTTCG GATCCTCTAG AGTCGACTCT AGANNNNNNN    3120
NNNNNNNNNN NNNNNNNNNN NNNNNNNNNN NNNNNNNNNN NNNNNNNNNN NNNNNNNNNN    3180
NNNNNNNNNN NNNNNNNNNN NNNNNNNNNN NNNNNNNNNN NNNNNNNNNN NNNNNNNNNN    3240
NNNNNNNNNN NNNNNNNNNN NNNNNNNNNN NNNNNNNNNN NNNNNNNNNN NNNNNNNNNN    3300
NNNNNNNNNN NNNNNNNNNN NNNNNNNNNN NNNNNNNNNN NNNNNNNNNN NNNNNNNNNN    3360
NNNNNNNNNN NNNNNNNNNN NNNNNNNNNN NNNGGATCCC CATGACTACG TCCGGCGTTC    3420
```

FIGURE 12C

```
CATTTGGCAT GACACTACGA CCAACACGAT CTCGGTTGTC TCGGCGCACT CCGTACAGTA    3480
GGGATCGTCT ACCTCCTTTT GAGACAGAAA CCCGCGCTAC CATACTGGAG GATCATCCGC    3540
TGCTGCCCGA ATGTAACACT TTGACAATGC ACAACGTGAG TTACGTGCGA GGTCTTCCCT    3600
GCAGTGTGGG ATTTACGCTG ATTCAGGAAT GGGTTGTTCC CTGGGATATG GTTCTAACGC    3660
GGGAGGAGCT TGTAATCCTG AGGAAGTGTA TGCACGTGTG CCTGTGTTGT GCCAACATTG    3720
ATATCATGAC GAGCATGATG ATCCATGGTT ACGAGTCCTG GGCTCTCCAC TGTCATTGTT    3780
CCAGTCCCGG TTCCCTGCAG TGTATAGCCG GCGGGCAGGT TTTGGCCAGC TGGTTTAGGA    3840
TGGTGGTGGA TGGCGCCATG TTTAATCAGA GGTTTATATG GTACCGGGAG GTGGTGAATT    3900
ACAACATGCC AAAAGAGGTA ATGTTTATGT CCAGCGTGTT TATGAGGGGT CGCCACTTAA    3960
TCTACCTGCG CTTGTGGTAT GATGGCCACG TGGGTTCTGT GGTCCCCGCC ATGAGCTTTG    4020
GATACAGCGC CTTGCACTGT GGGATTTTGA ACAATATTGT GGTGCTGTGC TGCAGTTACT    4080
GTGCTGATTT AAGTGAGATC AGGGTGCGCT GCTGTGCCCG GAGGACAAGG CGCCTTATGC    4140
TGCGGGCGGT GCGAATCATC GCTGAGGAGA CCACTGCCAT GTTGTATTCC TGCAGGACGG    4200
AGCGGCGGCG GCAGCAGTTT ATTCGCGCGC TGCTGCAGCA CCACCGCCCT ATCCTGATGC    4260
ACGATTATGA CTCTACCCCC ATGTAGGGAT CCCCATCACT AGTGCGGCCG CGGGGATCCA    4320
GACATGATAA GATACATTGA TGAGTTTGGA CAAACCACAA CTAGAATGCA GTGAAAAAAA    4380
TGCTTTATTT GTGAAATTTG TGATGCTATT GCTTATTTG TAACCATTAT AAGCTGCAAT    4440
AAACAAGTTA ACAACAACAA TTGCATTCAT TTTATGTTTC AGGTTCAGGG GGAGGTGTGG    4500
GAGGTTTTTT CGGATCCTCT AGAGTCGACC TGCAGGCATG CAAGCTGTAG ATAAGTAGCA    4560
TGGCGGGTTA ATCATTAACT ACAAGGAACC CCTAGTGATG GAGTTGGCCA CTCCCTCTCT    4620
GCGCGCTCGC TCGCTCACTG AGGCCGGGCG ACCAAGGTC GCCCGACGCC CGGGCTTTGC    4680
CCGGGCGGCC TCAGTGAGCG AGCGAGCGCG CAGCTGGCGT AATAGCGAAG AGGCCCGCAC    4740
CGATCGCCCT TCCCAACAGT TGCGCAGCCT GAATGGCGAA TGGAANTTCC AGACGATTGA    4800
GCGTCAAAAT GTAGGTATTT CCATGAGCGT TTTTCCTGTT GCAATGGCTG GCGGTAATAT    4860
TGTTCTGGAT ATTACCAGCA AGGCCGATAG TTTGAGTTCT TCTACTCAGG CAAGTGATGT    4920
TATTACTAAT CAAAGAAGTA TTGCGACAAC GGTTAATTTG CGTGATGGAC AGACTCTTTT    4980
ACTCGGTGGC CTCACTGATT ATAAAAACAC TTCTCAGGAT TCTGGCGTAC CGTTCCTGTC    5040
TAAAATCCCT TTAATCGGCC TCCTGTTTAG CTCCCGCTCT GATTCTAACG AGGAAAGCAC    5100
```

FIGURE 12D

```
GTTATACGTG CTCGTCAAAG CAACCATAGT ACGCGCCCTG TAGCGGCGCA TTAAGCGCGG    5160
CGGGTGTGGT GGTTACGCGC AGCGTGACCG CTACACTTGC CAGCGCCCTA GCGCCCGCTC    5220
CTTTCGCTTT CTTCCCTTCC TTTCTCGCCA CGTTCGCCGG CTTTCCCCGT CAAGCTCTAA    5280
ATCGGGGGCT CCCTTTAGGG TTCCGATTTA GTGCTTTACG GCACCTCGAC CCCAAAAAAC    5340
TTGATTAGGG TGATGGTTCA CGTAGTGGGC CATCGCCCTG ATAGACGGTT TTTCGCCCTT    5400
TGACGTTGGA GTCCACGTTC TTTAATAGTG GACTCTTGTT CCAAACTGGA ACAACACTCA    5460
ACCCTATCTC GGTCTATTCT TTTGATTTAT AAGGGATTTT GCCGATTTCG GCCTATTGGT    5520
TAAAAAATGA GCTGATTTAA CAAAAATTTA ACGCGAATTT TAACAAAATA TTAACGTTTA    5580
CAATTTAAAT ATTTGCTTAT ACAATCTTCC TGTTTTGGG GCTTTTCTGA TTATCAACCG    5640
GGGTACATAT GATTGACATG CTAGTTTTAC GATTACCGTT CATCGATTCT CTTGTTTGCT    5700
CCAGACTCTC AGGCAATGAC CTGATAGCCT TTGTAGAGAC CTCTCAAAAA TAGCTACCCT    5760
CTCCGGCATG AATTTATCAG CTAGAACGGT TGAATATCAT ATTGATGGTG ATTTGACTGT    5820
CTCCGGCCTT TCTCACCCGT TTGAATCTTT ACCTACACAT TACTCAGGCA TTGCATTTAA    5880
AATATATGAG GGTTCTAAAA ATTTTTATCC TTGCGTTGAA ATAAAGGCTT CTCCCGCAAA    5940
AGTATTACAG GGTCATAATG TTTTTGGTAC AACCGATTTA GCTTTATGCT CTGAGGCTTT    6000
ATTGCTTAAT TTTGCTAATT CTTTGCCTTG CCTGTATGAT TTATTGGATG TTGGAANTTC    6060
CTGATGCGGT ATTTTCTCCT TACGCATCTG TGCGGTATTT CACACCGCAT ATGGTGCACT    6120
CTCAGTACAA TCTGCTCTGA TGCCGCATAG TTAAGCCAGC CCGACACCC GCCAACACCC    6180
GCTGACGCGC CCTGACGGGC TTGTCTGCTC CCGGCATCCG CTTACAGACA AGCTGTGACC    6240
GTCTCCGGGA GCTGCATGTG TCAGAGGTTT TCACCGTCAT CACCGAAACG CGCGAGACGA    6300
AAGGGCCTCG TGATACGCCT ATTTTTATAG GTTAATGTCA TGATAATAAT GGTTTCTTAG    6360
ACGTCAGGTG GCACTTTTCG GGGAAATGTG CGCGGAACCC CTATTTGTTT ATTTTTCTAA    6420
ATACATTCAA ATATGTATCC GCTCATGAGA CAATAACCCT GATAAATGCT TCAATAATAT    6480
TGAAAAAGGA AGAGTATGAG TATTCAACAT TTCCGTGTCG CCCTTATTCC CTTTTTTGCG    6540
GCATTTTGCC TTCCTGTTTT TGCTCACCCA GAAACGCTGG TGAAAGTAAA AGATGCTGAA    6600
GATCAGTTGG GTGCACGAGT GGGTTACATC GAACTGGATC TCAACAGCGG TAAGATCCTT    6660
GAGAGTTTTC GCCCCGAAGA ACGTTTTCCA ATGATGAGCA CTTTTAAAGT TCTGCTATGT    6720
GGCGCGGTAT TATCCCGTAT TGACGCCGGG CAAGAGCAAC TCGGTCGCCG CATACACTAT    6780
```

FIGURE 12E

```
TCTCAGAATG ACTTGGTTGA GTACTCACCA GTCACAGAAA AGCATCTTAC GGATGGCATG    6840
ACAGTAAGAG AATTATGCAG TGCTGCCATA ACCATGAGTG ATAACACTGC GGCCAACTTA    6900
CTTCTGACAA CGATCGGAGG ACCGAAGGAG CTAACCGCTT TTTTGCACAA CATGGGGGAT    6960
CATGTAACTC GCCTTGATCG TTGGGAACCG GAGCTGAATG AAGCCATACC AAACGACGAG    7020
CGTGACACCA CGATGCCTGT AGCAATGGCA ACAACGTTGC GCAAACTATT AACTGGCGAA    7080
CTACTTACTC TAGCTTCCCG GCAACAATTA ATAGACTGGA TGGAGGCGGA TAAAGTTGCA    7140
GGACCACTTC TGCGCTCGGC CCTTCCGGCT GGCTGGTTTA TTGCTGATAA ATCTGGAGCC    7200
GGTGAGCGTG GGTCTCGCGG TATCATTGCA GCACTGGGGC CAGATGGTAA GCCCTCCCGT    7260
ATCGTAGTTA TCTACACGAC GGGGAGTCAG GCAACTATGG ATGAACGAAA TAGACAGATC    7320
GCTGAGATAG GTGCCTCACT GATTAAGCAT TGGTAACTGT CAGACCAAGT TTACTCATAT    7380
ATACTTTAGA TTGATTTAAA ACTTCATTTT TAATTTAAAA GGATCTAGGT GAAGATCCTT    7440
TTTGATAATC TCATGACCAA AATCCCTTAA CGTGAGTTTT CGTTCCACTG AGCGTCAGAC    7500
CCCGTAGAAA AGATCAAAGG ATCTTCTTGA GATCCTTTTT TTCTGCGCGT AATCTGCTGC    7560
TTGCAAACAA AAAAACCACC GCTACCAGCG GTGGTTTGTT TGCCGGATCA AGAGCTACCA    7620
ACTCTTTTTC CGAAGGTAAC TGGCTTCAGC AGAGCGCAGA TACCAAATAC TGTCCTTCTA    7680
GTGTAGCCGT AGTTAGGCCA CCACTTCAAG AACTCTGTAG CACCGCCTAC ATACCTCGCT    7740
CTGCTAATCC TGTTACCAGT GGCTGCTGCC AGTGGCGATA AGTCGTGTCT TACCGGGTTG    7800
GACTCAAGAC GATAGTTACC GGATAAGGCG CAGCGGTCGG GCTGAACGGG GGGTTCGTGC    7860
ACACAGCCCA GCTTGGAGCG AACGACCTAC ACCGAACTGA GATACCTACA GCGTGAGCTA    7920
TGAGAAAGCG CCACGCTTCC CGAAGGGAGA AAGGCGGACA GGTATCCGGT AAGCGGCAGG    7980
GTCGGAACAG GAGAGCGCAC GAGGGAGCTT CCAGGGGGAA ACGCCTGGTA TCTTTATAGT    8040
CCTGTCGGGT TTCGCCACCT CTGACTTGAG CGTCGATTTT TGTGATGCTC GTCAGGGGG    8100
CGGAGCCTAT GGAAAAACGC CAGCAACGCG GCCTTTTTAC GGTTCCTGGC CTTTTGCTGG    8160
CCTTTTGCTC ACATGTTCTT TCCTGCGTTA TCCCCTGATT CTGTGGATAA CCGTATTACC    8220
GCCTTTGAGT GAGCTGATAC CGCTCGCCGC AGCCGAACGA CCGAGCGCAG CGAGTCAGTG    8280
AGCGAGGAAG CGGAAGAGC                                                8299
```

METHOD FOR IMPROVED PRODUCTION OF RECOMBINANT ADENO-ASSOCIATED VIRUSES FOR GENE THERAPY

This invention was supported by the National Institutes of Health Grant No. DK47757. The United States government has certain rights in this invention.

FIELD OF THE INVENTION

The present invention relates generally to gene therapy, and more specifically, to methods of providing more efficient transduction of gene therapy vehicles.

BACKGROUND OF THE INVENTION

Adeno-associated virus (AAV) is an integrating human DNA parvovirus which has been proposed for use as a gene delivery vehicle for somatic gene therapy. This small non-enveloped virus contains a 4.6 kb single stranded DNA genome that encodes sets of regulatory and capsid genes called rep and cap. Rep polypeptides (rep78, rep68, rep62 and rep40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures.

The life cycle of AAV is characterized by both lytic and latent components [B. J. Carter, in "Handbook of Parvoviruses", ed., P. Tijsser, CRC Press, pp.155–168 (1990)]. During a latent infection, AAV virions enter a cell as an encapsidated single stranded (ss) DNA, and shortly thereafter are delivered to the nucleus where the AAV DNA stably integrates into a host chromosome without the apparent need for host cell division. In the absence of helper virus, the integrated ss DNA AAV genome remains latent but capable of being activated and rescued.

The lytic phase of the life cycle begins when a cell harboring an AAV provirus is challenged with a secondary infection by a herpesvirus or adenovirus which encodes helper functions that are recruited by AAV to aid in its excision from host chromatin [B. J. Carter, cited above]. The infecting parental ssDNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either + or − ss DNA genomes following cell lysis.

Recombinant forms of AAV (rAAV) have been developed as vectors by replacing all viral open reading frames with a therapeutic minigene, while retaining the necessary cis elements contained in the ITRs. [See, e.g., U.S. Pat. Nos. 4,797,368; 5,153,414; 5,139,941; 5,252,479; and 5,354,678; and International Publication Nos. WO91/18088 published Nov. 28, 1991; WO93/24641 published Dec. 9, 1993 and WO94/13788 published Jun. 23, 1994]. However, progress towards establishing AAV as a transducing vehicle for gene therapy has been slow for a variety of reasons. For example, the integrated provirus preferentially targets specific sites in chromosome 19. Additionally, difficulties surround large-scale production of replication defective recombinants. The cells employed to produce rAAV must also be infected with adenovirus or herpesvirus to provide the necessary helper functions, thereby producing problems in purifying recombinant AAV (rAAV) from contaminating virus in culture.

AAV mediated transduction with a recombinant virus is a poorly understood process that has been compared to the latent phase of the wild type AAV life cycle. Transduction with rAAV has been demonstrated in a wide variety of cell types including differentiated, non-dividing cells, suggesting the potential of this vector system for in vivo gene delivery to organs such as muscle, liver, central nervous system and lung.

Features of the lytic phase of the wild type virus are of potential importance to both the production of the recombinant as well as its interaction with the recipient cell during transduction. When a cell harboring an integrated AAV provirus is challenged with a secondary infection by adenovirus or herpesvirus, a series of events unfold that result in cell lysis and propagation of AAV. Helper viruses encode functions that, along with products from cellular genes, are recruited by AAV to aid in rescue of the viral genome from the chromosome. Virus helper activities act to enhance or regulate AAV and cellular gene expression, while cellular proteins/factors direct replication of the rescued AAV genome.

Despite a wealth of literature describing use of AAV as a gene therapy vehicle, practical experience with purified recombinant AAV as a gene therapy vector has been disappointing, because the more purified the AAV is from co-infection with its helper virus in culture, the lower the gene transduction efficiencies that the rAAV displays.

There thus remains a need in the art for methods and compositions which enable efficient use of rAAV vehicles for gene therapy.

SUMMARY OF THE INVENTION

In one aspect, the invention provides a method for enhancing the efficiency of transduction of a recombinant AAV into a target cell. The method operates, in brief, by infecting a target cell with a single stranded recombinant adeno-associated virus (rAAV) which comprises a transgene operatively linked to regulatory sequences directing its expression, and contacting the infected cells with an agent which facilitates the conversion of ss rAAV to its double stranded (ds) form. Conversion of ss rAAV to ds rAAV occurs in the target cell, resulting in enhanced transduction of the recombinant virus into the target cell. The agent may be a helper virus which carries a selected gene or functional fragment thereof encoding a polypeptide capable of enhancing the conversion of the ss rAAV to ds rAAV and which is co-infected into the same target cell. The agent may also be a drug or chemical composition which accomplishes the same function and is applied to the infected target cell. This method can operate both in an ex vivo setting and in vivo.

In another aspect, the invention provides a novel recombinant AAV, which contains both the transgene intended for use in treating a genetic disease or disorder and a second gene operatively linked to inducible or constitutive regulatory sequences, the second gene encoding a polypeptide capable of facilitating the conversion of ss rAAV to its ds form upon expression. In a preferred embodiment, the second gene is adenovirus E4 or a functional fragment thereof.

The novel rAAV described above is thus useful in another aspect of the invention, i.e., a method for enhancing the efficiency of transduction of the novel rAAV into a target cell. The method operates, in brief, by infecting a target cell with the novel ss rAAV, either ex vivo or in vivo. Where the regulatory sequences controlling expression of the second gene are constitutive, the polypeptide which facilitates conversion of the rAAV from ss to ds is produced by normal operation of the infected target cells machinery.

Alternatively, where the regulatory sequences controlling expression of the second gene are inducible, the polypeptide which facilitates conversion of the rAAV from ss to ds is produced by contacting the infected cell with a suitable inducing agent, ex vivo or in vivo.

Still other novel rAAV and methods of this invention involve two genes in addition to the therapeutic transgene, which in concert facilitate the ss to ds rAAV conversion in an infected target cell.

The novel rAAV and methods of this invention are also useful in ex vivo and in vivo gene therapy treatment protocols and therapeutic compositions for treating inherited diseases, cancer, and other genetic dysfunctions.

Other aspects and advantages of the present invention are described further in the following detailed description of the preferred embodiments thereof.

BRIEF DESCRIPTION OF THE DRAWINGS

FIG. 4A is a flow chart illustrating a model for leading strand synthesis of a complementary AAV strand in the presence of Rep (+Rep) or absence of Rep (−Rep). Rep expresses a terminal resolution activity that can convert a duplex structure with closed-ends to an open-ended duplex. In the absence of Rep, terminal resolution is impaired leaving the covalently closed, hairpin structures intact. Under these conditions, hairpins are expected to be found leftward and rightward, since both strands of a rescued double-stranded AAV genome are packaged into virions.

FIG. 4B is a schematic of linear AV.CMVLacZ with labeled domains including the AAV inverted terminal repeats (ITR), cytomegalovirus immediate early enhancer/promoter (CMV), SV40 splice donor-splice acceptor (SD/SA), $E.$ $coli$ b-galactosidase cDNA (LacZ), and SV40 polyadenylation signal (pA). Two NotI sites located at bp positions 1035 and 4509 are indicated.

FIG. 4C illustrates a closed end and an open end fragment of rAV.CMVLacZ.

FIGS. 4D, 4E and 4F indicate the mixture of open-ended and covalently closed duplex fragments generated by NotI digestion of ss AV.CMVLacZ at position 4509 in the absence of terminal resolution. The NotI 4509 digestion provides a convenient means of releasing a 361 bp fragment that contains the right ITR in the context of a hybridization target (i.e. SV40 pA). In the presence of terminal resolution, only the open-ended 361 bp fragment would be expected to be generated (FIG. 4D) by such digestion.

FIG. 4G is an electrophoretic gel, which in lane (1) indicates the results of digestion of a plasmid carrying an AV.CMVLacZ cDNA to release the rAAV and subsequent digestion with NotI to release the right terminal 361 bp fragment. In lane (2) a sample of NotI digested Hirt DNA extracted from HeLa cells infected with wild-type Ad5 and transduced with AV.CMVLacZ resulted in the release of two fragments, labeled FormI and FormII. The migration of single-stranded AV.CMVLacZ (SS) and RFm are also shown.

FIG. 10 is the DNA sequence [SEQ ID NO: 1] of the plasmid pAV.CMVLacZ. The AAV 5' ITR is at nucleotides 53–219; the CMV enhancer/promoter is at nucleotides 246–839; the SV40 intron is at nucleotides 856–987; the LacZ cDNA is at nucleotides 1039–4512; the SV40 polyadenylation signal is at nucleotides 4522–4719; and the 3' AAV ITR is at nucleotides 4759–4925. All other nucleotides are plasmid derived.

FIG. 12 is the DNA sequence [SEQ ID NO: 2] of the plasmid pAV.CMVALP.GRE-ORF6, which in turn generates a novel rAAV containing the LacZ transgene and the Ad E4 ORF 6 which facilitates ss to ds conversion of rAAV. The AAV 5' ITR is at nucleotides 53–219; the CMV enhancer/promoter is at nucleotides 255–848; the human placenta alkaline phosphatase cDNA (ALP) is at nucleotides 914–2892; the SV40 polyA signal is at nucleotides 2893–3090; the GRE promoter is at nucleotides 3114–3393; the Ad5 E4-ORF6 cDNA is at nucleotides 3402–4286; the SV40 polyadenylation signal is at nucleotides 4315–4512; and the 3' AAV ITR is at nucleotides 4547–4713. All other nucleotides are plasmid derived.

DETAILED DESCRIPTION OF THE INVENTION

Figure 1A:
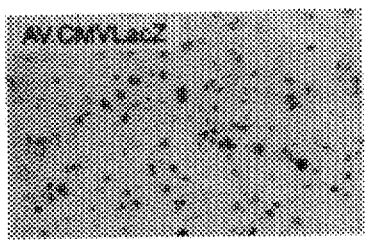
FIG. 1A is an photomicrograph of a histochemical stain for $E.$ $coli$ β-galactosidase (LacZ) activity in HeLa cells transfected with AV.CMVLacZ only. Magnification is 10×.
Figure 1B:
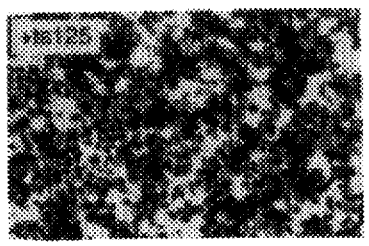
FIG. 1B is a similar photomicrograph in HeLa cells transfected with AV.CMVLacZ and Ad mutant ts125.
Figure 1C:
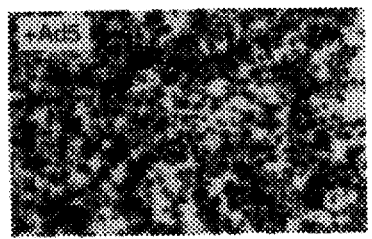
FIG. 1C is a similar photomicrograph in HeLa cells transfected with AV.CMVLacZ and wild type Ad5.
Figure 1D:
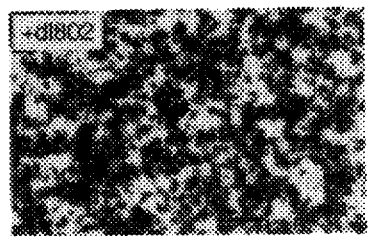
FIG. 1D is a similar photomicrograph in HeLa cells transfected with AV.CMVLacZ and Ad mutant dl802.
Figure 1E:
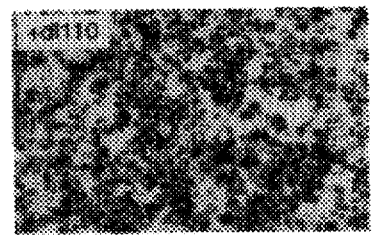
FIG. 1E is a similar photomicrograph in HeLa cells transfected with AV.CMVLacZ and Ad mutant dl110.

The present invention provides novel methods for enhancing the transduction efficiency of recombinant adeno-associated virus (rAAV) containing a transgene for expression in a somatic gene therapy protocol. The present invention also provides novel "second generation" recombinant AAV viruses and methods for enhancing the transduction efficiency of the novel recombinant viruses in the target cell. The methods and compositions of this invention are useful in ex vivo applications of gene therapy, such as in the transduction of bone marrow cells with desirable hematopoietic stem cell progenitor genes prior to bone marrow transplantation. The embodiments of the invention are also useful in direct in vivo treatment of patients by gene therapy vectors, including the transduction of desirable genes in patients with genetic disorders, such as cystic fibrosis.

For purposes of this invention, by the term "transgene" is meant a nucleic acid sequence or reverse transcript thereof, heterologous to the AAV sequence, which encodes a polypeptide or protein of interest. The transgene may be operatively linked to regulatory components in a manner which permits transgene transcription, i.e., the transgene is placed into operative association with a promoter, as well as other regulatory sequences, such as SV40 introns or polyA sequences, useful for its regulation. The composite association of the transgene with its regulatory sequences is referred to herein as a minicassette or minigene.

The composition of the transgene or minicassette sequence will depend upon the use to which the resulting rAAV will be put. For example, one type of transgene sequence includes a reporter sequence, which upon expression produces a detectable signal. Such reporter sequences include without limitation, an *E. coli* beta-galactosidase (LacZ) cDNA, an alkaline phosphatase gene (ALP) and a green fluorescent protein gene. These sequences, when associated with regulatory elements which drive their expression, provide signals detectable by conventional means, e.g., ultraviolet wavelength absorbance, visible color change, etc.

Another type of transgene sequence includes a therapeutic gene which expresses a desired gene product in a host cell. These therapeutic nucleic acid sequences typically encode products for administration and expression in a patient in vivo or ex vivo to replace or correct an inherited or non-inherited genetic defect or treat an epigenetic disorder or disease. Such transgenes may be readily selected by one of skill in this art and the design of the transgene or the minicassette for insertion into the rAAV is not a limitation of this invention.

The term "rAAV" as used herein encompasses any recombinant AAV gene therapy vehicle of the prior art, including the AdAAV hybrid virus described in copending Ser. No. 08/331,384, filed Oct. 28, 1994, incorporated by reference herein. More specifically, rAAV defines a recombinant adeno-associated virus comprising: (a) the DNA of, or corresponding to, at least a portion of the genome of an AAV which portion is capable of transducing into a target cell at least one selected gene in the absence of cell division; and (b) at least one selected gene (or transgene) operatively linked to regulatory sequences directing its expression, the gene flanked by the DNA of (a) and capable of expression in the target cell in vivo or in vitro. Other recombinant AAVs have been described in the art. The method of this invention is not limited by the precise nature of the AAV sequences used in the rAAV, provided that at a minimum both the 5' and 3' AAV inverted terminal repeats are present. Thus, the rAAV may be selected by one of skill in the art, and is not itself a limitation on this invention. The rAAVs specifically disclosed herein are illustrative.

By the term "transduction" is meant that the rAAV produced by practice of the invention is capable of infecting a desired target cell and expressing the transgene in the cell by harnessing the cell's machinery. Transduction may include stably integrating the viral DNA into a chromosome of the target cell. "Enhanced transduction" is defined as the ability of the rAAV to transduce the target cell, either in vitro or in vivo, at an efficiency greater than a typical prior art rAAV produced in, and purified from, a culture co-infected with an adenovirus or herpesvirus helper.

While not wishing to be bound by theory, the present invention is based on the observation that the limiting step in rAAV mediated transduction of cells for gene therapy is not the internalization or transfer of the single stranded viral genome, but rather the subsequent conversion of the single stranded viral genome to a transcriptionally active double stranded form. Formation of double stranded DNA intermediates is necessary for recombinant gene expression, which is likely to be modulated by viral and cellular factors through posttranscriptional mechanisms. The inventors have designed a method to overcome this rate-limiting step, thereby enhancing transduction ability of an rAAV and ultimately the use of rAAV in gene therapy protocols.

The method of the present invention may employ a conventionally prepared single-stranded rAAV containing a transgene. In contrast to the prior art, which produces ss rAAV by co-infection in culture with a helper adenovirus or herpesvirus, followed by purifying the rAAV from the culture contaminants including the helper virus, the present invention provides for infecting a target cell with a ss rAAV without prior exposure to a helper virus. Once the target cell is infected, the infected cell is contacted with an agent which facilitates the conversion of the ss rAAV to the double-stranded form of rAAV. The action of this "facilitating agent" or "conversion agent" causes the ss to ds conversion to occur in the target cell, resulting in enhanced transduction of the recombinant AAV into the target cell. By facilitating the conversion of ss to ds rAAV in the target cell, the method of this invention may also result in both transduction and stable chromosomal integration of the recombinant virus into the chromosome of said host cell.

Preferably, for use of this invention the "facilitating or conversion agent" may take several forms.

A. The Conversion Agent is a Helper Virus

In one embodiment, the agent is a helper virus and the method includes an additional step of co-infecting the target cell with the helper virus. The helper virus useful in this method contains a selected gene which can facilitate the conversion of single-stranded recombinant virus to double-stranded recombinant virus. The selected gene may encode a gene product or polypeptide (or a functional fragment of the polypeptide which shares the biological activity of the full-length polypeptide) which enhances the conversion. Alternatively, the selected gene may express an antisense or ribozyme which functions in the cell to block or inhibit a cellular gene that normally prevents ss to ds conversion of the rAAV. These genes may also be employed in the second generation rAAV described below.

The helper virus is capable of expressing the selected gene product in the target cell in the absence of cell division. The helper virus may be a wild-type or mutant adenovirus. The helper virus may alternatively be a wild-type or mutant herpesvirus. Preferably, for use as facilitating agents, such viruses are mutants deleted of several normal genes so that the helper viruses and/or their expressed gene products will not cause disease in a patient.

For example, a helper adenovirus useful in this invention may express only a gene product of a single adenoviral early gene. Exposure of the ss rAAV to an Ad early gene product is sufficient to substantially enhance the formation of double-stranded rAAV genome with a coordinate increase in transduction efficiency. The Ad early genes which are useful in producing this effect are E1, E2a, E4 and functional fragments thereof. However, as demonstrated by the examples below, adenovirus substantially enhances recombinant AAV transduction in vitro in a way that is dependent on expression of the E1 and E4 genes of adenovirus and is directly proportional to the appearance of double-stranded replicative forms of rAAV.

Thus, one example of a helper virus is an adenovirus deleted of most of its wild-type early genes and which is capable of expressing only its E4 gene or a functional fragment thereof in the target cell. Among such functional fragments is the open reading frame 6 of the E4 gene (nucleotides 3402 to 4286 of SEQ ID NO: 2). As described below in the examples, experiments in cell lines indicate that the ORF6 of the adenoviral E4 gene locus is sufficient to significantly enhance rAAV transduction. Selective expression of the E4-ORF6 product of adenovirus accomplishes a increase in transduction efficiency similar to, but somewhat attenuated, compared to that produced by exposure to the E1 and E4 gene products in combination. That is, the ORF6 product of E4 is sufficient to enhance the augmentation of rAAV transduction; but this effect is amplified substantially by E1 gene products.

Thus, more preferably, exposure of the rAAV to both the expressed E1 and E4 gene products produces a substantial enhancement of the above-described rate limiting step. Therefore, another exemplary helper virus may also contain more than one gene which, upon expression, facilitates the ss to ds conversion. An example of such a helper virus is an adenovirus which expresses both the E1 and E4 genes, or functional fragments thereof. Still other Ad genes may be expressed by the helper virus, provided that the virus is sufficiently crippled so that it does not cause disease in the patient contributing the target cells.

Where the agent which facilitates conversion of ss to ds rAAV is a helper virus, the method of the invention comprises co-infecting the target cell with the rAAV and the helper virus. Such co-infection may occur in the context of ex vivo therapy, i.e., manipulations performed on cells extracted from the patient, which cells are reinserted into the patient after the method is performed. Alternatively, the patient may be directly co-infected with the two viruses by conventional means. Delivery of the two viruses to the patient may be directed to a specific organ, or to the general circulatory system. Such delivery methods are described in the art for gene therapy of, e.g., cystic fibrosis [see, e.g., U.S. Pat. No. 5,240,846].

B. The Conversion Agent is a Chemical, Drug or Other Entity that can Activate rAAV Transduction In another embodiment of the method of this invention, the conversion agent which contacts the cells infected with the rAAV may be selected from the following classes of known compounds or methods: 1) inhibitors of DNA synthesis such as hydroxyurea, hydrogen peroxide, and other direct or indirect inhibitors of DNA polymerase; 2) chemotherapeutic agents that induce DNA damage, such as cyclophosphamide, alkylating agents, purine analogs, e.g., 6-thioguanine, etc.; 3) drugs that interfere with DNA modifying enzymes, such as inhibitors of topoisomerase, DNA ligase exonucleases and endonucleases; and 4) agents that nonspecifically enhance transcription, such as sodium butyrate, or agents that stabilize cells, such as DMSO. Also, genotoxic agents such as carcinogens may be employed as the conversion agent. Other methods of inducing disruption or damage to DNA may also be useful as agents capable of facilitating ss to ds conversion of rAAV and may be selected by one of skill in the art, including physical methods, such as irradiation. These classes of compounds or methods are believed to result in the conversion from ss to ds rAAV.

According to this embodiment of the method of the invention, the rAAV is again produced conventionally, but not co-infected with a helper virus. The ss rAAV is infected into the target cell, and the infected cell is contacted by the agent in an appropriate manner depending on the identity of the agent. These conversion enhancing agents can be employed in ex vivo treatment of the target cells infected by the rAAV by application directly to the cells. Such application can occur substantially simultaneously, or consecutively, with application of the rAAV gene therapy vehicle. For example, the infected target cell may be subjected to one of the above-listed compounds or drugs for a desired time period. The parameters for contacting the infected cells with the agent may readily be determined by one of skill in the art. These parameters will depend upon whether the method is performed ex vivo or in vivo. For example, the number of ex vivo infected cells to be treated will be considered for the dosage, and timing of such treatment.

Similarly, the physical status of the patient can determine the parameters of delivery of the agent to the patient in vivo. The dosage and amount of the damaging agent may therefore be adjusted by one of skill in the art. Where the agents are typical chemotherapeutic drugs approved for use in humans or animals, such enhanced conversion of rAAV may also occur in vivo by the co-administration of the agent, i.e., the chemotherapeutic drug, and the rAAV gene therapy vehicle to the patient. According to this aspect of the invention, the chemotherapeutic drug would be administered only when the rAAV is administered. Appropriate dosages and amounts of chemotherapeutic drugs and recombinant gene therapy vehicles and means for determining such amounts are within the skill of the art. However, because the effect of the chemotherapeutic drug will enhance the ss to ds conversion of the rAAV and thus enhance its efficiency of transduction into the target cells, it is anticipated that lower dosages than the conventional dosages of either or both the drug and the rAAV could be effectively administered.

C. The Conversion Agent May be Part of the rAAV.

In still another embodiment of this invention, a novel "second generation" rAAV may be designed to incorporate the conversion agent into the virus, so that both the transgene and the conversion agent are co-expressed in the target cell. Such a novel recombinant adeno-associated virus comprises the following components:

(a) the DNA of, or corresponding to, at least a portion of the genome of an adeno-associated virus which portion is capable of transducing at least two selected genes or functional fragments thereof into a target cell in the absence of cell division;

(b) a first selected gene, i.e., the desired transgene, operatively linked to regulatory sequences directing its expression, and (c) a second selected gene, i.e., the "conversion gene" operatively linked to regulatory sequences capable of directing expression of said second gene. The "conversion gene" upon expression is capable of facilitating the conversion of the single stranded recombinant virus to its double stranded form upon expression. The first and second genes in this recombinant virus are flanked by the AAV DNA, preferably the 5' and 3' ITRS. An embodiment of such a second generation rAAV is provided schematically in FIG. 13. Its DNA [SEQ ID NO:2] is provided in FIG. 12.

Another embodiment of such a novel rAAV may include more than one gene which upon expression has the ability to facilitate conversion of ss to ds rAAV in the target cell. For example, the novel rAAV described above may also contain an additional selected gene operatively linked to regulatory sequences capable of directing its expression, the additional gene and said second "conversion" gene described above being capable of jointly facilitating the conversion of single stranded recombinant virus to its double stranded form upon expression of both the second and additional genes. In this recombinant virus, all three genes, i.e., the transgene, the second "conversion" gene and the additional gene are flanked by the AAV DNA.

Thus, in one desirable embodiment of a novel recombinant virus, the AAV ITRs flank a selected transgene, and a conversion gene, which is the adenovirus E4 gene or a functional fragment thereof (e.g., the ORF6 sequence, nucleotides 3402–4286 of SEQ ID NO:2). In another embodiment, the novel recombinant expresses three genes, the transgene, the adenovirus E4 gene or a functional fragment thereof and the adenovirus E1 gene or a functional fragment thereof. The E4 and E1 gene products expressed in the target cell with the transgene, together act to facilitate conversion of the ss to ds form of rAAV.

In still another embodiment of the novel rAAV and its use, the regulatory sequences directing expression of the conversion gene, e.g., whether it be a single second gene or more than a single additional gene, may include an inducible promoter. Thus, expression of the conversion gene occurs only in the presence of an inducing agent. Many inducible promoters and companion inducing agents, e.g., steroids such as glucocorticoids, are known to the art and may be readily selected for incorporation into the rAAV and methods of this invention by one of skill in the art with resort to this description.

The method of the invention employing such "second generation" rAAVs which carry at least one "conversion gene" provides for infecting the target cell with this ss rAAV. Where the promoters directing expression of the both the transgene and the conversion gene are constitutive, the infected target cell machinery will direct the expression of the transgene product and conversion gene product. Co-expression in the target cell of the transgene and the "conversion gene" facilitates the conversion of ss rAAV to ds rAAV in the cell, and increases the transduction efficiency, and perhaps stable chromosomal integration, without further method steps.

When the second generation rAAV employed in the method contains the "conversion gene(s)" under the control of inducible promoter(s), the method is slightly altered. Following infection of the target cell by the rAAV, the infected target cell is contacted with a suitable inducing agent, which triggers the inducible promoter to "turn on" production of the conversion gene product. When the inducing agent is removed or stopped, the expression of the conversion gene product is "turned off".

As described above, any prior art rAAV containing a transgene for gene therapy may be used in at least one embodiment of the above methods. The sources, selection and assembly of the various components to generate the rAAV, including the novel rAAV described above, are now conventional and readily accessible to one of skill in this art, given the disclosure contained herein. Such methods employ conventional genetic engineering techniques [See, e.g. Sambrook et al, "Molecular Cloning. A Laboratory Manual.", 2d edit., Cold Spring Harbor Laboratory, New York (1989)].

The novel rAAV viruses and the methods of this invention provide efficient gene transfer vehicles for somatic gene therapy and are suitable for ex vivo applications and in vivo use. When rAAV contain a therapeutic gene, e.g., in place of the LacZ transgene illustrated in the exemplary rAAV, AV.CMVLacZ, by use of the rAAV and the methods described herein, the therapeutic transgene can be delivered to a patient in vivo or ex vivo to provide for efficient transduction, and possibly stable integration, of the desired gene into the target cell. Thus, these novel rAAV and the methods described herein can be employed to correct genetic deficiencies or defects. The potential of AAV to efficiently integrate its genome into nondividing cells is currently being exploited in the development of gene therapies based on ex vivo transduction of hematopoietic stem cells. In vivo application of rAAV is primarily being developed for the treatment of CF where purified stocks of virus are instilled into the airway to transduce the terminally differentiated epithelial cells of conducting airway. The methods and compositions described herein can be used with both types of gene therapy. Another condition suitable for such use includes transduction of the low density lipoprotein (LDL) receptor gene into hepatocytes for the treatment of familial hypercholesterolemia. One of skill in the art can generate any number of rAAV which can be used via the above methods for the treatment of these and other disorders.

For ex vivo or for in vivo therapy, the rAAV may be used to infect the target cells by suspending the virus particles in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The rAAV are administered in sufficient amounts to transfect the desired cells and provide sufficient levels of expression of the selected transgene to provide a therapeutic benefit without undue adverse, or with medically acceptable, physiological effects which can be determined by those skilled in the medical arts. Conventional and pharmaceutically acceptable routes of in vivo administration include direct delivery to the target organ, tissue or site, intranasal, intravenous, intramuscular, subcutaneous, intradermal, oral and other parental routes of administration. Routes of administration may be combined, if desired.

Dosages of the rAAV for the infecting step of the method will depend primarily on factors such as the therapeutic environment, i.e., ex vivo or in vivo; the condition being treated, the selected gene, the age, weight and health of the patient, and may thus vary among patients. A therapeutically effective dosage of the rAAV for ex vivo treatment will be based upon the multiplicity of infection, which is likely to range from between about 1 to about 10 transducing particles/cell. A therapeutically effective human dosage of the rAAV for in vivo infection according to the present invention is believed to be in the range of from about 20 to about 50 ml of saline solution containing concentrations of from about $1\times10^7$ to $1\times10^{10}$ transducing viral particles/ml virus. A preferred human dosage is about 20 ml saline solution at the above concentrations. The dosage will be adjusted to balance the therapeutic benefit against any side effects. The levels of expression of the selected gene can be monitored to determine the selection, adjustment or frequency of dosage administration.

The effective amount of the facilitating agent to be administered is within the skill of the art to determine and will depend upon the identity of the agent. Known dosages of certain of the classes of chemicals and pharmaceuticals described above may be employed in this method to damage the DNA and facilitate ss to ds conversion of the rAAV. Where the agent is a gene expressed by a helper virus, the amounts of infecting virus should be similar to those amounts described above for the rAAV. Of course, where the agent is a gene present in a second generation rAAV, the identical dosages described above for the rAAV will apply.

Several embodiments of the above-described methods of this invention were confirmed in murine models of rAAV mediated gene transfer to both lung and liver. These experiments demonstrated similarly low levels of gene transfer in vivo by rAAV, which was increased several orders of magnitude by coinfection with E1 and E4 expressing adenovirus.

In summary, experiments were conducted to demonstrate that adenovirus enhances rAAV transduction in cultured cells. During the production and characterization of a lacZ recombinant AAV generated in 293 cells that were coinfected with an E1 deleted virus, it was observed that purification of rAAV from lysates was associated with substantial loss of lacZ transducing activity when assayed on 293 cells. This drop in rAAV activity was particularly evident in the final step where residual contaminating helper adenovirus was removed by heat inactivation. LacZ transducing activity was recovered by adding adenovirus back to the purified stock of rAAV. These data provided the first indication that adenovirus could substantially enhance the transduction efficiency of rAAV.

Figure 1F:
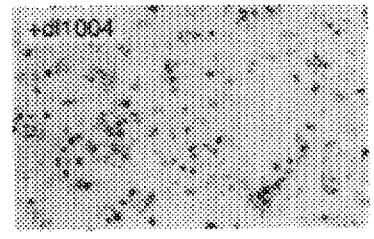
FIG. 1F is a similar photomicrograph in HeLa cells transfected with AV.CMVLacZ and Ad mutant dl1004.
Figure 1G:
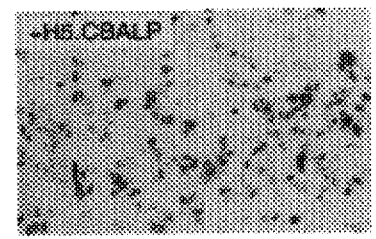
FIG. 1G is a similar photomicrograph in HeLa cells transfected with AV.CMVLacZ and Ad mutant H5.CBALP.
Figure 1H:
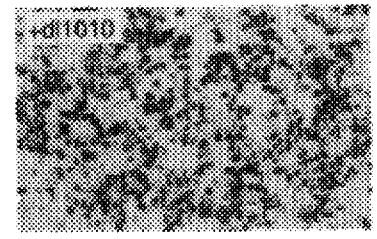
FIG. 1H is a similar photomicrograph in HeLa cells transfected with AV.CMVLacZ and Ad mutant dl1010.
Figure 2A:
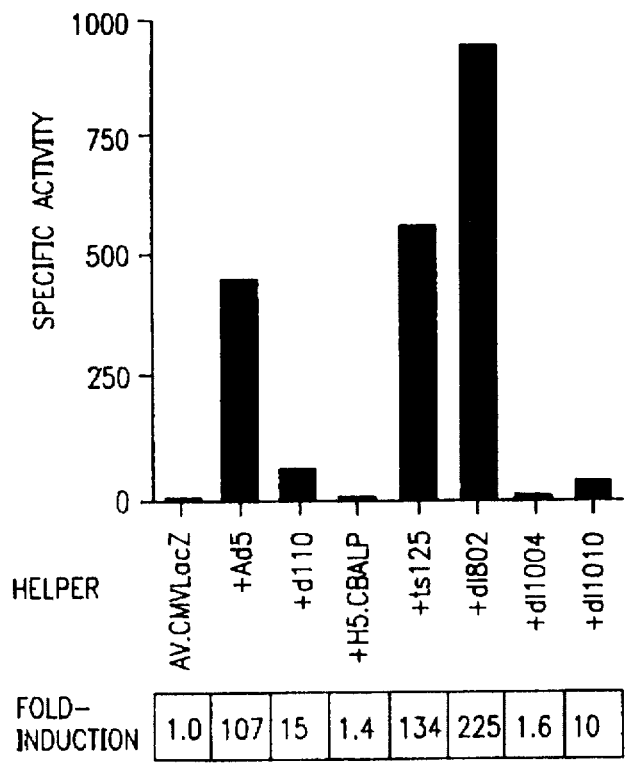
FIG. 2A is a bar graph plotting β-galactosidase enzyme activity in lysates from infected Hela cells. The horizontal axis indicates the adenoviruses infected into the HeLa cells, with the symbol "+" indicating the addition of the adenovirus to the rAAV, AV.CMVLacZ. The vertical axis indicates intracellular β-galactosidase specific activity (mUnits/mg protein) using ONPG. Below each bar, the fold-induction in specific activity relative to cells that received the AV.CM-VLacZ vector alone is given.

As described in Example 2, a series of complementation groups were generated by mixing different adenovirus early gene mutants with purified LacZ rAAV, referred to as AV.CMVLacZ (see Example 1). These defined mixtures of viruses were analyzed for LacZ transduction on Hela cells (See Examples 3 and 4). An E1 deletion recombinant adenovirus H5.CBALP and the E4 deletion mutant dl1004 provided no significant increase in AV.CMVLacZ transduction (FIGS. 1 and 2A). However, partial activity could be achieved with E1 and E4 mutants that carried less severe deletions. Both dl110 (E1B-55kDa deleted) and dl1010 (ORF6 deleted) enhanced transduction to levels that approached those of Ad5, ts125, and dl802 in terms of the number of positive blue cells (FIGS. 1A to 1H), but total β-galactosidase activity was substantially lower (FIG. 2A). These results implicate early regions E1 and E4 in the augmentation of rAAV transduction.

The experiments described below also demonstrate that the novel rAAV which incorporates as its conversion gene, an Ad gene, such as E4, can increase transduction efficiency of the rAAV in the absence of a helper virus. As described in more detail below in Example 7 below, 293 cells were stably transfected with a genomic fragment of Ad5 spanning E4. This E1/E4 expressing cell line and the parent E1 expressing cell line (293) were infected with rAAV and analyzed for transduction. These experiments demonstrated the significance of the combined expression of E1 and E4(ORF6) in the adenovirus mediated augmentation of rAAV transduction.

Figure 3A:
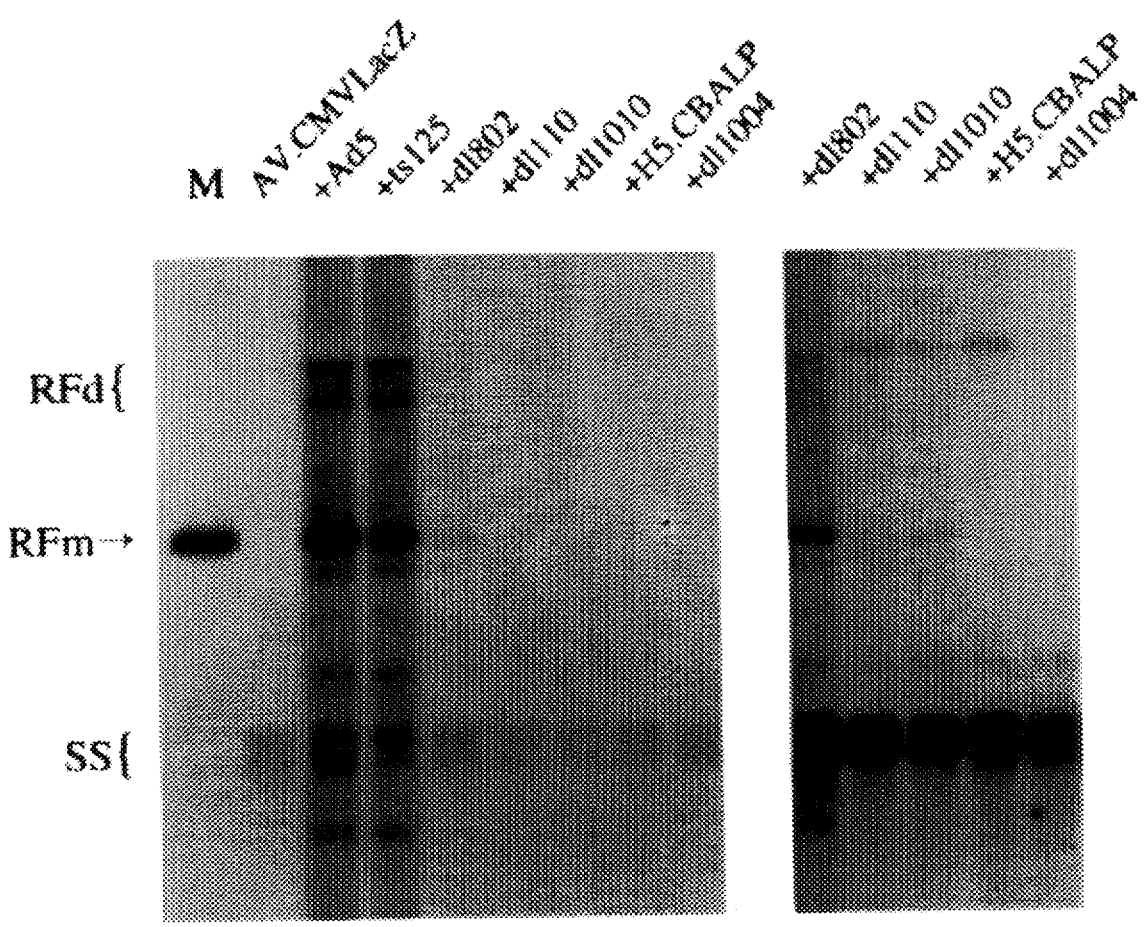
FIG. 3A is an autoradiogram of the experiment of Example 4, which identifies and labels bands corresponding to the single-stranded AV.CMVLacZ genome (SS), a monomer replicative form (RFm), and concatomer replicative forms (RFd). In lane M, the entire rAAV genome was provided. Autoradiogram exposure times were 14 hours (left) and 69 hours (right).
Figure 5C:
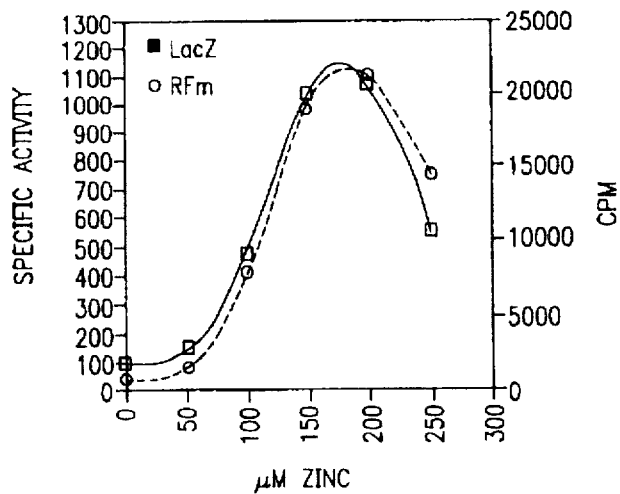
FIG. 5C is a comparison of the induction profiles that describe AV.CMVLacZ transduction efficiency. Specific activity data from FIG. 5A and CPM data of AV.CMVLacZ RFm from FIG. 5B are plotted along the vertical axis, and concentration of zinc sulfate used during the experiment is shown along the horizontal axis.
Figure 6:
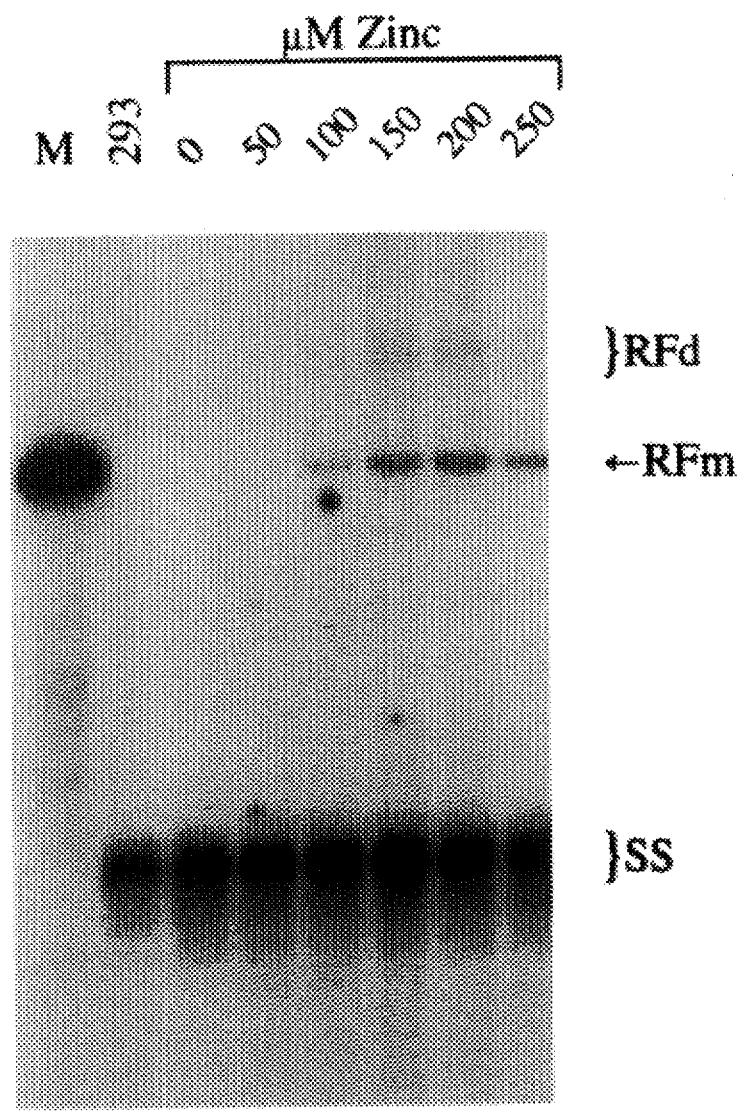
FIG. 6 is an autoradiograph showing agarose gel resolved Hirt extracts from AV.CMVLacZ transduced cells and is described in Example 6 below.
Figure 7A:
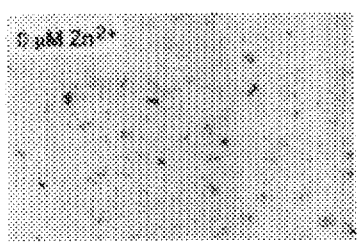
FIG. 7A is a photomicrograph of a histochemical stain of β-galactosidase activity in HeLa(MT-ORF6) cells transduced at an MOI of 1,000 AV.CMVLacZ recombinant virus particles/cell in the absence of zinc sulfate inducer.
Figure 7B:
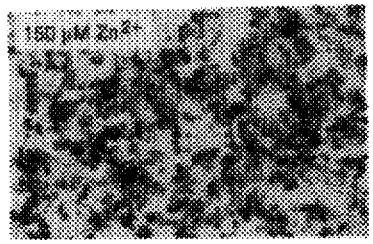
FIG. 7B is a photomicrograph of a histochemical stain of β-galactosidase activity in HeLa(MT-ORF6) cells transduced at an MOI of 1,000 AV.CMVLacZ recombinant virus particles/cell in the presence of 150 μM zinc sulfate inducer present in the media during transduction.
Figure 7C:
FIG. 7C is a photomicrograph of a histochemical stain of β-galactosidase activity in HeLa(MT-ORF6) cells transduced at an MOI of 1,000 AV.CMVLacZ recombinant virus particles/cell in the presence of 50 μM zinc sulfate inducer.
Figure 7D:
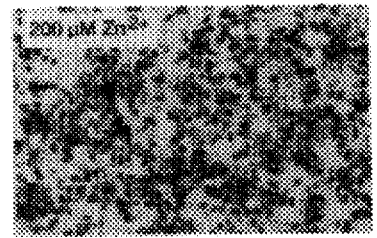
FIG. 7D is a photomicrograph of a histochemical stain of β-galactosidase activity in HeLa(MT-ORF6) cells transduced at an MOI of 1,000 AV.CMVLacZ recombinant virus particles/cell in the presence of 200 μM zinc sulfate inducer.
Figure 7E:
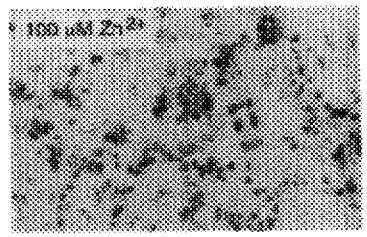
FIG. 7E is a photomicrograph of a histochemical stain of β-galactosidase activity in HeLa(MT-ORF6) cells transduced at an MOI of 1,000 AV.CMVLacZ recombinant virus particles/cell in the presence of 100 μM zinc sulfate inducer.
Figure 7F:
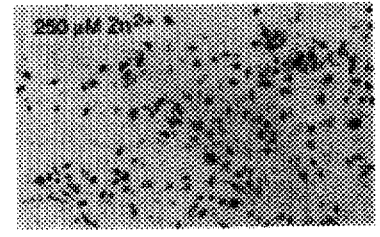
FIG. 7F is a photomicrograph of a histochemical stain of β-galactosidase activity in HeLa(MT-ORF6) cells transduced at an MOI of 1,000 AV.CMVLacZ recombinant virus particles/cell in the presence of 250 μM zinc sulfate inducer.

In the presence of E1 and E4 expression, rAAV transduction was invariably accompanied by the appearance of double-stranded RF monomers and dimers (FIGS. 3A and 6). Importantly, the tight correlation between rAAV vector transduction and the accumulation of duplex forms could be achieved in two different experimental settings; cells infected with E1/E4 expressing adenovirus (FIGS. 3B and 3C), or complementing cell lines (FIG. 5C).

The following examples illustrate the improved methods and second generation recombinant AAV production for gene therapy of the present invention. These examples are illustrative only, and do not limit the scope of the present invention.

Example 1—Production of a Recombinant AAV

Figure 11:
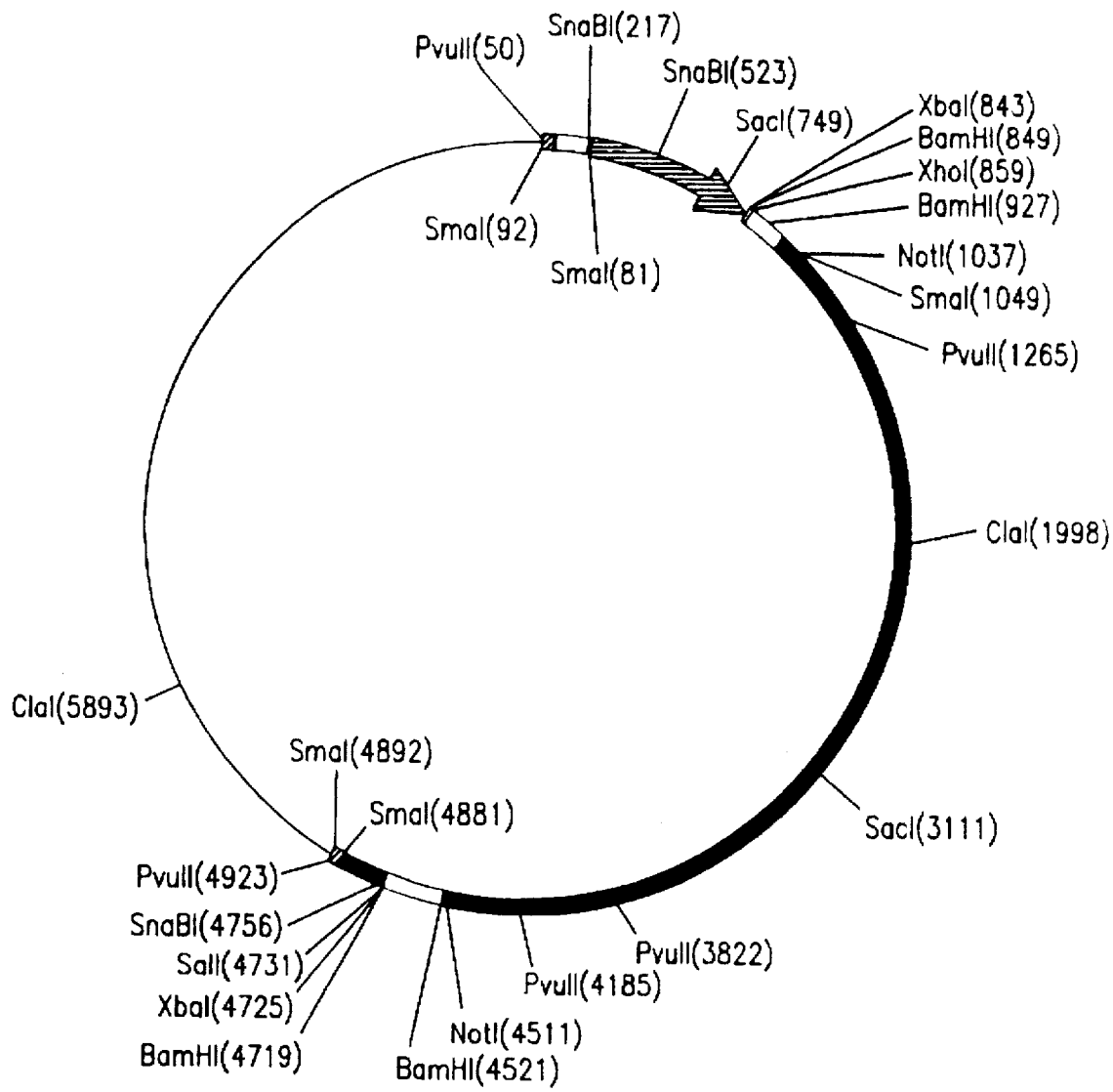
FIG. 11 is a schematic of the plasmid pAV.CMVLacZ.

A recombinant AAV virus was prepared by conventional genetic engineering techniques for the purposes of this experiment. Recombinant AAV was generated by plasmid transfections in the presence of helper adenovirus [Samulski et al. *J. Virol.*, 63:3822–3828 (1989)]. The cis-acting plasmid pAV.CMVLacZ [SEQ ID NO: 1) (see FIGS. 10 and 11) was derived from psub201 [Samulski et al. *J. Virol.*, 61:3096–3101 (1987)] and contains an *E. coli* βgalactosidase minigene in place of AAV Rep and Cap genes. Therefore, the 5' to 3' organization of the recombinant AV.CMVLacZ genome (4.9 kb) includes (a) the 5' AAV ITR (bp 1–173) was obtained by PCR using pAV2 [C. A. Laughlin et al. Gene, 23: 65–73 (1983)] as template [nucleotide numbers 53–219 of SEQ ID NO: 1];

(b) a CMV immediate early enhancer/promoter [Boshart et al. *Cell*, 41:521–530 (1985)] (nucleotide numbers 246–839 of SEQ ID NO: 1), (c) an SV40 intron (nucleotide numbers 856–987 of SEQ ID NO: 1), (d) *E. coli* beta-galactosidase CDNA (nucleotide numbers 1039–4512 of SEQ ID NO: 1), (e) an SV40 polyadenylation signal (a 237 Bam HI-BclI restriction fragment containing the cleavage/poly-A signals from both the early and late transcription units (nucleotide numbers 4522–4719 of SEQ ID NO: 1] and (f) 3' AAV ITR, obtained from pAV2 as a SnaBI-BglII fragment (nucleotide numbers 4759–4925 of SEQ ID NO: 1).

Rep and Cap genes were provided by a trans-acting plasmid pAAV/Ad [Samulski et al. cited above].

Monolayers of 293 cells grown to 90% confluency in 150 mm culture dishes ($5 \times 10^7$ cells/plate) were infected with H5.CBALP at an MOI of 10. H5.CBALP is a recombinant adenovirus that contains an alkaline phosphatase minigene in place of adenovirus E1A and E1B gene sequences (map units 1–9.2 of the Ad5 sequence of GenBank [Accession No. M73260]). The alkaline phosphatase cDNA is under the transcriptional control of a CMV-enhanced β-actin promoter in this virus.

Infections were done in Dulbecco's Modified Eagles Media (DMEM) supplemented with 2% fetal bovine serum (FBS) at 20 ml media/150 mm plate. Two hours post-infection, 50 µg plasmid DNA (37.5 µg trans-acting and 12.5 µg cis-acting) in 2.5 ml of transfection cocktail was added to each plate and evenly distributed. Transfections were calcium phosphate based as described [B. Cullen, *Meth. Enzymol.*, 152:684–704 (1987)]. Cells were left in this condition for 10–14 hours after which the infection/transfection media was replaced with 20 ml fresh DMEM/2% FBS. Forth to fifty hours post-transfection, cells were harvested, suspended in 10 mM Tris-Cl (pH 8.0) buffer (0.5 ml/150 mm plate) and a lysate prepared by sonication. The lysate was brought to 10 mM manganese chloride, after which bovine pancreatic DNase I (20,000 units) and RNase (0.2 mg/ml final concentration) were added, and the reaction incubated at 37° C. for 30 minutes. Sodium deoxycholate was added to a final concentration of 1% and incubated at 37° C. for an additional 10 minutes.

The treated lysate was chilled on ice for 10 minutes and solid CsCl added to a final density of 1.3 g/ml. The lysate was brought to a final volume of 60 ml with 1.3 g/ml CsCl solution in 10 mM Tris-Cl (pH 8.0) and divided into three equal aliquots. Each 20 ml sample was layered onto a CsCl step gradient composed of two 9.0 ml tiers with densities 1.45 g/ml and 1.60 g/ml.

Centrifugation was performed at 25,000 rpm in a Beckman SW-28 rotor for 24 hours at 4° C. One ml fractions were collected from the bottom of the tube and analyzed on 293 or 293(E4) cells for LacZ transduction. Fractions containing peak titers of functional AV.CMVLacZ virus were combined and subjected to three sequential rounds of equilibrium sedimentation in CsCl. Rotor selection included a Beckman NVT-90 (80,000 rpm for 4 hours) and SW-41 (35,000 rpm for 20 hours). At equilibrium, AV.CMVLacZ appeared as an opalescent band at 1.40–1.41 g/ml CsCl. Densities were calculated from refractive index measurements. Purified vector was exchanged to 20 mM HEPES buffer (pH7.8) containing 150 mM NaCl (HBS) by dialysis and stored frozen at −80° C. in the presence of 10% glycerol or as a liquid stock at −20° C. in HBS/40% glycerol.

Purified virus was tested for contaminating H5.CBALP helper virus and AV.CMVLacZ titers. Helper virus was monitored by histochemical staining for reporter alkaline phosphatase activity. A sample of purified virus representing 1.0% of the final product was added to a growing monolayer of 293 cells seeded in a 60 mm plate. Forty-eight hours later, cells were fixed in 0.5% glutaraldehyde/phosphate buffered saline (PBS) for 10 minutes at room temperature, washed in PBS (3×10 minutes) and incubated at 65° C. for 40 minutes to inactivate endogenous alkaline phosphatase activity. The monolayer was allowed to cool to room temperature, rinsed once briefly in 100 mM Tris-Cl (pH9.5)/100 mM NaCl/5 mM MgCl, and incubated at 37° C. for 30 minutes in the same buffer containing 0.33 mg/ml nitroblue tetrazolium chloride (NBT) and 0.165 mg/ml 5-bromo-4-chloro-3-indolylphosphate p-toluidine salt (BCIP). Color development was stopped by washing the monolayer in 10 mM Tris-Cl (pH 8.0)/5 mM EDTA. Routinely the purification scheme described above removed all detectable H5.CBALP helper virus by the third round of buoyant density ultracentrifugation.

AV.CMVLacZ titers were measured according to genome copy number (virus particles/ml), absorbance at 260 nm ($A_{260}$ particles/ml) and LacZ Forming Units (LFU/ml). Virus particle concentrations were based on Southern blotting. Briefly, a sample of purified AV.CMVLacZ was treated with capsid digestion buffer (50 mM Tris-Cl, pH 8.0/1.0 mM EDTA, pH 8.0/0.5% SDS/Proteinase K 1.0 mg/ml) at 50° C. for one hour to release virus DNA. The reactions were allowed to cool to room temperature, loading dye was added and electrophoresed through a 1.2% agarose gel. Standard quantities of ds AV.CMVLacZ genome were also resolved on the gel.

DNAs were electroblotted onto a nylon membrane, hybridized with a $^{32}$P random primer labeled restriction fragment, and the resulting blot scanned on a PhosphorImager 445 SI (Molecular Dynamics). A standard curve was generated from the duplex forms and used to extrapolate the number of virus genomes in the sample. LFU titers were generated by infecting indicator cells with limiting dilutions of virus sample. Indicator cells included HeLa, 293 and 293 (E4) lines (described in Example 2 below). Twenty-four hours later, cells were fixed in glutaraldehyde as above and histochemically stained for β-galactosidase activity [Wilson et al (1988)]. One LFU is described as the quantity of virus that is sufficient to cause visually detectable β-galactosidase expression in one cell 24 hours post-infection.

Example 2—Transduction Efficiency of a Recombinant AAV LacZ Vector (AV.CMVLacZ) in HeLa Cells Infected with Different Adenovirus Mutants A. Viruses The following viruses were employed in this experiment:

(1) Wild-type Ad 5, propagated in 293 cells;

(2) Ad dl110 (an Ad which is deleted of the 55 kb E1B gene) [Babiss et al, J. Virol., 52(2):389–395 (1984) and Babiss and Ginsberg, J. Virol., 50(1):202–212 (1984)], propagated in 293 cells.

(3) H5.CBALP (an Ad deleted of its E1A and E1B genes and containing a minigene that expresses alkaline phosphatase from a CMV enhanced β-actin promoter, as described above), propagated in 293 cells, (4) Ad ts125 (an Ad with a temperature sensitive mutation in the E2A gene which encodes the DNA binding protein) [Ensinger and Ginsberg, J. Virol., 10(3):328–339 (1972)], propagated in 293 cell, (5) Ad dl802 (an Ad deleted of its E2a gene), grown in E2A-complementing gmDBP cells as described in Rice and Klessig, J. Virol., 56(3):767–778 (1985);

(6) Ad dl1004 (an Ad deleted of the E4 gene), grown in E4-complementing Vero W162 cells [Weinberg and Ketner, Proc. Natl. Acad. Sci. USA, 80(17):5383–5386 (1983)] and (7) Ad dl1010 (an Ad deleted of ORF6 of its E4 gene), grown in E4-complementing Vero W162 cells [Weinberg and Ketner, cited above].

All viruses were purified by two sequential rounds of buoyant density ultracentrifugation in CsCl.

B. Experimental Procedures

HeLa cells seeded in 6 well, 36 mm culture plates ($2\times10^6$ cells/well) were infected with wild-type Ad5 or an adenovirus early gene mutant as described in Part A at an MOI of 10pfu/well. Infections were done in 1.0 ml DMEM/2% FBS. Six hours post-infection, monolayers were washed and 1.0 ml fresh DMEM/2% FBS media containing AV.CMVLacZ at $4\times10^9$ virus particles/ml were added. Although the AV.CMVLacZ virus lot used in these experiments was shown to be free of H5.CLALP helper virus by histochemical staining, the virus sample was subjected to heat treatment (60° C. for 20 minutes) prior to use to ensure the absence of contaminating adenovirus. Two hours later, 1.0 ml of DMEM/115% FBS was added to each well.

Twenty-four hours after the addition of AV.CMVLacZ, cells were harvested. Each test condition was done in triplicate to enable virus transduction to be evaluated in terms of three outputs: histochemical staining for β-galactosidase activity (below), intracellular β-galactosidase specific activity (Example 3), and the molecular form of the virus DNA (Example 4).

Cells were histochemically stained for E. coli β-galactosidase (LacZ) activity as described in J. M. Wilson et al, Proc. Natl. Acad. Sci. USA, 85:3014–3018 (1988). The different combinations that were tested included AAV vector alone (AV.CMVLacZ), vector plus wild-type Ad5 (+Ad5), vector plus dl110 (+dl110), vector plus H5.CBALP (+H5.CBALP), vector plus ts125 (+ts125), vector plus dl802 (+dl802), vector plus dl1004 (+dl1004), and vector plus dl1010 (+dl1010).

The results are illustrated in the photomicrographs of FIGS. 1A through 1H. Histochemical staining for recombinant β-galactosidase activity indicated that wild-type Ad5 (Fig. 1C), and the E2a mutants ts125 (FIG. 1B), and dl802 (FIG. 1D) caused a significant increase in LacZ rAAV transduction as measured by the number of positive blue cells and the degree of stain intensity. Both dl110 (E1B-55kDa) (FIG. 1E) and dl1010 (ORF6) (FIG. 1H) enhanced transduction to levels that approached those of Ad5, ts125, and dl802 in terms of the number of positive blue cells.

The E1 deletion recombinant H5.CBALP (FIG. 1G) provided no significant increase in AV.CMVLacZ transduction. Expression of E1 alone was insufficient to have an effect in the adenovirus mediated augmentation of rAAV transduction as evidenced by lack of significant increase in transduction obtained with HeLa cells infected with the E4 deletion mutant dl1004 (Fig. 1F).

A significant drop in transduction occurred following removal of ORF6 from the E4 region from the coinfecting adenovirus (FIGS. 1 and 2A).

It is believed that these results demonstrate that the adenoviral gene products, E4 and E1 indirectly promote the formation of double stranded DNA intermediates that are transcriptionally active.

Example 3—Quantitation of Enhanced Vector Transduction (A) A duplicate set of HeLa cells as described in Example 1B were used in this experiment. Twenty-four hours after the addition of AV.CMVLacZ recombinant virus, for intracellular β-galactosidase assays, cell pellets were suspended in 0.5 ml PBS and sonicated. Cell debris was removed by centrifugation (15,000×g for 10 minutes) and the clarified extract assayed for total protein [M. Bradford, Anal. Biochem., 72(1–2):248–254 (1976) and M. Bradford et al, Fed. Proc., 35(3):274 (1976)] and β-galactosidase activity [Sambrook et al, cited above] using o-nitrophenyl β-D-galactopyranoside (ONPG) as substrate.

FIG. 2A demonstrates the transduction efficiency quantitated by measuring β-galactosidase enzyme activity in the lysates from infected Hela cells and also assayed for total protein. In FIG. 2A, the test condition is shown along the horizontal axis, and intracellular β-galactosidase specific activity (milliunits/mg protein) using ONPG as substrate is plotted on the vertical axis. Below each bar, the fold-induction in specific activity relative to cells that received the AV.CMVLacZ vector alone is given.

The results of FIG. 2A demonstrate that the E2a mutants ts125 and dl802 produced 134-fold and 225-fold increases in β-galactosidase activity, respectively, as compared to that achieved with purified rAAV alone. In comparison, cells infected with wt Ad5 generated 107-fold increase in β-galactosidase activity.

(B) In another experiment, HeLa cells ($2\times10^6$) were infected with increasing multiplicities of wild-type Ad5 or the E2 mutant dl802. Six hours post-infection, monolayers were washed and infected with AV.CMVLacZ at 1000 virus particles/cell. Twenty-four hours after the addition of AV.CMVLacZ, cells were harvested and assayed for total protein and β-galactosidase activity.

Figure 2B:
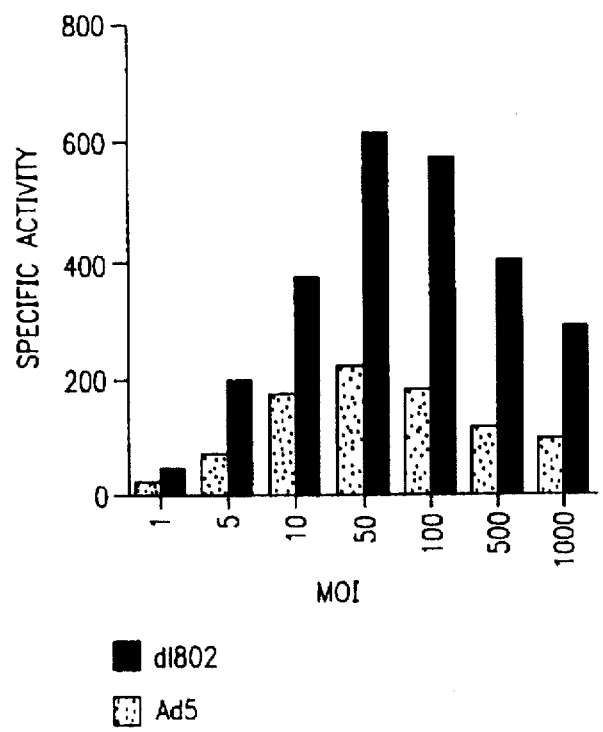
FIG. 2B is a bar graph plotting Ad multiplicity of infection (MOI) in HeLa cells of wild-type Ad5 or the E2 mutant dl802, the cells co-infected with rAAV vs. intracellular β-galactosidase specific activity. See Example 3.

The results are illustrated in the bar graph of FIG. 2B, in which adenovirus MOI's are given along the horizontal axis, and intracellular β-galactosidase specific activity along the vertical axis. Enhancement of rAAV transduction was proportional to input helper adenovirus from MOIs of 1 to 50 for both wild type Ad5 and dl802. Higher doses of virus were cytopathic, leading to a fall in β-galactosidase expression. Enhanced transduction was achieved when the cells were infected prior to, or at the time of, rAAV infection. The E1 deletion recombinant H5.CBALP and the E4 deletion mutant dl1004 provided no significant increase in AV.CMVLacZ transduction. Both cells infected with dl110 (E1B 55kDa) and with dl1010 (ORF6) demonstrated substantially lower total β-galactosidase activity than those infected with Ad5, ts125, or dl802.

Example 4—Analysis of Low Molecular Weight DNAs in AV.CMVLacZ Transduced Cells Studies with these early gene mutants of adenovirus suggested that expression of adenoviral genes rather than the virion itself was responsible for enhancement of rAAV transduction. To further investigate these mechanisms and to determine if conversion of single-stranded to double-stranded genome limits the transduction efficiency of rAAV, the molecular state of the rAAV genome was characterized in the infected cells. The relationship between RFm formation and lacZ rAAV transduction was explored in experiments where the dose of coinfecting virus was varied (MOI=1, 5, or 10).

(A) A duplicate set of HeLa monolayers as described in Example 2 were harvested 24 hours after they were transduced with the recombinant virus AV.CMVLacZ and cultured with or without helper adenovirus.

Episomal DNA was extracted from cell pellets using a modification of the procedure originally described by B. Hirt, *J. Mol. Biol.*, 26:365–369 (1967). Briefly, cells were suspended in 320 ml Tris-Cl (pH8.0)/10 mM EDTA and SDS added to a final concentration of 1%. The mixture was incubated at 37° C. for 30 minutes. Pronase and proteinase K were added to final concentrations of 500 µg/ml and 20 µg/ml, respectively, and the reaction incubated at 37° C. for 2 hours. Sodium chloride was added to a final concentration of 1.1M and incubated at 4° C. overnight. The precipitate that developed during the 4° C. incubation was pelleted at 20,000×g for 30 minutes and the clear supernatant carefully removed. The supernatant was extracted once with phenol:chloroform:isoamyl alcohol (25:24:1) followed by chloroform:isoamyl alcohol (24:1). Nucleic acids were precipitated with ethanol. The final pellet was suspended in 50 µl Tris-Cl (pH 8.0)/1.0 mM EDTA.

These Hirt extracts were analyzed by Southern blot hybridization. Samples (5 µl) of each Hirt extract were resolved through a 1.2% agarose gel, electroblotted onto a nylon membrane and hybridized with a $^{32}$P random primer labeled cDNA of the SV40 polyA signal used in AV.CMVLacZ.

Bands corresponding to the single-stranded AV.CMVLacZ genome (SS), a monomer replicative form (RFm), and concatomer replicative forms (RFd) were identified and labeled (FIG. 3A). To reference the RFm band, a plasmid carrying AV.CMVLacZ was digested to release the entire genome (lane labeled M). Autoradiogram exposure times were 14 hours (left) and 69 hours (right).

The full spectrum of molecular species present during a lytic infection was demonstrated in cells infected with both LacZ rAAV and wild type adenovirus (FIG. 3A, lane +Ad5); both the input single stranded genome (SS) and monomeric and dimeric forms of double stranded replicative intermediates (RFm and RFd) are present. This contrasts with cells infected with purified rAAV alone where single stranded genome is the sole molecular form detected (FIG. 3A, lane AV.CMVlacZ). Analysis of cells coinfected with the adenovirus early gene mutants revealed a direct correlation between formation of double stranded forms of the rAAV genome and the enhancement of LacZ transduction. Mutant adenoviruses that were ineffective in enhancing rAAV transduction (i.e., the E1 deleted mutant H5.CBALP and the E4 deleted mutant dl1004) failed to promote the formation of double stranded forms of AAV.

Cells infected with adenovirus deleted of E2a (dl802) or partially deleted of E1 (dl110 ) or E4 (dl1010 ) additionally demonstrated a band whose size was identical to the double-stranded replicative monomer (RFm) of the lacZ rAAV genome (FIG. 3A) and whose abundance correlated directly with the expression of β-galactosidase activity (compare FIG. 2A to 3A). Slower migrating concatomers, likely dimers, of duplex rAAV were also detected (FIG. 3A).

In the presence of E1 and E4 expression, recombinant virus transduction was invariably accompanied by the appearance of double-stranded RF monomers and dimers.

The high molecular weight band in sample lane +H5.CBALP is helper virus DNA. Helper virus DNA is recognized by the SV40 probe because the CBALP minigene also utilizes the SV40 polyA signal.

(B) In another experiment, HeLa cells were infected with wt Ad5 or the E2 deleted mutant dl802 as described in Example 2B. Monolayers were harvested 24 hours later and analyzed for β-galactosidase activity and RFm synthesis. Monomer bands similar to those shown in FIG. 3A were quantitated on a PhosphorImager 445 SI and assigned values (CPM).

Figure 3B:
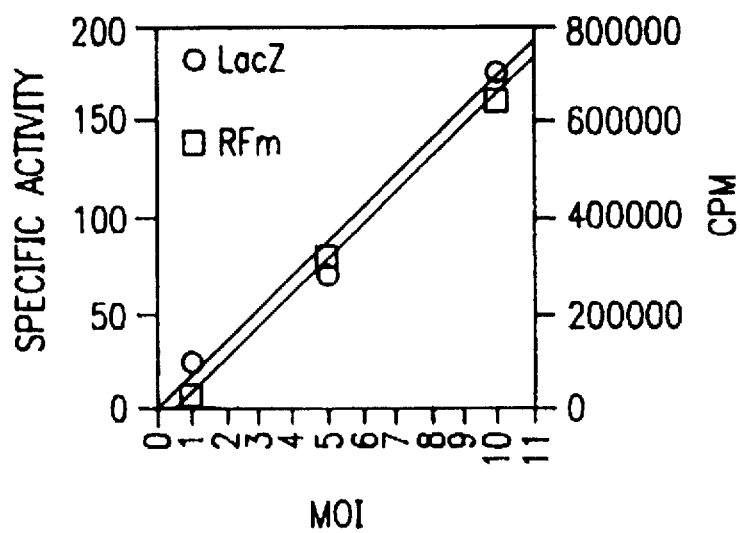
FIG. 3B is a graph in which β-galactosidase specific activity and counts per minute (CPM) are plotted along the vertical axis and adenovirus MOI's are on the horizontal axis for HeLa cells infected with wtAd5 and rAAV according to Example 4. Data obtained from low MOI (1, 5, and 10) infections are shown.
Figure 3C:
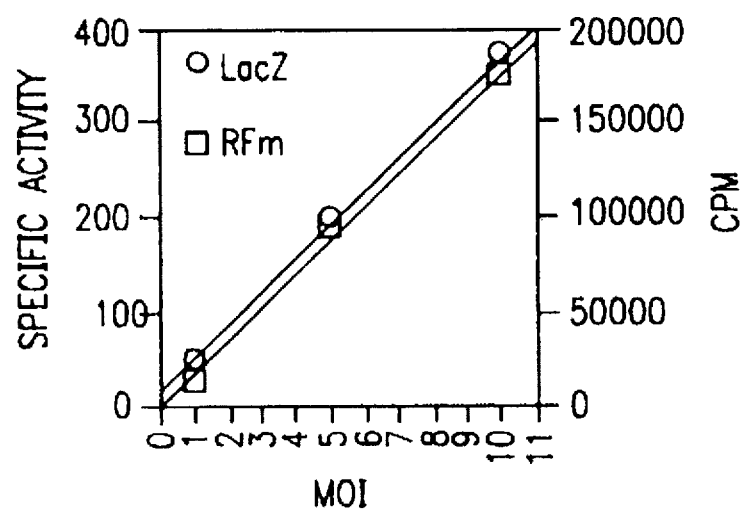
FIG. 3C is a graph similar to that of FIG. 3B except that the cells were infected with Ad mutant dl802 rather than wt Ad5.

The results are illustrated in the graphs of FIGS. 3B and 3C, in which β-galactosidase specific activity and CPM are plotted along the vertical axis of each figure. Adenovirus MOI's are given on the horizontal axis of each figure. Data obtained from low MOI infections (1, 5, and 10) are shown. Importantly, the tight correlation between rAAV vector transduction and the accumulation of duplex forms could be achieved in cells infected with E1/E4 expressing adenovirus. The level of β-galactosidase and abundance of RFm increased in proportion to the amount of infecting wild type Ad (FIG. 3B) and dl802 (FIG. 3C). These data suggest that synthesis of an episomal duplex intermediate is an obligatory event in transduction.

Example 5—Duplex End-Analysis

The following is a description of a model for leading strand synthesis of a complementary AAV strand in the presence of Rep (+Rep) or absence of Rep (–Rep). Refer to FIGS. 4A–4G. Rep expresses a terminal resolution activity that can convert a duplex structure with closed-ends to an open-ended duplex. In the absence of Rep, terminal resolution is impaired leaving the covalently closed, hairpin structures intact. Under these conditions, hairpins are expected to be found leftward and rightward, since both strands of a rescued double-stranded AAV genome are packaged into virions. FIGS. 4–4F are a flow chart demonstrating the strategy for identifying the terminal structure of duplex RFm that is synthesized from single-stranded AV.CMVLacZ in response to adenoviral gene expression.

FIG. 4C illustrates a closed end and an open end fragment of rAV.CMVLacZ. FIGS. 4D, 4E and 4F indicate the mixture of open-ended and covalently closed duplex fragments generated by NotI digestion at position 4509 in the absence of terminal resolution. The NotI 4509 digestion provides a convenient means of releasing a 361 bp fragment that contains the right ITR in the context of a hybridization target (i.e. SV40 pA). In the presence of terminal resolution, only the open-ended 361 bp fragment would be expected to be generated (FIG. 4D) by such digestion.

In lane (1) of the autoradiogram shown in FIG. 4G, a plasmid carrying an AV.CMVLacZ CDNA was digested to release the vector and then with NotI to release the right terminal 361 bp fragment. In lane (2) is a sample of NotI digested Hirt DNA extracted from HeLa cells infected with wild-type Ad5 and transduced with AV.CMVLacZ (See, FIGS. 3A–3C). The NotI digestion resulted in the release of two fragments, labeled FormI and FormII. The migration of single-stranded AV.CMVLacZ and RFm are also shown.

The double-stranded AV.CMVLacZ intermediates that accumulated in cells infected with adenovirus were likely the result of leading strand DNA synthesis, initiating from the duplex region of the vector ITR. In the absence of Rep, this conversion event was anticipated to generate molecules in which one end is open and the other is covalently closed (FIG. 4A). To further characterize the structure of this double stranded intermediate Hirt extracts from cells coinfected with rAV.CMBLacZ and Ad5 (FIG. 3, lane +Ad) were digested with NotI to release the termini of the double stranded intermediate which, if left open, would be approximately 361 bp in length. The resulting filters were hybridized with a probe specific for the SV40 polyadenylation signal positioned immediately upstream of the rightward ITR. At least two forms were released from the right end of duplex genomes, one that migrated to a position in the gel that predicted an open-ended conformation (Form II), and a second slower migrating species (Form I) (FIG. 4G, lane 2). Although this result was consistent with the model (FIGS. 4A–4G), it was difficult to predict with certainty the structure of Form I. Its retarded mobility did, however, suggest a conformation that differed from the open-ended Form II.

Example 6—Analysis of AV.CMVLacZ Transduction Efficiency in 293 Cells Stably Transfected with an Inducible E4 ORF6 CDNA (A) Cell Lines The entire E4 region from Ad5 or an ORF6 minigene were subcloned into a shuttle plasmid that contained a neomycin resistance gene. Two versions of ORF6 minigene were developed that differed in the promoter element. The first used an Zn+2 inducible sheep metallothionine (MT) promoter to drive ORF 6 expression. The second used a dexamethasone-inducible mouse mammary tumor virus (MMTV) promoter. Plasmids were transfected by calcium phosphate precipitation into 293 or HeLa cells seeded on 100 mm plates (10 µg plasmid/plate). Twenty four hours posttransfection, cells were harvested and seeded at varying dilutions (1:10–1:100) in 100 mm plates. Seeding media contain G418 (Geneticin, BRL) at 1 mg/ml. Resistant colonies that developed were selected and expanded. Preliminary analysis of clones was based on immunofluorescence localization of E4 protein, and later confirmed by enhanced transduction efficiency of AV.CMVLacZ.

To determine whether ORF6 expression was sufficient to enhance rAAV transduction, the inducible metallothionein (MT)-ORF6 minigene was stably transfected into HeLa cells. This new cell line, HeLa(MT-ORF6) was evaluated for LacZ rAAV transduction in response to ORF6 induction as described below. The cell line 293 (MT-ORF6) expresses ORF-6 of the E4 gene of Ad5 from the metallothionine promoter which is relatively inactive at baseline but can be induced with divalent cations. These 293 cells were included to establish the baseline transduction efficiency.

B. Experimental Procedures 293(MT-ORF6) cells and HeLa (MT-ORF6) cells were seeded in 6 well 35 mm culture plates ($2 \times 10^6$ cells/well) and infected with purified, heat-treated AV.CMVLacZ at an MOI of 1000 virus particles/cell. Induction of ORF6 expression with from none to increasing concentrations of zinc sulfate was initiated 2 hours before the addition of virus and continued throughout the duration of the experiment.

Twenty-four hours after the addition of virus, cells were harvested, lysates were generated by sonication and analyzed for the β-galactosidase expression (i.e., β-galactosidase activity) and virus DNA as described in the preceding examples. Hirt extracts were prepared from low molecular weight DNA from cell extracts. The preparation of the Hirt extracts and subsequent analysis by Southern hybridization were performed similarly to those described in the examples above.

C. The Results (1) Specific Activity

Figure 5A:
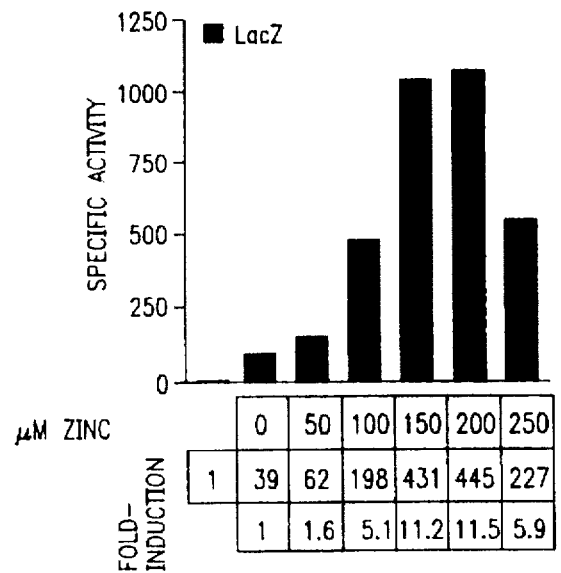
FIG. 5A is a bar graph plotting β-galactosidase specific activity (mUnits/mg protein) vs. increasing concentration of zinc (μM) inducer for cell line 293 (MT-ORF6) transduced with AVCMVLacZ (first row below each bar). Also provided is the fold-induction relative to 293 cells (second row below each bar), and the fold-induction relative to 293(ORF6) cells maintained in the absence of zinc (third row).

The results are illustrated in the bar graph of FIG. 5A. Specific activity (milliunits β-galactosidase/mg protein) is plotted along the vertical axis. Below each bar is given the concentration of zinc used for induction, the fold-induction relative to 293 cells, and the fold-induction relative to 293(ORF6) cells maintained in the absence of zinc. As shown in FIG. 5A, in the absence of Zn+2, the 293(MT-ORF6) cell line generated 39-fold higher levels of β-galactosidase in rAAV infected 293 cells. Induction of ORF6 expression with increasing amounts of $Zn^{+2}$ resulted in a concomitant rise in AV.CMVLacZ cell transduction to a level that was 445-fold greater than the parent 293 line. Expression of E1 alone was insufficient to have an effect in the adenovirus mediated augmentation of rAAV transduction.

The specific activity of β-galactosidase was 196.2 mUnits/mg in E1/E4 expressing 293 cells, compared to 1.0 mUnit/mg in 293 cells that only expressed E1 genes. These experiments support a mechanism for enhancing rAAV transduction that is dependent on the combined expression of both E1 and E4 adenoviral genes.

(2) Molecular Analysis of the AV.CMVLacZ Genome

Figure 5B:
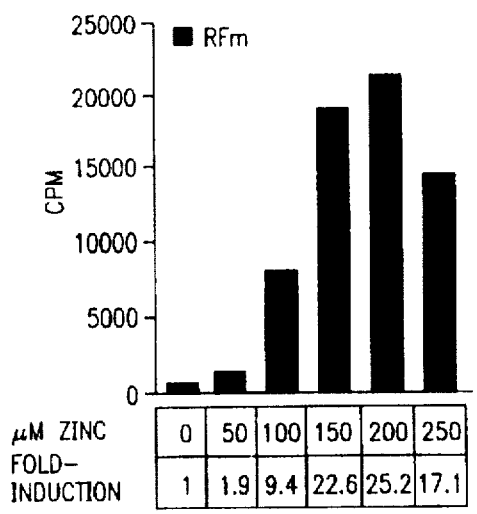
FIG. 5B is a bar graph plotting CPM of duplex monomer replicative form (RFm) of rAAV vs. the concentration of zinc (μM) used for induction and the fold-induction relative to 293(ORF6) cells maintained in 0 mM zinc below each bar.

The duplex monomer replicative form (RFm) was quantitated and the values (CPM) plotted along the vertical axis in the bar graph of FIG. 5B. The concentration of zinc used for induction and the fold-induction relative to 293(ORF6) cells maintained in 0 mM zinc is given below each bar.

The autoradiogram of FIG. 6 shows the agarose gel resolved Hirt extracts from the AV.CMVLacZ transduced cells described above. A plasmid carrying the AV.CMVLacZ cDNA was digested to release the entire sequence and loaded in the (M) lane. The band that appears in this lane therefore reflects the migration of a monomer duplex replicative form (RFm). The migration of the single-stranded AV.CMVLacZ genome (SS), RFm, and dimers of the duplex replicative form (RFd) are shown. Lanes labeled (0), (50), (100), (150), (200), and (250) contain samples from 293 (MT-ORF6) cells that were induced with the indicated concentration of zinc. A Hirt extract from 293 cells (lane labeled 293) transduced with AV.CMVLacZ is also shown.

Analysis of Hirt extracts revealed the presence of the RFm in the rAAV infected 293(MT-ORF6) cells that was not present in similarly infected 293 cells.

When the induction profiles (FIGS. 5A and 5B) that describe AV.CMVLacZ transduction efficiency were compared, the results were plotted in FIG. 5C. Specific activity (milliunits β-galactosidase/mg protein) data from FIG. 5A and counts-per-minute data (CPM) of AV.CMV-LacZ RFm from FIG. 5B are plotted along the vertical axis, and concentration of zinc sulfate used during the experiment is shown along the horizontal axis.

The two profiles are near mirror images. Importantly, the RFm increased in proportion to the increment in lacZ transducing activity that occurred as ORF-6 expression was induced with $Zn^{+2}$(Fig. 5C). Similar results were obtained with a 293 derived cell line that expresses ORF6 from the glucocorticoid responsive MMTV promoter.

Example 7—Enhanced AV.CMVLacZ Transduction in HeLa Cells Carrying an Inducible ORF6 Minigene HeLa(MT-ORF6) cells ($2\times10^6$) were transduced at an MOI of 1,000 AV.CMVLacZ recombinant virus particles/cell in the presence or absence of zinc inducer. Twenty-four hours later, cells were harvested, cell extracts were prepared by sonication, and analyzed for transgene expression (i.e., β-galactosidase activity). Cell monolayers were histochemically stained for β-galactosidase activity and the results illustrated in the photomicrographs of FIGS. 7A through 7F, which are labeled according to the concentration of zinc sulfate that was present in the media during transduction. Histochemical staining revealed an increase in the number of cells scored lacZ positive (FIG. 7A–7F) as the concentration of $Zn^{+2}$ in the medium was raised from 0 to 200 mM. Concentrations of 250 mM zinc were found to be toxic to the cells.

Figure 8:
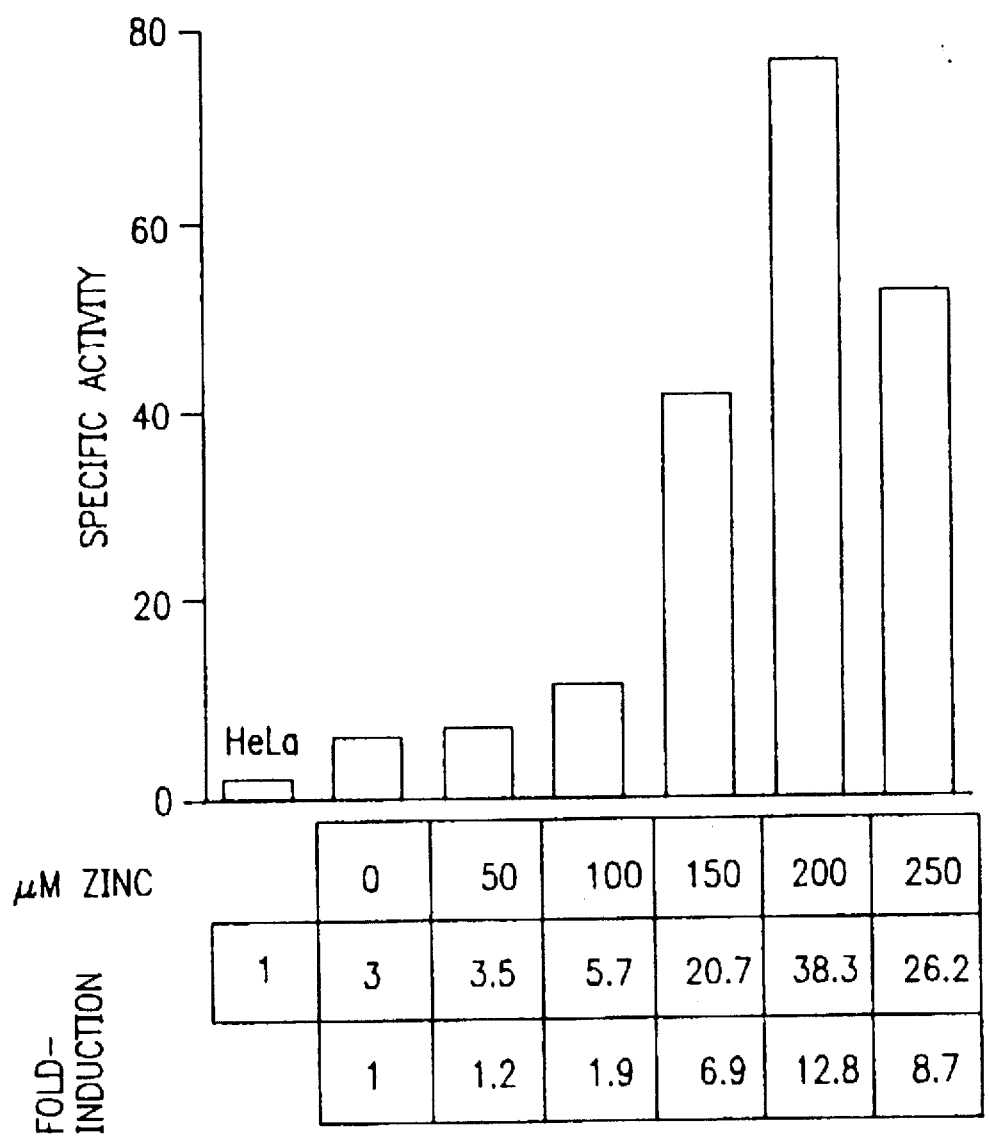
FIG. 8 is a bar graph plotting specific activity (milliunits β-galactosidase/mg protein) vs the concentration of zinc used for induction (first row under the horizontal axis), the fold-induction relative to HeLa cells (second row), and the fold-induction relative to HeLa(Mt-ORF6) cells maintained in the absence of zinc (third row), for the transduced cells of FIGS. 7A through 7F.

Specific activity (milliunits β-galactosidase/mg protein) is plotted in FIG. 8 along the vertical axis. Below each bar is given the concentration of zinc used for induction, the fold-induction relative to HeLa cells, and the fold-induction relative to HeLa(Mt-ORF6) cells maintained in the absence of zinc. Histochemical staining revealed an increase in the amount of β-galactosidase in lysates as the concentration of $Zn^{+2}$ in the medium was raised from 0 to 200 mM.

Example 8—Southern Blot Analysis of Low Molecular Weight DNAs from AV.CMVLacZ Transduced HeLa(MT-ORF6) Cells Following Induction of E40RF6

Hirt extracts were prepared from HeLa(MT-ORF6) cells transduced with AV.CMVLacZ as described in Example 7 in the presence of increasing concentrations of $Zn^{+2}$ to determine whether synthesis of duplex intermediates contributed to the augmentation in AV.CMVLacZ transduction.

Figure 9:
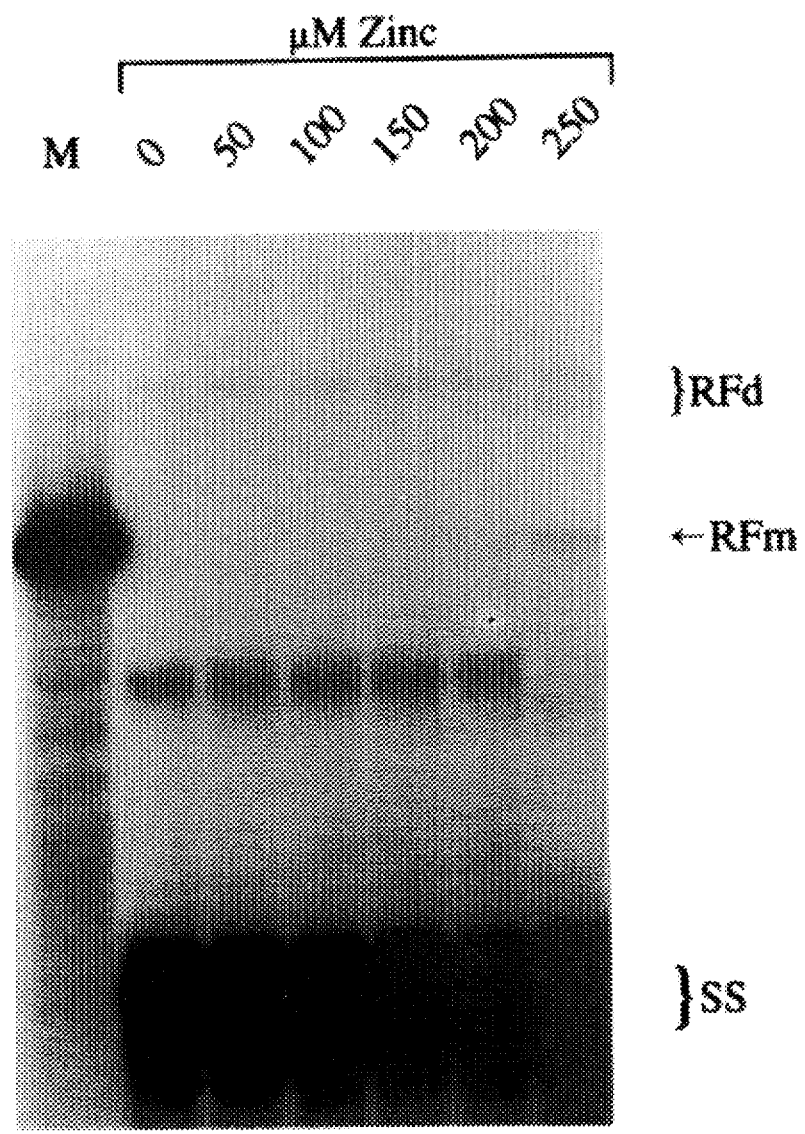
FIG. 9 is a Southern gel (1.2% agarose) showing hybridization with a LacZ-specific probe of samples from HeLa (MT-ORF6) cells that were induced with the indicated concentration of zinc (lanes labeled (0), (50), (100), (150), (200), and (250)). Lane (M) contains a plasmid encoding AV.CMVLacZ that was digested to release the entire genome. Bands corresponding to the single-stranded AV.CMVLacZ genome (SS), duplex monomers (RFm), and duplex dimers (RFd) are indicated.

Samples were resolved on a 1.2% agarose gel, transferred to a nylon membrane, and hybridized with a LacZ-specific probe. The results are illustrated in the gel of FIG. 9, in which lanes labeled (0), (50), (100), (150), (200), and (250) contain samples from HeLa(MT-ORF6) cells that were induced with the indicated concentration of zinc. Lane (M) contains a plasmid encoding AV.CMVLacZ that was digested to release the entire genome. Bands corresponding to the single-stranded AV.CMVLacZ genome (SS), duplex monomers (RFm), and duplex dimers (RFd) are indicated.

Southern analysis indicated that Hela and uninduced Hela(MT-ORF6) cells demonstrated a single band on Southern blots which comigrated with the single stranded genome (FIG. 9). Induction of ORF-6 resulted in the appearance of detectable levels of double stranded monomer but only at higher concentrations of Zn+2. A band comigrating with the RFd was present in all cell preparations, the relevance of which is unclear since the monomer is a likely precursor to the dimer.

Example 9—Effect of Adenovirus Infection on In Vivo AV.CMVLacZ Targeting Efficiency To Murine Liver The impact of adenoviral gene expression on rAAV transduction in murine liver was studied by sequentially infusing into the portal vein early gene mutants of adenovirus followed by rAAV.

Balb/c mice, 4- to 6-weeks old [Jackson Laboratories, Bar Harbor, Maine] were anesthetized by an intraperitoneal injection of ketamine (70 mg/kg) and xylazine (10 mg/kg). For liver studies, a 1 cm left flank incision was made and the spleen exposed.

Samples of purified, heat-treated AV.CMVLacZ in 50 μl HBS ($1\times10^{11}$ virus particles) were used alone or spiked with helper adenovirus containing $2\times10^{10}$ $A_{260}$ particles of purified dl1004, H5.CBALP, or ts125 in a final volume of 50 μl. The dose of adenovirus was sufficient to transduce >25% of hepatocytes. The virus mixture was injected just beneath the splenic capsule and the abdomen was closed with 3-0 vicryl.

Necropsies were performed 3 days post-infusion and tissue frozen in O.C.T. embedding compound. Frozen sections (6 μm) (LacZ+ALP) were prepared and histochemically stained for β-galactosidase enzyme and alkaline phosphatase activity. Sections were counterstained with neutral red and mounted.

A β-galactosidase positive hepatocyte targeted with AV.C-MVLacZ at magnification 20× was obtained. Histochemical analyses of liver tissue harvested 3 days after gene transfer demonstrated that administration of $10^{11}$ recombinant virus particles of purified rAV.CMVLacZ alone into the portal vein was not associated with appreciable gene transfer (<0.01% of cells), confirming the inherent inefficiency of the rAAV system.

Preinfusion with E4 deleted virus had no impact on rAAV transduction in mouse liver, whereas E1 deleted virus demonstrated a modest increment in lacZ positive hepatocytes to about 0.1%. The most significant increase in rAAV transduction occurred following infusion of the E2a adenovirus mutant ts125 with lacZ expression detected in 10–25% of hepatocytes. A direct relationship between adenovirus gene expression and rAAV transduction was demonstrated in animals infused with both lacZ rAAV and the ALP expressing E1 deleted virus. The dose of adenovirus was reduced 10-fold to minimize the coincidental occurrence of coinfection. Histochemical studies demonstrated co-localization of ALP and β-galactosidase in the majority of β-galactosidase expressing hepatocytes.

Example 10—Effect of Adenovirus Infection on In Vivo AV.CMVLacZ Targeting Efficiency To Murine Lung Experiments described in Example 9 for mouse liver were adapted for the study of rAAV mediated gene transfer to mouse lung. For lung experiments, anesthetized Balb/C animals were intubated as described in DeMatteo et al, *Transplantation (Baltimore)*, 59(5):787–789 (1995). Briefly, a midline 2 cm skin incision was made in the neck to expose the trachea. A 2 inch 18 gauge angiocatheter was passed through the mouth, positioned in the midportion of the trachea, and connected to a rodent ventilator (#55-3438 Harvard). Polyethylene (PE #10, Intramedic) was fed through the catheter via a side port and advanced beyond the tracheal bifurcation. Using a Hamilton syringe, virus samples (30 μl) were slowly infused into the lung through the polyethylene tubing. Samples contained the same formulation of purified, heat-treated AV.CMVLacZ with or without helper adenovirus, as described for liver injections.

Tissue was harvested 72 hours post-infusion. Frozen sections were histochemically stained for β-galactosidase activity and counterstained with neutral red.

Frozen sections from lung (AV.CMVLacZ) showed a β-galactosidase positive airway epithelial cell targeted with AV.CMVLacZ. Similar studies were performed in the murine model of lung-directed gene transfer. Adenoviruses were instilled into the trachea prior to the instillation of rAAV. Analysis of lung tissue 3 days later revealed only a rare β-galactosidase positive cell in animals instilled with rAAV alone. No detectable enhancement of rAAV transduction was noted in animals preinstilled with adenovirus deleted of either E1 or E4. Substantial enhancement of transduction was achieved in conducting airway and alveolar cells of animals administered the E2a mutant adenovirus.

These experiments in murine models of gene therapy directed to liver and lung verified that the efficiency of rAAV transduction is low due limited conversion of the input single stranded genome to a transcriptionally active double stranded intermediate, and that this conversion is facilitated by expression of adenovirus E1 and E4 gene products.

Example 11—Second Generation rAAV with Regulated Minigene Capable of Enhancing Transduction The experiments described in previous examples illustrated the following principles: 1) purified rAAV is a relatively inefficient gene transfer vehicle in vitro and in vivo and 2) the rate limiting step in transduction is not viral entry but rather conversion of the virion's single stranded DNA genome to a transcriptionally active double stranded DNA genome. Adenovirus can substantially enhance transduction through expression of a subset of its genes. It does this by promoting conversion of the virion's genome to its double stranded form. One approach to accomplish this is to incorporate into the recombinant AAV genome a minigene that expresses the minimal adenoviral genes necessary to enhance transduction, i.e., the ORF6 region of E4.

Two approaches have been considered in designing this modified rAAV. The first strategy is based on a rAAV genome that has two transcriptional units in series, one expressing the therapeutic gene and the other expressing its E4 ORF6 from a constitutive promoter. While this may, in fact, be useful in many situations, constitutive expression of ORF6 may be detrimental to the cell and potentially could elicit a destructive immune response.

The second version of this recombinant virus includes the therapeutic minigene in addition to the ORF6 transcriptional unit which, in this case, is expressed from an inducible promoter. When this second gene rAAV is administered to the cells (ex vivo strategies) or to the patient (in vivo strategies), the inducing agents are administered at the time of gene transfer or soon thereafter. If the ds genomic form or its integrated derivative is stable, the induction of ORF6 will only be necessary at the time of gene transfer into the recipient cell. Following this, its inducing agent will be withdrawn and the ORF6 gene will be turned off.

Figure 13:
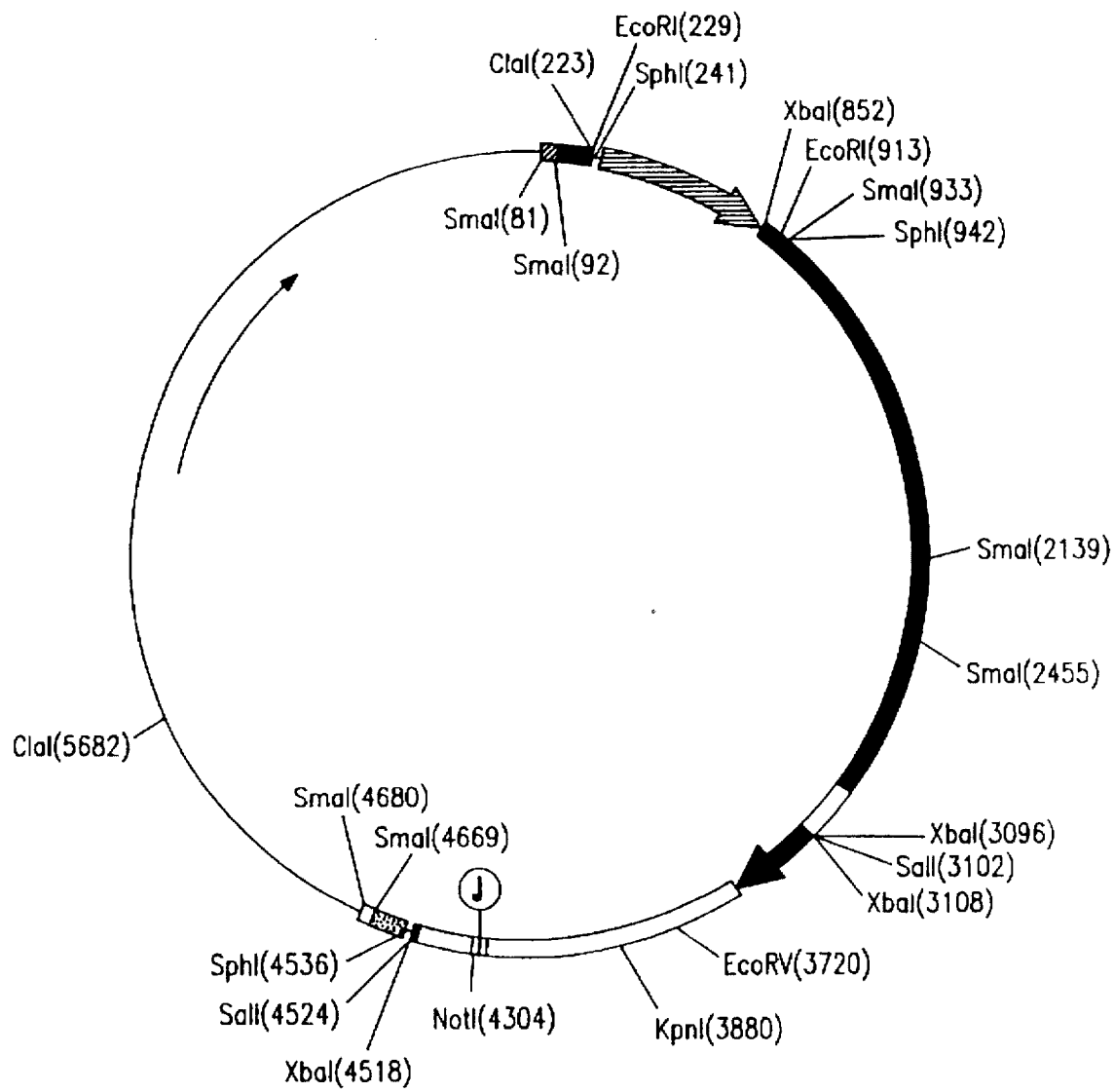
FIG. 13 is a schematic of the plasmid pAV.CMVALP.GRE-ORF6.

An rAAV that illustrates this concept of inducible ORF6 has been constructed and tested in vitro. A schematic of the vector is shown in FIG. 13 and its sequence [SEQ ID NO:2] is illustrated in FIG. 12. The vector is flanked by AAV ITRs. The human placental alkaline phosphatase cDNA (ALP) is included in a minigene in which the promoter from the immediate early gene of cytomegalovirus drives the transcription. A second transcriptional unit is cloned between the ITRs in series and in direct orientation with the alkaline phosphatase minigene. The second transcriptional unit expresses the Ad5-E4-ORF6 from a glucocorticoid dependent promoter (GRE) with an SV40 polyadenylation signal. This is called a second generation rAAV construct.

The second generation rAAV construct was used to produce and purify rAAV virions which were exposed to HeLa cells that were left untreated or incubated with dexamethasone. In the absence of dexamethasone, (a condition under which little ORF6 should be expressed), little transduction was observed as measured by expression of the alkaline phosphatase gene. Cells incubated in dexamethasone expressed in ORF6 gene and the transduction efficacy was enhanced at least 5-fold. This provides evidence to support that a gene product expressed from the rAAV can function in cis to enhance expression of the transgene.

Example 12—Application to Bone Marrow Directed Gene Therapy

Bone marrow directed gene therapy represents the paradigm of ex vivo gene therapy where the target cell is the hematopoietic stem cell. The basic strategy is to incorporate (i.e., integrate) a therapeutic minigene into the chromosomal DNA of hematopoietic stem cells which are transplanted into a recipient patient whose own bone marrow has been ablated allowing repopulation of its lymphohematopoietic system with progeny of the genetically corrected stem cell.

The problem with this approach has been efficiently transfecting genes into stem cells. Most studies of bone marrow directed gene therapy have utilized recombinant retroviruses which have not been very efficient. One problem is that retroviruses integrate their provirus only when the target cell is dividing. Unfortunately, most stem cells in vitro are quiescent and not dividing. rAAV holds the promise of integrating the provirus more efficiently into non-dividing stem cells. However, purified rAAV is not very efficient with respect to integration when used alone. In cultured cells, integration is observed in less than 1% of the cells. The same conditions that activate the conversion of single stranded to double stranded genome also enhance the integration of the double stranded intermediate into the chromosomal DNA. Therefore, a desirable application of the methods and compositions of this invention is in bone marrow directed gene therapy where stem cells are genetically modified with rAAV and an inducing agent ex vivo and subsequently transplanted.

All publications identified herein are incorporated by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method for enhancing the efficiency of transduction by a recombinant adeno-associated virus (rAAV) comprising the steps of:
    infecting a target cell with a rAAV essentially free of contamination with helper virus, said rAAV comprising: (a) AAV inverted terminal repeat sequences necessary for transduction; and (b) a selected gene operatively linked to regulatory sequences directing its expression, wherein said gene is flanked by the DNA of (a); and
    introducing into said target cell an agent which delivers an adenovirus E4 open reading frame 6 (ORF 6) gene product to said target cell, said agent selected from the group consisting of a recombinant virus and a recombinant DNA molecule comprising a DNA sequence operatively linked to regulatory sequences which direct expression of said E4 ORF 6 gene product in said target cell thereby enhancing transduction efficiency of the rAAV.

2. The method according to claim 1 wherein said agent further delivers an adenovirus E1 gene product to said target cell.

3. The method according to claim 1 wherein said agent is a recombinant virus.

4. The method according to claim 3 wherein said recombinant virus expresses an adenovirus E1 gene product.

5. The method according to claim 3 or 4 wherein said recombinant virus is an adenovirus.

6. The method according to claim 3 wherein said recombinant virus expresses an adenovirus E4 gene product consisting of ORF 6.

7. The method according to claim 1 wherein said DNA molecule further comprises a DNA sequence encoding an adenovirus E1 gene product, said DNA sequence operatively linked to regulatory sequences which direct expression of said E1 gene product in said target cell.

8. The method according to claim 1 or 8 wherein said regulatory sequences directing expression of said adenovirus E4 gene product and/or said E1 gene product comprise a constitutive promoter.

9. The method according to claim 1 or 8 wherein said regulatory sequences directing expression of said adenovirus E4 gene product and/or said adenovirus E1 gene product comprise an inducible promoter and wherein said cells are exposed to an inducing agent.

10. A method for enhancing the efficiency of transduction of a target cell by a rAAV comprising the step of infecting said target cell with said rAAV essentially free of contamination with helper virus, said rAAV comprising: (a) AAV inverted terminal repeat sequences necessary for transduction; (b) a selected gene operatively linked to regulatory sequences directing its expression; and (c) an adenovirus E4 gene sequence operatively linked to regulatory sequences which direct expression of an adenovirus E4 ORF 6 gene product, wherein said selected gene and said E4 gene sequence are flanked by the sequences of (a) thereby enhancing transduction efficiency of the rAAV.

11. The method according to claim 10, wherein said rAAV further comprises an adenovirus E1 gene sequence operatively linked to regulatory sequences which direct expression of an adenovirus E1 gene product, said selected, E4 and E1 gene sequences flanked by the sequences of (a).

12. The method according to claim 10 wherein said E4 gene sequence consists of an ORF 6 sequence.

13. The method according to claim 11 wherein said regulatory sequences directing expression of said E1 gene product comprise an inducible promoter, and wherein said cell is exposed to an inducing agent.

14. The method according to claim 11 wherein said regulatory sequences directing expression of said adenovirus E1 gene product comprise a constitutive promoter.

15. The method according to claim 10 wherein said regulatory sequences directing expression of said adenovirus E4 ORF 6 gene product comprise an inducible promoter, and wherein said cell is exposed to an inducing agent.

16. The method according to claim 10 wherein said regulatory sequences directing expression of said adenovirus E4 gene product comprise a constitutive promoter.

17. A recombinant adeno-associated virus (rAAV) comprising:
   (a) AAV inverted terminal repeats sequences necessary for transduction;
   (b) a selected gene operatively linked to regulatory sequences directing its expression,
   (c) an adenovirus E4 gene sequence operatively linked to regulatory sequences which direct expression of an adenovirus E4 open reading frame 6 (ORF 6 ) gene product,
   said selected gene and said adenovirus E4 gene sequence flanked by the sequences of (a).

18. The rAAV according to claim 17 wherein said adenovirus E4 gene sequence consists of ORF 6.

19. The rAAV according to claim 17 wherein said regulatory sequences directing expression of said adenovirus E4 gene product comprise an inducible promoter.

20. The rAAV according to claim 17 wherein said regulatory sequences directing expression of said adenovirus E4 gene product comprise a constitutive promoter.

21. The rAAV according to claim 17 further comprising an adenovirus E1 gene sequence operatively linked to regulatory sequences which direct expression of an E1 gene product, said selected, E4, and E1 gene sequences flanked by the sequences of (a).

22. The rAAV according to claim 21 wherein said regulatory sequences directing expression of said E1 gene product comprise an inducible promoter.

23. The rAAV according to claim 21 wherein said regulatory sequences directing expression of said E1 gene product comprise a constitutive promoter.

\* \* \* \* \*

UNITED STATES PATENT AND TRADEMARK OFFICE
CERTIFICATE OF CORRECTION

PATENT NO. : 5,756,283
DATED : May 26, 1998
INVENTOR(S) : James M. Wilson, Krishna J. Fisher, and Guang-Ping Gao It is certified that error appears in the above-identified patent and that said Letters Patent is hereby corrected as shown below:

On the cover page, in the title [54], delete the title "Method for Improved Production of Recombinant Adeno-Associated Viruses for Gene Therapy" and insert in place thereof -- Method for Improved Transduction by Recombinant Adeno-Associated Viruses --.

Col. 5, line 36, delete "Fig. 10" and insert in place thereof -- Figs. 10A-10E --.

Col. 5, line 45, delete "Fig. 12" and insert in place thereof -- Figs. 12A-12E --.

Col. 13, line 65, delete "Forth" and insert in place thereof -- Forty --.

Signed and Sealed this

Sixth Day of July, 1999

*Attest:*

Q. TODD DICKINSON

*Attesting Officer*   Acting Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 8509 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:1:

| | | | | | | |
|---|---|---|---|---|---|---|
| GCCCAATACG | CAAACCGCCT | CTCCCCGCGC | GTTGGCCGAT | TCATTAATGC | AGCTGCGCGC | 60 |
| TCGCTCGCTC | ACTGAGGCCG | CCCGGGCAAA | GCCCGGGCGT | CGGGCGACCT | TTGGTCGCCC | 120 |
| GGCCTCAGTG | AGCGAGCGAG | CGCGCAGAGA | GGGAGTGGCC | AACTCCATCA | CTAGGGGTTC | 180 |
| CTTGTAGTTA | ATGATTAACC | CGCCATGCTA | CTTATCTACG | TAGCCATTCT | CTAGCCCTG | 240 |
| CAGGTCGTTA | CATAACTTAC | GGTAAATGGC | CCGCCTGGCT | GACCGCCCAA | CGACCCCGC | 300 |
| CCATTGACGT | CAATAATGAC | GTATGTTCCC | ATAGTAACGC | CAATAGGGAC | TTTCCATTGA | 360 |
| CGTCAATGGG | TGGAGTATTT | ACGGTAAACT | GCCCACTTGG | CAGTACATCA | AGTGTATCAT | 420 |
| ATGCCAAGTA | CGCCCCCTAT | TGACGTCAAT | GACGGTAAAT | GGCCCGCCTG | GCATTATGCC | 480 |
| CAGTACATGA | CCTTATGGGA | CTTTCCTACT | TGGCAGTACA | TCTACGTATT | AGTCATCGCT | 540 |
| ATTACCATGG | TGATGCGGTT | TTGGCAGTAC | ATCAATGGGC | GTGGATAGCG | GTTTGACTCA | 600 |
| CGGGGATTTC | CAAGTCTCCA | CCCCATTGAC | GTCAATGGGA | GTTTGTTTTG | CACCAAAAT | 660 |
| CAACGGGACT | TTCCAAAATG | TCGTAACAAC | TCCGCCCCAT | TGACGCAAAT | GGGCGGTAGG | 720 |
| CGTGTACGGT | GGGAGGTCTA | TATAAGCAGA | GCTCGTTTAG | TGAACCGTCA | GATCGCCTGG | 780 |
| AGACGCCATC | CACGCTGTTT | TGACCTCCAT | AGAAGACACC | GGGACCGATC | CAGCCTCCGG | 840 |
| ACTCTAGAGG | ATCCGGTACT | CGAGGAACTG | AAAAACCAGA | AAGTTAACTG | GTAAGTTTAG | 900 |
| TCTTTTTGTC | TTTTATTTCA | GGTCCCGGAT | CCGGTGGTGG | TGCAAATCAA | AGAACTGCTC | 960 |
| CTCAGTGGAT | GTTGCCTTTA | CTTCTAGGCC | TGTACGGAAG | TGTTACTTCT | GCTCTAAAAG | 1020 |
| CTGCGGAATT | GTACCCGCGG | CCGCAATTCC | CGGGGATCGA | AAGAGCCTGC | TAAAGCAAAA | 1080 |
| AAGAAGTCAC | CATGTCGTTT | ACTTTGACCA | ACAAGAACGT | GATTTCGTT | GCCGGTCTGG | 1140 |
| GAGGCATTGG | TCTGGACACC | AGCAAGGAGC | TGCTCAAGCG | CGATCCCGTC | GTTTTACAAC | 1200 |
| GTCGTGACTG | GGAAAACCCT | GGCGTTACCC | AACTTAATCG | CCTTGCAGCA | CATCCCCCTT | 1260 |
| TCGCCAGCTG | GCGTAATAGC | GAAGAGGCCC | GCACCGATCG | CCCTTCCCAA | CAGTTGCGCA | 1320 |
| GCCTGAATGG | CGAATGGCGC | TTTGCCTGGT | TTCCGGCACC | AGAAGCGGTG | CCGGAAAGCT | 1380 |
| GGCTGGAGTG | CGATCTTCCT | GAGGCCGATA | CTGTCGTCGT | CCCCTCAAAC | TGGCAGATGC | 1440 |
| ACGGTTACGA | TGCGCCCATC | TACACCAACG | TAACCTATCC | CATTACGGTC | AATCCGCCGT | 1500 |
| TTGTTCCCAC | GGAGAATCCG | ACGGGTTGTT | ACTCGCTCAC | ATTTAATGTT | GATGAAAGCT | 1560 |
| GGCTACAGGA | AGGCCAGACG | CGAATTATTT | TTGATGGCGT | TAACTCGGCG | TTTCATCTGT | 1620 |
| GGTGCAACGG | GCGCTGGGTC | GGTTACGGCC | AGGACAGTCG | TTTGCCGTCT | GAATTTGACC | 1680 |
| TGAGCGCATT | TTTACGCGCC | GGAGAAAACC | GCCTCGCGGT | GATGGTGCTG | CGTTGGAGTG | 1740 |
| ACGGCAGTTA | TCTGGAAGAT | CAGGATATGT | GGCGGATGAG | CGGCATTTTC | CGTGACGTCT | 1800 |

```
CGTTGCTGCA TAAACCGACT ACACAAATCA GCGATTTCCA TGTTGCCACT CGCTTTAATG     1860
ATGATTTCAG CCGCGCTGTA CTGGAGGCTG AAGTTCAGAT GTGCGGCGAG TTGCGTGACT     1920
ACCTACGGGT AACAGTTTCT TTATGGCAGG GTGAAACGCA GGTCGCCAGC GGCACCGCGC     1980
CTTTCGGCGG TGAAATTATC GATGAGCGTG GTGGTTATGC CGATCGCGTC ACACTACGTC     2040
TGAACGTCGA AAACCCGAAA CTGTGGAGCG CCGAAATCCC GAATCTCTAT CGTGCGGTGG     2100
TTGAACTGCA CACCGCCGAC GGCACGCTGA TTGAAGCAGA AGCCTGCGAT GTCGGTTTCC     2160
GCGAGGTGCG GATTGAAAAT GGTCTGCTGC TGCTGAACGG CAAGCCGTTG CTGATTCGAG     2220
GCGTTAACCG TCACGAGCAT CATCCTCTGC ATGGTCAGGT CATGGATGAG CAGACGATGG     2280
TGCAGGATAT CCTGCTGATG AAGCAGAACA ACTTTAACGC CGTGCGCTGT TCGCATTATC     2340
CGAACCATCC GCTGTGGTAC ACGCTGTGCG ACCGCTACGG CCTGTATGTG GTGGATGAAG     2400
CCAATATTGA AACCCACGGC ATGGTGCCAA TGAATCGTCT GACCGATGAT CCGCGCTGGC     2460
TACCGGCGAT GAGCGAACGC GTAACGCGAA TGGTGCAGCG CGATCGTAAT CACCCGAGTG     2520
TGATCATCTG GTCGCTGGGG AATGAATCAG GCCACGGCGC TAATCACGAC GCGCTGTATC     2580
GCTGGATCAA ATCTGTCGAT CCTTCCCGCC CGGTGCAGTA TGAAGGCGGC GGAGCCGACA     2640
CCACGGCCAC CGATATTATT TGCCCGATGT ACGCGCGCGT GGATGAAGAC CAGCCCTTCC     2700
CGGCTGTGCC GAAATGGTCC ATCAAAAAAT GGCTTTCGCT ACCTGGAGAG ACGCGCCCGC     2760
TGATCCTTTG CGAATACGCC CACGCGATGG GTAACAGTCT TGGCGGTTTC GCTAAATACT     2820
GGCAGGCGTT TCGTCAGTAT CCCCGTTTAC AGGGCGGCTT CGTCTGGGAC TGGGTGGATC     2880
AGTCGCTGAT TAAATATGAT GAAAACGGCA ACCCGTGGTC GGCTTACGGC GGTGATTTTG     2940
GCGATACGCC GAACGATCGC CAGTTCTGTA TGAACGGTCT GGTCTTTGCC GACCGCACGC     3000
CGCATCCAGC GCTGACGGAA GCAAACACC AGCAGCAGTT TTTCCAGTTC CGTTTATCCG     3060
GGCAAACCAT CGAAGTGACC AGCGAATACC TGTTCCGTCA TAGCGATAAC GAGCTCCTGC     3120
ACTGGATGGT GGCGCTGGAT GGTAAGCCGC TGGCAAGCGG TGAAGTGCCT CTGGATGTCG     3180
CTCCACAAGG TAAACAGTTG ATTGAACTGC CTGAACTACC GCAGCCGGAG AGCGCCGGGC     3240
AACTCTGGCT CACAGTACGC GTAGTGCAAC CGAACGCGAC CGCATGGTCA GAAGCGGGC     3300
ACATCAGCGC CTGGCAGCAG TGGCGTCTGG CGGAAAACCT CAGTGTGACG CTCCCCGCCG     3360
CGTCCCACGC CATCCCGCAT CTGACCACCA GCGAAATGGA TTTTTGCATC GAGCTGGGTA     3420
ATAAGCGTTG GCAATTTAAC CGCCAGTCAG GCTTTCTTTC ACAGATGTGG ATTGGCGATA     3480
AAAAACAACT GCTGACGCCG CTGCGCGATC AGTTCACCCG TGCACCGCTG ATAACGACA     3540
TTGGCGTAAG TGAAGCGACC CGCATTGACC CTAACGCCTG GGTCGAACGC TGGAAGGCGG     3600
CGGGCCATTA CCAGGCCGAA GCAGCGTTGT TGCAGTGCAC GGCAGATACA CTTGCTGATG     3660
CGGTGCTGAT TACGACCGCT CACGCGTGGC AGCATCAGGG GAAAACCTTA TTTATCAGCC     3720
GGAAAACCTA CCGGATTGAT GGTAGTGGTC AAATGGCGAT TACCGTTGAT GTTGAAGTGG     3780
CGAGCGATAC ACCGCATCCG GCGCGGATTG GCCTGAACTG CCAGCTGGCG CAGGTAGCAG     3840
AGCGGGTAAA CTGGCTCGGA TTAGGGCCGC AAGAAAACTA TCCCGACCGC CTTACTGCCG     3900
CCTGTTTTGA CCGCTGGGAT CTGCCATTGT CAGACATGTA TACCCCGTAC GTCTTCCCGA     3960
GCGAAAACGG TCTGCGCTGC GGGACGCGCG AATTGAATTA TGCCCACAC CAGTGGCGCG     4020
GCGACTTCCA GTTCAACATC AGCCGCTACA GTCAACAGCA ACTGATGGAA ACCAGCCATC     4080
GCCATCTGCT GCACGCGGAA GAAGGCACAT GGCTGAATAT CGACGGTTTC CATATGGGGA     4140
TTGGTGGCGA CGACTCCTGG AGCCCGTCAG TATCGGCGGA ATTACAGCTG AGCGCCGGTC     4200
```

| | | | | | | |
|---|---|---|---|---|---|---|
| GCTACCATTA | CCAGTTGGTC | TGGTGTCAAA | AATAATAATA | ACCGGGCAGG | CCATGTCTGC | 4260 |
| CCGTATTTCG | CGTAAGGAAA | TCCATTATGT | ACTATTTAAA | AAACACAAAC | TTTTGGATGT | 4320 |
| TCGGTTTATT | CTTTTTCTTT | TACTTTTTTA | TCATGGGAGC | CTACTTCCCG | TTTTTCCCGA | 4380 |
| TTTGGCTACA | TGACATCAAC | CATATCAGCA | AAAGTGATAC | GGGTATTATT | TTTGCCGCTA | 4440 |
| TTTCTCTGTT | CTCGCTATTA | TTCCAACCGC | TGTTTGGTCT | GCTTCTGAC | AAACTCGGCC | 4500 |
| TCGACTCTAG | GCGGCCGCGG | GGATCCAGAC | ATGATAAGAT | ACATTGATGA | GTTGGACAA | 4560 |
| ACCACAACTA | GAATGCAGTG | AAAAAAATGC | TTTATTTGTG | AAATTTGTGA | TGCTATTGCT | 4620 |
| TTATTTGTAA | CCATTATAAG | CTGCAATAAA | CAAGTTAACA | ACAACAATTG | CATTCATTTT | 4680 |
| ATGTTTCAGG | TTCAGGGGGA | GGTGTGGGAG | GTTTTTTCGG | ATCCTCTAGA | GTCGACCTGC | 4740 |
| AGGGGCTAGA | ATGGCTACGT | AGATAAGTAG | CATGGCGGGT | TAATCATTAA | CTACAAGGAA | 4800 |
| CCCCTAGTGA | TGGAGTTGGC | CACTCCCTCT | CTGCGCGCTC | GCTCGCTCAC | TGAGGCCGGG | 4860 |
| CGACCAAAGG | TCGCCCGACG | CCCGGGCTTT | GCCCGGGCGG | CCTCAGTGAG | CGAGCGAGCG | 4920 |
| CGCAGCTGGC | GTAATAGCGA | AGAGGCCCGC | ACCGATCGCC | CTTCCCAACA | GTTGCGCAGC | 4980 |
| CTGAATGGCG | AATGGAATTC | CAGACGATTG | AGCGTCAAAA | TGTAGGTATT | CCATGAGCG | 5040 |
| TTTTTCCTGT | TGCAATGGCT | GGCGGTAATA | TTGTTCTGGA | TATTACCAGC | AAGGCCGATA | 5100 |
| GTTTGAGTTC | TTCTACTCAG | GCAAGTGATG | TTATTACTAA | TCAAAGAAGT | ATTGCGACAA | 5160 |
| CGGTTAATTT | GCGTGATGGA | CAGACTCTTT | TACTCGGTGG | CCTCACTGAT | TATAAAAACA | 5220 |
| CTTCTCAGGA | TTCTGGCGTA | CCGTTCCTGT | CTAAAATCCC | TTTAATCGGC | CTCCTGTTTA | 5280 |
| GCTCCCGCTC | TGATTCTAAC | GAGGAAAGCA | CGTTATACGT | GCTCGTCAAA | GCAACCATAG | 5340 |
| TACGCGCCCT | GTAGCGGCGC | ATTAAGCGCG | GCGGGTGTGG | TGGTTACGCG | CAGCGTGACC | 5400 |
| GCTACACTTG | CCAGCGCCCT | AGCGCCCGCT | CCTTTCGCTT | TCTTCCCTTC | CTTTCTCGCC | 5460 |
| ACGTTCGCCG | GCTTTCCCCG | TCAAGCTCTA | AATCGGGGGC | TCCCTTTAGG | GTTCCGATTT | 5520 |
| AGTGCTTTAC | GGCACCTCGA | CCCCAAAAAA | CTTGATTAGG | GTGATGGTTC | ACGTAGTGGG | 5580 |
| CCATCGCCCT | GATAGACGGT | TTTTCGCCCT | TTGACGTTGG | AGTCCACGTT | CTTTAATAGT | 5640 |
| GGACTCTTGT | TCCAAACTGG | AACAACACTC | AACCCTATCT | CGGTCTATTC | TTTTGATTTA | 5700 |
| TAAGGGATTT | TGCCGATTTC | GGCCTATTGG | TTAAAAAATG | AGCTGATTTA | ACAAAAATTT | 5760 |
| AACGCGAATT | TTAACAAAAT | ATTAACGTTT | ACAATTTAAA | TATTTGCTTA | TACAATCTTC | 5820 |
| CTGTTTTTGG | GGCTTTTCTG | ATTATCAACC | GGGGTACATA | TGATTGACAT | GCTAGTTTTA | 5880 |
| CGATTACCGT | TCATCGATTC | TCTTGTTTGC | TCCAGACTCT | CAGGCAATGA | CCTGATAGCC | 5940 |
| TTTGTAGAGA | CCTCTCAAAA | ATAGCTACCC | TCTCCGGCAT | GAATTTATCA | GCTAGAACGG | 6000 |
| TTGAATATCA | TATTGATGGT | GATTTGACTG | TCTCCGGCCT | TTCTCACCCG | TTTGAATCTT | 6060 |
| TACCTACACA | TTACTCAGGC | ATTGCATTTA | AAATATATGA | GGGTTCTAAA | AATTTTTATC | 6120 |
| CTTGCGTTGA | AATAAAGGCT | TCTCCCGCAA | AAGTATTACA | GGGTCATAAT | GTTTTTGGTA | 6180 |
| CAACCGATTT | AGCTTTATGC | TCTGAGGCTT | TATTGCTTAA | TTTTGCTAAT | TCTTTGCCTT | 6240 |
| GCCTGTATGA | TTTATTGGAT | GTTGGAATTC | CTGATGCGGT | ATTTTCTCCT | TACGCATCTG | 6300 |
| TGCGGTATTT | CACACCGCAT | ATGGTGCACT | CTCAGTACAA | TCTGCTCTGA | TGCCGCATAG | 6360 |
| TTAAGCCAGC | CCCGACACCC | GCCAACACCC | GCTGACGCGC | CCTGACGGGC | TTGTCTGCTC | 6420 |
| CCGGCATCCG | CTTACAGACA | AGCTGTGACC | GTCTCCGGGA | GCTGCATGTG | TCAGAGGTTT | 6480 |
| TCACCGTCAT | CACCGAAACG | CGCGAGACGA | AAGGGCCTCG | TGATACGCCT | ATTTTTATAG | 6540 |
| GTTAATGTCA | TGATAATAAT | GGTTTCTTAG | ACGTCAGGTG | GCACTTTTCG | GGGAAATGTG | 6600 |

```
CGCGGAACCC CTATTTGTTT ATTTTTCTAA ATACATTCAA ATATGTATCC GCTCATGAGA      6660
CAATAACCCT GATAAATGCT TCAATAATAT TGAAAAGGA  AGAGTATGAG TATTCAACAT     6720
TTCCGTGTCG CCCTTATTCC CTTTTTGCG  GCATTTGCC  TTCCTGTTTT TGCTCACCCA     6780
GAAACGCTGG TGAAAGTAAA AGATGCTGAA GATCAGTTGG GTGCACGAGT GGGTTACATC     6840
GAACTGGATC TCAACAGCGG TAAGATCCTT GAGAGTTTTC GCCCCGAAGA ACGTTTTCCA     6900
ATGATGAGCA CTTTTAAAGT TCTGCTATGT GGCGCGGTAT TATCCCGTAT TGACGCCGGG     6960
CAAGAGCAAC TCGGTCGCCG CATACACTAT TCTCAGAATG ACTTGGTTGA GTACTCACCA     7020
GTCACAGAAA AGCATCTTAC GGATGGCATG ACAGTAAGAG AATTATGCAG TGCTGCCATA     7080
ACCATGAGTG ATAACACTGC GGCCAACTTA CTTCTGACAA CGATCGGAGG ACCGAAGGAG     7140
CTAACCGCTT TTTTGCACAA CATGGGGGAT CATGTAACTC GCCTTGATCG TTGGGAACCG     7200
GAGCTGAATG AAGCCATACC AAACGACGAG CGTGACACCA CGATGCCTGT AGCAATGGCA     7260
ACAACGTTGC GCAAACTATT AACTGGCGAA CTACTTACTC TAGCTTCCCG GCAACAATTA     7320
ATAGACTGGA TGGAGGCGGA TAAAGTTGCA GGACCACTTC TGCGCTCGGC CCTTCCGGCT     7380
GGCTGGTTTA TTGCTGATAA ATCTGGAGCC GGTGAGCGTG GGTCTCGCGG TATCATTGCA     7440
GCACTGGGGC CAGATGGTAA GCCCTCCCGT ATCGTAGTTA TCTACACGAC GGGGAGTCAG     7500
GCAACTATGG ATGAACGAAA TAGACAGATC GCTGAGATAG GTGCCTCACT GATTAAGCAT     7560
TGGTAACTGT CAGACCAAGT TTACTCATAT ATACTTTAGA TTGATTTAAA ACTTCATTTT     7620
TAATTTAAAA GGATCTAGGT GAAGATCCTT TTTGATAATC TCATGACCAA AATCCCTTAA     7680
CGTGAGTTTT CGTTCCACTG AGCGTCAGAC CCCGTAGAAA AGATCAAAGG ATCTTCTTGA     7740
GATCCTTTTT TTCTGCGCGT AATCTGCTGC TTGCAAACAA AAAAACCACC GCTACCAGCG     7800
GTGGTTTGTT TGCCGGATCA AGAGCTACCA ACTCTTTTTC GAAGGTAAC  TGGCTTCAGC     7860
AGAGCGCAGA TACCAAATAC TGTCCTTCTA GTGTAGCCGT AGTTAGGCCA CCACTTCAAG     7920
AACTCTGTAG CACCGCCTAC ATACCTCGCT CTGCTAATCC TGTTACCAGT GGCTGCTGCC     7980
AGTGGCGATA AGTCGTGTCT TACCGGGTTG GACTCAAGAC GATAGTTACC GGATAAGGCG     8040
CAGCGGTCGG GCTGAACGGG GGGTTCGTGC ACACAGCCCA GCTTGGAGCG AACGACCTAC     8100
ACCGAACTGA GATACCTACA GCGTGAGCTA TGAGAAAGCG CCACGCTTCC CGAAGGGAGA     8160
AAGGCGGACA GGTATCCGGT AAGCGGCAGG GTCGGAACAG GAGAGCGCAC GAGGGAGCTT     8220
CCAGGGGGAA ACGCCTGGTA TCTTTATAGT CCTGTCGGGT TTCGCCACCT CTGACTTGAG     8280
CGTCGATTTT TGTGATGCTC GTCAGGGGG  CGGAGCCTAT GGAAAAACGC CAGCAACGCG     8340
GCCTTTTTAC GGTTCCTGGC CTTTTGCTGG CCTTTTGCTC ACATGTTCTT TCCTGCGTTA     8400
TCCCCTGATT CTGTGGATAA CCGTATTACC GCCTTTGAGT GAGCTGATAC CGCTCGCCGC     8460
AGCCGAACGA CCGAGCGCAG CGAGTCAGTG AGCGAGGAAG CGGAAGAGC               8509
```

( 2 ) INFORMATION FOR SEQ ID NO:2:

( i ) SEQUENCE CHARACTERISTICS:
        ( A ) LENGTH: 8299 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:2:

```
GCCCAATACG CAAACCGCCT CTCCCCGCGC GTTGGCCGAT TCATTAATGC AGCTGCGCGC       60
TCGCTCGCTC ACTGAGGCCG CCCGGGCAAA GCCCGGGCGT CGGGCGACCT TTGGTCGCCC      120
```

-continued

```
GGCCTCAGTG AGCGAGCGAG CGCGCAGAGA GGGAGTGGCC AACTCCATCA CTAGGGGTTC    180
CTTGTAGTTA ATGATTAACC CGCCATGCTA CTTATCTACA TCATCGATGA ATTCGAGCTT    240
GCATGCCTGC AGGTCGTTAC ATAACTTACG GTAAATGGCC CGCCTGGCTG ACCGCCCAAC    300
GACCCCCGCC CATTGACGTC AATAATGACG TATGTTCCCA TAGTAACGCC AATAGGGACT    360
TTCCATTGAC GTCAATGGGT GGAGTATTTA CGGTAAACTG CCCACTTGGC AGTACATCAA    420
GTGTATCATA TGCCAAGTAC GCCCCCTATT GACGTCAATG ACGGTAAATG GCCCGCCTGG    480
CATTATGCCC AGTACATGAC CTTATGGGAC TTTCCTACTT GGCAGTACAT CTACGTATTA    540
GTCATCGCTA TTACCATGGT GATGCGGTTT TGGCAGTACA TCAATGGGCG TGGATAGCGG    600
TTTGACTCAC GGGGATTTCC AAGTCTCCAC CCCATTGACG TCAATGGGAG TTTGTTTTGG    660
CACCAAAATC AACGGGACTT TCCAAAATGT CGTAACAACT CCGCCCCATT GACGCAAATG    720
GGCGGTAGGC GTGTACGGTG GGAGGTCTAT ATAAGCAGAG CTCGTTTAGT GAACCGTCAG    780
ATCGCCTGGA GACGCCATCC ACGCTGTTTT GACCTCCATA GAAGACACCG GACCGATCC    840
AGCCTCCGGA CTCTAGAGGA TCCGGTACTC GACCCGAGCT CGGATCCACT AGTAACGGCC    900
GCCAGTGTGC TGGAATTCTG CACTCCAGGC TGCCCGGGTT TGCATGCTGC TGCTGCTGCT    960
GCTGCTGGGC CTGAGGCTAC AGCTCTCCCT GGGCATCATC CTAGTTGAGG AGGAGAACCC   1020
GGACTTCTGG AACCGCGAGG CAGCCGAGGC CCTGGGTGCC GCCAAGAAGC TGCAGCCTGC   1080
ACAGACAGCC GCCAAGAACC TCATCATCTT CCTGGGCGAT GGGATGGGGG TGTCTACGGT   1140
GACAGCTGCC AGGATCCTAA AAGGGCAGAA GAAGGACAAA CTGGGGCCTG AGATACCCCT   1200
GGCCATGGAC CGCTTCCCAT ATGTGGCTCT GTCCAAGACA TACAATGTAG ACAAACATGT   1260
GCCAGACAGT GGAGCCACAG CCACGGCCTA CCTGTGCGGG GTCAAGGGCA ACTTCCAGAC   1320
CATTGGCTTG AGTGCAGCCG CCCGCTTTAA CCAGTGCAAC ACGACACGCG CAACGAGGT    1380
CATCTCCGTG ATGAATCGGG CCAAGAAAGC AGGGAAGTCA GTGGGAGTGG TAACCACCAC   1440
ACGAGTGCAG CACGCCTCGC CAGCCGGCAC CTACGCCCAC ACGGTGAACC GCAACTGGTA   1500
CTCGGACGCC GACGTGCCTG CCTCGGCCCG CCAGGAGGGG TGCCAGGACA TCGCTACGCA   1560
GCTCATCTCC AACATGGACA TTGATGTGAT CCTAGGTGGA GGCCGAAAGT ACATGTTTCG   1620
CATGGGAACC CCAGACCCTG AGTACCCAGA TGACTACAGC CAAGGTGGGA CCAGGCTGGA   1680
CGGGAAGAAT CTGGTGCAGG AATGGCTCGG CGAACGCCAG GGTGCCCGGT ACGTGTGGAA   1740
CCGCACTGAG CTCATGCAGG CTTCCCTGGA CCCGTCTGTG ACCCATCTCA TGGGTCTCTT   1800
TGAGCCTGGA GACATGAAAT ACGAGATCCA CCGAGACTCC ACACTGGACC CTCCCCTGAT   1860
GGAGATGACA GAGGCTGCCC TGCGCCTGCT GAGCAGACAC CCCCGCGGCT TCTTCCTCTT   1920
CGTGGAGGGT GGTCGCATCG ACCATGGTCA TCATGAAAGC AGGGCTTACC GGGCACTGAC   1980
TGAGACGATC ATGTTCGACG ACGCCATTGA GAGGCGGGC CAGCTCACCA GCGAGGAGGA   2040
CACGCTGAGC CTCGTCACTG CCGACCACTC CCACGTCTTC TCCTTCGGAG GCTACCCCCT   2100
GCGAGGGAGC TCCTTCATCG GGCTGGCCGC TGGCAAGGCC CGGGACAGGA AGGCCTACAC   2160
GGTCCTCCTA TACGGAAACG GTCCAGGCTA TGTGCTCAAG GACGGCGCCC GGCCGGATGT   2220
TACCGAGAGC GAGAGCGGGA GCCCCGAGTA TCGGCAGCAG TCAGCAGTGC CCCTGGACGA   2280
AGAGACCCAC GCAGGCGAGG ACGTGGCGGT GTTCGCGCGC GGCCCGCAGG CGCACCTGGT   2340
TCACGGCGTG CAGGAGCAGA CCTTCATAGC GCACGTCATG GCCTTCGCCG CCTGCCTGGA   2400
GCCCTACACC GCCTGCGACC TGGCGCCCCC CGCCGGCACC ACCGACGCCG CGCACCCGGG   2460
GCGGTCCGTG GTCCCCGCGT TGCTTCCTCT GCTGGCCGGG ACCCTGCTGC TGCTGGAGAC   2520
```

```
GGCCACTGCT CCCTGAGTGT CCCGTCCCTG GGGCTCCTGC TTCCCCATCC CGGAGTTCTC    2580
CTGCTCCCCA CCTCCTGTCG TCCTGCCTGG CCTCCAGCCC GAGTCGTCAT CCCCGGAGTC    2640
CCTATACAGA GGTCCTGCCA TGGAACCTTC CCCTCCCCGT GCGCTCTGGG GACTGAGCCC    2700
ATGACACCAA ACCTGCCCCT GGCTGCTCT  CGGACTCCCT ACCCCAACCC CAGGGACTGC    2760
AGGTTGTGCC CTGTGGCTGC CTGCACCCCA GGAAGGAGG  GGGCTCAGGC CATCCAGCCA    2820
CCACCTACAG CCCAGTGGGG TCGAGACAGA TGGTCAGTCT GGAGGATGAC GTGGCGTGAA    2880
GCTGGCCGCG GGGATCCAGA CATGATAAGA TACATTGATG AGTTTGGACA AACCACAACT    2940
AGAATGCAGT GAAAAAAATG CTTTATTTGT GAAATTTGTG ATGCTATTGC TTTATTTGTA    3000
ACCATTATAA GCTGCAATAA ACAAGTTAAC AACAACAATT GCATTCATTT TATGTTTCAG    3060
GTTCAGGGGG AGGTGTGGGA GGTTTTTTCG GATCCTCTAG AGTCGACTCT AGANNNNNNN    3120
NNNNNNNNNN NNNNNNNNNN NNNNNNNNNN NNNNNNNNNN NNNNNNNNNN NNNNNNNNNN    3180
NNNNNNNNNN NNNNNNNNNN NNNNNNNNNN NNNNNNNNNN NNNNNNNNNN NNNNNNNNNN    3240
NNNNNNNNNN NNNNNNNNNN NNNNNNNNNN NNNNNNNNNN NNNNNNNNNN NNNNNNNNNN    3300
NNNNNNNNNN NNNNNNNNNN NNNNNNNNNN NNNNNNNNNN NNNNNNNNNN NNNNNNNNNN    3360
NNNNNNNNNN NNNNNNNNNN NNNNNNNNNN NNNGGATCCC CATGACTACG TCCGGCGTTC    3420
CATTTGGCAT GACACTACGA CCAACACGAT CTCGGTTGTC TCGGCGCACT CCGTACAGTA    3480
GGGATCGTCT ACCTCCTTTT GAGACAGAAA CCCGCGCTAC CATACTGGAG GATCATCCGC    3540
TGCTGCCCGA ATGTAACACT TTGACAATGC ACAACGTGAG TTACGTGCGA GGTCTTCCCT    3600
GCAGTGTGGG ATTTACGCTG ATTCAGGAAT GGGTTGTTCC CTGGGATATG GTTCTAACGC    3660
GGGAGGAGCT TGTAATCCTG AGGAAGTGTA TGCACGTGTG CCTGTGTTGT GCCAACATTG    3720
ATATCATGAC GAGCATGATG ATCCATGGTT ACGAGTCCTG GCTCTCCAC  TGTCATTGTT    3780
CCAGTCCCGG TTCCCTGCAG TGTATAGCCG GCGGGCAGGT TTTGGCCAGC TGGTTTAGGA    3840
TGGTGGTGGA TGGCGCCATG TTTAATCAGA GGTTTATATG GTACCGGGAG GTGGTGAATT    3900
ACAACATGCC AAAAGAGGTA ATGTTTATGT CCAGCGTGTT TATGAGGGGT CGCCACTTAA    3960
TCTACCTGCG CTTGTGGTAT GATGGCCACG TGGGTTCTGT GGTCCCGCC  ATGAGCTTTG    4020
GATACAGCGC CTTGCACTGT GGGATTTTGA ACAATATTGT GGTGCTGTGC TGCAGTTACT    4080
GTGCTGATTT AAGTGAGATC AGGGTGCGCT GCTGTGCCCG GAGGACAAGG CGCCTTATGC    4140
TGCGGGCGGT GCGAATCATC GCTGAGGAGA CCACTGCCAT GTTGTATTCC TGCAGGACGG    4200
AGCGGCGGCG GCAGCAGTTT ATTCGCGCGC TGCTGCAGCA CCACCGCCCT ATCCTGATGC    4260
ACGATTATGA CTCTACCCCC ATGTAGGGAT CCCCATCACT AGTGCGGCCG CGGGGATCCA    4320
GACATGATAA GATACATTGA TGAGTTTGGA CAAACCACAA CTAGAATGCA GTGAAAAAAA    4380
TGCTTTATTT GTGAAATTTG TGATGCTATT GCTTTATTTG TAACCATTAT AAGCTGCAAT    4440
AAACAAGTTA ACAACAACAA TTGCATTCAT TTATGTTTC  AGGTTCAGGG GGAGGTGTGG    4500
GAGGTTTTTT CGGATCCTCT AGAGTCGACC TGCAGGCATG CAAGCTGTAG ATAAGTAGCA    4560
TGGCGGGTTA ATCATTAACT ACAAGGAACC CCTAGTGATG GAGTTGGCCA CTCCCTCTCT    4620
GCGCGCTCGC TCGCTCACTG AGGCCGGGCG ACCAAAGGTC GCCCGACGCC CGGGCTTTGC    4680
CCGGGCGGCC TCAGTGAGCG AGCGAGCGCG CAGCTGGCGT AATAGCGAAG AGGCCCGCAC    4740
CGATCGCCCT TCCCAACAGT TGCGCAGCCT GAATGGCGAA TGGAANTTCC AGACGATTGA    4800
GCGTCAAAAT GTAGGTATTT CCATGAGCGT TTTTCCTGTT GCAATGGCTG GCGGTAATAT    4860
TGTTCTGGAT ATTACCAGCA AGGCCGATAG TTTGAGTTCT TCTACTCAGG CAAGTGATGT    4920
```

```
TATTACTAAT CAAAGAAGTA TTGCGACAAC GGTTAATTTG CGTGATGGAC AGACTCTTTT      4980
ACTCGGTGGC CTCACTGATT ATAAAAACAC TTCTCAGGAT TCTGGCGTAC CGTTCCTGTC      5040
TAAAATCCCT TTAATCGGCC TCCTGTTTAG CTCCCGCTCT GATTCTAACG AGGAAAGCAC      5100
GTTATACGTG CTCGTCAAAG CAACCATAGT ACGCGCCCTG TAGCGGCGCA TTAAGCGCGG      5160
CGGGTGTGGT GGTTACGCGC AGCGTGACCG CTACACTTGC CAGCGCCCTA GCGCCCGCTC      5220
CTTTCGCTTT CTTCCCTTCC TTTCTCGCCA CGTTCGCCGG CTTTCCCCGT CAAGCTCTAA      5280
ATCGGGGGCT CCCTTTAGGG TTCCGATTTA GTGCTTTACG GCACCTCGAC CCCAAAAAAC      5340
TTGATTAGGG TGATGGTTCA CGTAGTGGGC CATCGCCCTG ATAGACGGTT TTTCGCCCTT      5400
TGACGTTGGA GTCCACGTTC TTTAATAGTG GACTCTTGTT CCAAACTGGA ACAACACTCA      5460
ACCCTATCTC GGTCTATTCT TTTGATTTAT AAGGGATTTT GCCGATTTCG GCCTATTGGT      5520
TAAAAAATGA GCTGATTTAA CAAAAATTTA ACGCGAATTT TAACAAAATA TTAACGTTTA      5580
CAATTTAAAT ATTTGCTTAT ACAATCTTCC TGTTTTGGG GCTTTTCTGA TTATCAACCG      5640
GGGTACATAT GATTGACATG CTAGTTTTAC GATTACCGTT CATCGATTCT CTTGTTTGCT      5700
CCAGACTCTC AGGCAATGAC CTGATAGCCT TTGTAGAGAC CTCTCAAAAA TAGCTACCCT      5760
CTCCGGCATG AATTTATCAG CTAGAACGGT TGAATATCAT ATTGATGGTG ATTTGACTGT      5820
CTCCGGCCTT TCTCACCCGT TTGAATCTTT ACCTACACAT TACTCAGGCA TTGCATTTAA      5880
AATATATGAG GGTTCTAAAA ATTTTTATCC TTGCGTTGAA ATAAAGGCTT CTCCCGCAAA      5940
AGTATTACAG GGTCATAATG TTTTTGGTAC AACCGATTTA GCTTTATGCT CTGAGGCTTT      6000
ATTGCTTAAT TTTGCTAATT CTTTGCCTTG CCTGTATGAT TTATTGGATG TTGGAANTTC      6060
CTGATGCGGT ATTTTCTCCT TACGCATCTG TGCGGTATTT CACACCGCAT ATGGTGCACT      6120
CTCAGTACAA TCTGCTCTGA TGCCGCATAG TTAAGCCAGC CCCGACACCC GCCAACACCC      6180
GCTGACGCGC CCTGACGGGC TTGTCTGCTC CCGGCATCCG CTTACAGACA AGCTGTGACC      6240
GTCTCCGGGA GCTGCATGTG TCAGAGGTTT TCACCGTCAT CACCGAAACG CGCGAGACGA      6300
AAGGGCCTCG TGATACGCCT ATTTTTATAG GTTAATGTCA TGATAATAAT GGTTTCTTAG      6360
ACGTCAGGTG GCACTTTTCG GGGAAATGTG CGCGGAACCC CTATTTGTTT ATTTTTCTAA      6420
ATACATTCAA ATATGTATCC GCTCATGAGA CAATAACCCT GATAAATGCT TCAATAATAT      6480
TGAAAAAGGA AGAGTATGAG TATTCAACAT TTCCGTGTCG CCCTTATTCC CTTTTTTGCG      6540
GCATTTTGCC TTCCTGTTTT TGCTCACCCA GAAACGCTGG TGAAAGTAAA AGATGCTGAA      6600
GATCAGTTGG GTGCACGAGT GGGTTACATC GAACTGGATC TCAACAGCGG TAAGATCCTT      6660
GAGAGTTTTC GCCCCGAAGA ACGTTTTCCA ATGATGAGCA CTTTTAAAGT TCTGCTATGT      6720
GGCGCGGTAT TATCCCGTAT TGACGCCGGG CAAGAGCAAC TCGGTCGCCG CATACACTAT      6780
TCTCAGAATG ACTTGGTTGA GTACTCACCA GTCACAGAAA AGCATCTTAC GGATGGCATG      6840
ACAGTAAGAG AATTATGCAG TGCTGCCATA ACCATGAGTG ATAACACTGC GGCCAACTTA      6900
CTTCTGACAA CGATCGGAGG ACCGAAGGAG CTAACCGCTT TTTTGCACAA CATGGGGGAT      6960
CATGTAACTC GCCTTGATCG TTGGGAACCG GAGCTGAATG AAGCCATACC AAACGACGAG      7020
CGTGACACCA CGATGCCTGT AGCAATGGCA ACAACGTTGC GCAAACTATT AACTGGCGAA      7080
CTACTTACTC TAGCTTCCCG GCAACAATTA ATAGACTGGA TGGAGGCGGA TAAAGTTGCA      7140
GGACCACTTC TGCGCTCGGC CCTTCCGGCT GGCTGGTTTA TTGCTGATAA ATCTGGAGCC      7200
GGTGAGCGTG GGTCTCGCGG TATCATTGCA GCACTGGGGC CAGATGGTAA GCCCTCCCGT      7260
ATCGTAGTTA TCTACACGAC GGGGAGTCAG GCAACTATGG ATGAACGAAA TAGACAGATC      7320
```

| | | | | | | |
|---|---|---|---|---|---|---|
| GCTGAGATAG | GTGCCTCACT | GATTAAGCAT | TGGTAACTGT | CAGACCAAGT | TTACTCATAT | 7380 |
| ATACTTTAGA | TTGATTTAAA | ACTTCATTTT | TAATTAAAA | GGATCTAGGT | GAAGATCCTT | 7440 |
| TTTGATAATC | TCATGACCAA | AATCCCTTAA | CGTGAGTTTT | CGTTCCACTG | AGCGTCAGAC | 7500 |
| CCCGTAGAAA | AGATCAAAGG | ATCTTCTTGA | GATCCTTTTT | TTCTGCGCGT | AATCTGCTGC | 7560 |
| TTGCAAACAA | AAAACCACC | GCTACCAGCG | GTGGTTTGTT | TGCCGGATCA | AGAGCTACCA | 7620 |
| ACTCTTTTTC | CGAAGGTAAC | TGGCTTCAGC | AGAGCGCAGA | TACCAAATAC | TGTCCTTCTA | 7680 |
| GTGTAGCCGT | AGTTAGGCCA | CCACTTCAAG | AACTCTGTAG | CACCGCCTAC | ATACCTCGCT | 7740 |
| CTGCTAATCC | TGTTACCAGT | GGCTGCTGCC | AGTGGCGATA | AGTCGTGTCT | TACCGGGTTG | 7800 |
| GACTCAAGAC | GATAGTTACC | GGATAAGGCG | CAGCGGTCGG | GCTGAACGGG | GGGTTCGTGC | 7860 |
| ACACAGCCCA | GCTTGGAGCG | AACGACCTAC | ACCGAACTGA | GATACCTACA | GCGTGAGCTA | 7920 |
| TGAGAAAGCG | CCACGCTTCC | CGAAGGGAGA | AAGGCGGACA | GGTATCCGGT | AAGCGGCAGG | 7980 |
| GTCGGAACAG | GAGAGCGCAC | GAGGGAGCTT | CCAGGGGGAA | ACGCCTGGTA | TCTTTATAGT | 8040 |
| CCTGTCGGGT | TTCGCCACCT | CTGACTTGAG | CGTCGATTTT | TGTGATGCTC | GTCAGGGGG | 8100 |
| CGGAGCCTAT | GGAAAAACGC | CAGCAACGCG | GCCTTTTTAC | GGTTCCTGGC | CTTTGCTGG | 8160 |
| CCTTTTGCTC | ACATGTTCTT | TCCTGCGTTA | TCCCTGATT | CTGTGGATAA | CCGTATTACC | 8220 |
| GCCTTTGAGT | GAGCTGATAC | CGCTCGCCGC | AGCCGAACGA | CCGAGCGCAG | CGAGTCAGTG | 8280 |
| AGCGAGGAAG | CGGAAGAGC | | | | | 8299 |